(12) United States Patent
Chin et al.

(10) Patent No.: US 12,037,340 B2
(45) Date of Patent: Jul. 16, 2024

(54) PENTACYCLIC DERIVATIVES AS ZIKA VIRUS INHIBITORS

(71) Applicant: Gilead Sciences, Inc., Foster City, CA (US)

(72) Inventors: Elbert Chin, San Mateo, CA (US); John O. Link, San Francisco, CA (US); James G. Taylor, Burlingame, CA (US); Zheng-Yu Yang, Palo Alto, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 17/748,853

(22) Filed: May 19, 2022

(65) Prior Publication Data

US 2022/0411434 A1    Dec. 29, 2022

Related U.S. Application Data

(60) Provisional application No. 63/191,678, filed on May 21, 2021.

(51) Int. Cl.
   *C07D 491/052*    (2006.01)
   *A61P 31/14*    (2006.01)

(52) U.S. Cl.
   CPC .......... *C07D 491/052* (2013.01); *A61P 31/14* (2018.01)

(58) Field of Classification Search
   CPC ........................ C07D 491/052; A61P 31/14
   See application file for complete search history.

(56) References Cited

U.S. PATENT DOCUMENTS

| | | |
|---|---|---|
| 7,704,992 B2 | 4/2010 | Bachand et al. |
| 8,088,368 B2 | 1/2012 | Guo et al. |
| 8,273,341 B2 | 9/2012 | Guo et al. |
| 8,362,068 B2 | 1/2013 | Dousson et al. |
| 8,546,402 B2 | 10/2013 | Sokoloff et al. |
| 8,575,118 B2 | 11/2013 | Guo et al. |
| 8,669,234 B2 | 3/2014 | Guo et al. |
| 8,815,858 B2 | 8/2014 | Bjornson et al. |
| 8,822,430 B2 | 9/2014 | Bacon et al. |
| 8,841,278 B2 | 9/2014 | Bacon et al. |
| 8,841,340 B2 | 9/2014 | Hashash et al. |
| 9,511,056 B2 | 12/2016 | Bacon et al. |
| 9,981,955 B2 | 5/2018 | Bacon et al. |
| 2009/0068140 A1 | 3/2009 | Bachand et al. |
| 2009/0202478 A1 | 8/2009 | Bachand et al. |
| 2009/0202483 A1 | 8/2009 | Bachand et al. |
| 2010/0080772 A1 | 4/2010 | Belema et al. |
| 2010/0160335 A1 | 6/2010 | Kohno et al. |
| 2010/0249068 A1 | 9/2010 | Beigelman et al. |
| 2010/0249190 A1 | 9/2010 | Lopez et al. |
| 2010/0316607 A1 | 12/2010 | Or et al. |
| 2011/0077280 A1 | 3/2011 | Bender et al. |
| 2011/0092415 A1 | 4/2011 | DeGoey et al. |
| 2011/0137633 A1 | 6/2011 | Hutchins et al. |
| 2011/0142798 A1 | 6/2011 | Qiu et al. |
| 2011/0150827 A1 | 6/2011 | Dousson et al. |
| 2011/0306541 A1 | 12/2011 | Delaney, IV et al. |
| 2013/0156732 A1 | 6/2013 | Bacon et al. |
| 2013/0164260 A1 | 6/2013 | Bacon et al. |
| 2013/0243726 A1 | 9/2013 | Ray et al. |
| 2013/0273005 A1 | 10/2013 | Delaney et al. |
| 2013/0309196 A1* | 11/2013 | Link ..................... A61K 45/06 424/85.4 |
| 2013/0324496 A1 | 12/2013 | Scott et al. |
| 2014/0045783 A1 | 2/2014 | Du et al. |
| 2014/0309187 A1 | 10/2014 | Hashash et al. |
| 2015/0141353 A1 | 5/2015 | Delaney, IV et al. |
| 2022/0402931 A1 | 12/2022 | Chin et al. |

FOREIGN PATENT DOCUMENTS

| | | |
|---|---|---|
| WO | WO-2006/133326 A1 | 12/2006 |
| WO | WO-2008/021927 A2 | 2/2008 |
| WO | WO-2008/021928 A2 | 2/2008 |
| WO | WO-2008/021936 A2 | 2/2008 |
| WO | WO-2008/144380 A1 | 11/2008 |
| WO | WO-2009/020825 A1 | 2/2009 |
| WO | WO-2009/020828 A1 | 2/2009 |
| WO | WO-2009/102318 A1 | 8/2009 |
| WO | WO-2009/102325 A1 | 8/2009 |
| WO | WO-2009/102568 A1 | 8/2009 |

(Continued)

OTHER PUBLICATIONS

Appel et al., "Mutational Analysis of Hepatitis C Virus Nonstructural Protein 5A Potential Role of Differential Phosphorylation in RNA Replication and Identification of a Genetically Flexible Domain", Journal of Virology, 79(5), 3187-3194 (2005).
Belema et al., Caplus An 2010:175961.
Borawski et al., "Class III Phosphatidylinositol 4-Kinase Alpha and Beta Are Novel Host Factor Regulators of Hepatitis C Virus Replication", Journal of Virology, 83(19) 10058-10074 (2009).
Das et al., Caplus An 2011:1236910.
Elazar et al., "Amphipathic Helix-Dependent Localization of NS5A Mediates Hepatitis C Virus RNA Replication", Journal of Virology, 77(10), 6055-6061 (2003).
Evans et al., "Phosphorylation of hepatitis C virus nonstructural protein 5A modulates its protein interactions and viral RNA replication", PNAS, 101(35), 13038-13043 (2004).

(Continued)

*Primary Examiner* — Timothy R Rozof

(57) ABSTRACT

Provided herein are compounds of Formula (I):
the formula(I):

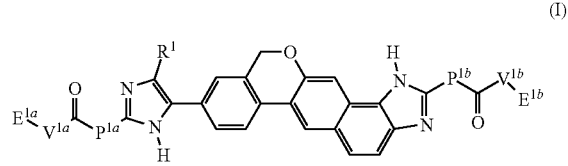

wherein the various substituents are defined herein.

6 Claims, No Drawings

(56) References Cited

FOREIGN PATENT DOCUMENTS

| WO | WO-2009/102633 A1 | 8/2009 |
|---|---|---|
| WO | WO-2010/004343 A1 | 1/2010 |
| WO | WO-2010/017401 A1 | 2/2010 |
| WO | WO-2010/062821 A1 | 6/2010 |
| WO | WO-2010/065668 A1 | 6/2010 |
| WO | WO-2010/065674 A1 | 6/2010 |
| WO | WO-2010/065681 A1 | 6/2010 |
| WO | WO-2010/091413 A1 | 8/2010 |
| WO | WO-2010/094977 A1 | 8/2010 |
| WO | WO-2010/096302 A1 | 8/2010 |
| WO | WO-2010/096462 A1 | 8/2010 |
| WO | WO-2010/096777 A1 | 8/2010 |
| WO | WO-2010/099527 A1 | 9/2010 |
| WO | WO-2010/111483 A1 | 9/2010 |
| WO | WO-2010/111534 A1 | 9/2010 |
| WO | WO-2010/111673 A1 | 9/2010 |
| WO | WO-2010/117635 A1 | 10/2010 |
| WO | WO-2010/117977 A1 | 10/2010 |
| WO | WO-2010/120621 A1 | 10/2010 |
| WO | WO-2010/120935 A1 | 10/2010 |
| WO | WO-2010/122162 A1 | 10/2010 |
| WO | WO-2010/132538 A1 | 11/2010 |
| WO | WO-2010/132601 A1 | 11/2010 |
| WO | WO-2010/138368 A1 | 12/2010 |
| WO | WO-2010/138488 A1 | 12/2010 |
| WO | WO-2010/138790 A1 | 12/2010 |
| WO | WO-2010/138791 A1 | 12/2010 |
| WO | WO-2010/144646 A2 | 12/2010 |
| WO | WO-2010/148006 A1 | 12/2010 |
| WO | WO-2011/004276 A1 | 1/2011 |
| WO | WO-2011/009084 A2 | 1/2011 |
| WO | WO-2011/015657 A1 | 2/2011 |
| WO | WO-2011/015658 A1 | 2/2011 |
| WO | WO-2011/026920 A1 | 3/2011 |
| WO | WO-2011/028596 A1 | 3/2011 |
| WO | WO-2011/031904 A1 | 3/2011 |
| WO | WO-2011/031934 A1 | 3/2011 |
| WO | WO-2011/046811 A1 | 4/2011 |
| WO | WO-2011/050146 A1 | 4/2011 |
| WO | WO-2011/054834 A1 | 5/2011 |
| WO | WO-2011/059850 A1 | 5/2011 |
| WO | WO-2011/059887 A1 | 5/2011 |
| WO | WO-2011/060060 A1 | 5/2011 |
| WO | WO-2011/066241 A1 | 6/2011 |
| WO | WO-2011/075439 A1 | 6/2011 |
| WO | WO-2011/075607 A1 | 6/2011 |
| WO | WO-2011/075615 A1 | 6/2011 |
| WO | WO-2011/079327 A1 | 6/2011 |
| WO | WO-2011/082077 A1 | 7/2011 |
| WO | WO-2011/087740 A1 | 7/2011 |
| WO | WO-2011/091446 A1 | 7/2011 |
| WO | WO-2011/112429 A1 | 9/2011 |
| WO | WO-2011/146401 A1 | 11/2011 |
| WO | WO-2012/027712 A2 | 3/2012 |
| WO | WO-2012/041014 A1 | 4/2012 |
| WO | WO-2012/048421 A1 | 4/2012 |
| WO | WO-2012/068234 A2 | 5/2012 |
| WO | WO-2012/087976 A2 | 6/2012 |
| WO | WO-2013/075029 A1 | 5/2013 |
| WO | WO-2013/173488 A1 | 11/2013 |
| WO | WO-2014/100500 A1 | 6/2014 |
| WO | WO-2015/191526 A2 | 12/2015 |
| WO | WO-2018/017426 A1 | 1/2018 |
| WO | WO-2018/170513 A1 | 9/2018 |
| WO | WO-2020/210428 A1 | 10/2020 |

OTHER PUBLICATIONS

Freundt et al., "Interfering with interferons: Hepatitis C virus counters innate immunity", PNAS, 102(49), 17539-17540 (2005).
Gao et al., "Chemical genetics strategy identifies an HCV NS5A inhibitor with a potent clinical effect", Nature, 465(6), 96-102 (2010).
Gao et al., "New BMS HCV NS5A Inhibitor: From Screen Hit to Clinic", http://www.natap.org/2008/HCV/101408_01.htm, 1-9 (2010).
Gastaminza et al., "Antiviral Stilbene 1,2 Diamines Prevent Initiation of Hepatitis C Virus RNA Replication at the Outset of Infection", Journal of Virology, 85(11), 5513-5523 (2011).
Han et al. (2018) "Investigational drugs for the treatment of Zika virus infection: a preclinical and clinical update", Export Opinion on Investigational Drugs 27(12): 951-962.
HCV—prevention, 2014, http://www.webmd.com/hepatitis/understanding-hepatitis-c-prevention.
HepatitisC, http://en.wikipedia.org/wiki/Hepatitis_C, 2012.
Huang et al., "Phosphorylation of hepatitis C virus NS5A nonstructural protein: A new paradigm for phosphorylation-dependent viral RNA replication?", Virology, 364, 1-9, (2007).
Hughes et al., "Domain III of NS5A contributes to both RNA replication and assembly of hepatitis C virus particles", Journal of General Virology, 90, 1329-1334 (2009).
Jones et al., "In-cell click labelling of small molecules to determine subcellular localisation", J. Chem. Biol., 4, 49-53 (2011).
Kanda et al., "Inhibition of Intrahepatic Gamma Interferon Production by Hepatitis C Virus Nonstructural Protein 5A in Transgenic Mice", Journal of Virology, 83(17), 8463-8469 (2009).
Katze et al., "Ser2194 Is a highly Conserved Major Phosphorylation Site of the Hepatitis C Virus Nonstructural Protein NS5A", Virology, 278, 501-513 (2000).
Kaul et al., "Essential Role of Cyclophilin A for Hepatitis C Virus Replication and Virus Production and Possible Link to Polyprotein Cleavage Kinetics", PLoSPathogens, 5(8), 1-18 (2009).
Krieger et al., "Enhancement of Hepatitis C Virus RNA Replication by Cell Culture-Adaptive Mutations", Journal of Virology, 75(10), 4614-4624 (2001).
Kriegs et al., The Hepatitis C Virus Non-Structural NS5A Protein Impairs Both the Innate and Adaptive Hepatic Immune Response in Vivo, The Journal of Biological Chemistry, 284, 28343-28351 (2009).
Lee et al., "The hepatitis C virus NS5A inhibitor (BMS-790052) alters the subcellular localization of the non-structural viral protein", Virology, 414, 10-18, (2011).
Lemm et al., "Discovery of Potent Hepatitis C Virus NS5A Inhibitors with Dimeric Structures", AAC Accepts, 1-30 (2011).
Lemm et al., "Identification of Hepatitis C Virus NS5A Inhibitors", Journal of Virology, 84(1), 482-491 (2010).
Link et al. (2019) "Discovey of velpatasvir (GS-5816): A potent pan-genotypic HCV NS5A inhibitor in the single-tablet regimens Vosevi and Epclusa", Bioorganic & Medicial Chemistry Letters 29(16):2415-2427.
Liver Cancer, 2011, http://www.biomedcentral.com/1471-2458/9/34.
LiverCancer2, 2011, http://www.mayoclinic.com/health/liver-cancer/DS00399/DSECTION=causes.
Lohmann et al., "Mutations in Hepatitis C Virus RNAs Conferring Cell Culture Adaptation", Journal of Virology, 75(3), 1437-1449 (2001).
MacDonald et al., "Hepatitis C virus NS5A: tales of a promiscuous protein", Journal of General Virology, 85, 2485-2502 (2004).
McCormick et al., "Tagging of NS5A expressed from a functional hepatitis C virus replicon", Journal of General Virology, 87, 635-640 (2006).
Miyanari et al., "Hepatits C Virus Non-structural Proteins in the Probable Membranous Compartment Function in Viral Genome Replication", The Journal of Biological Chemistry, 278(50), 50301-50308 (2003).
Moradpour et al., "Replication of hepatitis C virus", Nature Reviews Microbiology, 5, 453-463 (2007).
Pietschmann et al., "Characterization of Cell Lines Carrying Self-Replicating Hepatitis C Virus RNAs", Journal of Virology, 75(3), 1252-1264 (2001).
Reed et al., "The NS5A Proteins of Viruses from Three Genera of the Family Flaviviridae Are Phosphorylated by Associated Serine/Threonine Kinases", Journal of Virology, 75(3), 1252-1264 (2001).
Reynolds et al., "Thermodynamics of Ligand Binding and Efficiency", ACS Medicinal Chemistry Letters, 2(6):433-437 (2011).

(56) References Cited

OTHER PUBLICATIONS

Romine et al., "Inhibitors of HCV NS5A: From Iminothiazolidinones to Symmetrical Stilbenes", ACS Medicinal Chemistry Letters, A-F (2010).

Scheel, et al., "Recombinant HCV Variants with NS5A from Genotypes 1-7 Have Different Sensitivities to an NS5A Inhibitor but Not interferon-a", Gastroenterology, (2011), 140(3), 1032-1042.

Schmitz et al., "NS5A—From Obscurity to New Target for HCV Therapy", Recent Patents on Anti-Infective Drug Discovery, 3, 77-92 (2008).

Shimakami et al., "Hepatitis C: Recent Successes and Continuing Challenges in the Development of Improved Treatment Modalities", Curr Opin Pharmacol., 9(5), 537-544 (2009).

Tellinghuisen et al., "Regulation of Hepatitis C Virion Production via Phosphorylation of the NS5A Protein", PLoSPathogens, 4(3), 1-17 (2008).

Tellinghuisen et al., "Structure of the Zinc-Binding Domain of an Essential Replicase Component of Hepatitis C Virus Reveals a Novel Fold", Nature, 435(7040), 374-379 (2005).

Tellinghuisen et al., "The NS5A Protein of Hepatitis C Virus Is a Zinc Metalloprotein", Journal of Biological Chemistry, 279(47), 48576-48587 (2004).

Vitale et al., "2-Arylbenzimidazoles as Antiviral and Antiproliferative Agents—Part 1", Medicinal Chemistry, 4, pp. 605-615 (2008).

Zou et al. (2020) "Structure-activity relationship of flavonoid bifunctional inhibitors against Zika virus infection", Biochemical Pharmacology 177: 1-9.

Intl. Search Report—Written Opinion dated Aug. 17, 2022 for Intl. Appl. No. PCT/US2022/030104, 15 pages.

Intl. Preliminary Report on Patentability dated Nov. 21, 2023 for Intl. Appl. No. PCT/US2022/030104, 8 pages.

* cited by examiner

PENTACYCLIC DERIVATIVES AS ZIKA VIRUS INHIBITORS

CROSS-REFERENCE TO RELATED APPLICATIONS

This patent application claims the benefit under 35 U.S.C. § 119(e) of U.S. Provisional Patent Application No. 63/191,678, filed May 21, 2021. The foregoing application is incorporated herein by reference in its entirety.

BACKGROUND OF THE INVENTION

Zika virus is a mosquito-transmitted, single stranded, positive sense RNA flavivirus that has emerged from relative obscurity to cause an epidemic of great public health concern. Outbreaks of Zika virus disease have been recorded in Africa, the Americas, Asia and the Pacific. The introduction of Zika virus into the Western Hemisphere is believed to have occurred in 2014-2015 in Haiti and Brazil and spread rapidly to 33 or more countries. Historically, symptomatic Zika virus infection of humans was described as a self-limiting mild febrile illness associated with rash, arthralgia, and conjunctivitis. However, recent Zika virus infection has also been associated with neurological complications, including Guillain-Barré syndrome and meningoencephalitis. Of significant concern, Zika virus infection is now strongly linked to microcephaly and intrauterine growth retardation in the fetuses of women infected with the virus while pregnant. Zika infection in pregnancy also may result in pregnancy complications such as fetal loss, stillbirth, and preterm birth.

There is currently no vaccine to prevent Zika virus disease. Therefore, there is a need for therapeutic or prophylactic interventions to treat or prevent Zika virus disease, particularly in women of childbearing age.

SUMMARY OF THE INVENTION

Provided herein are compounds and methods for the treatment or prevention of Zika virus infection.

In one embodiment the compounds are generally of the formula(I):

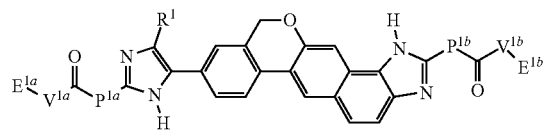

wherein:
$R^{1a}$ and $R^{1b}$ are each independently halo, $C_{1-6}$ alkyl, or cycloalkyl;
$P^{1a}$ is selected from the group consisting of:

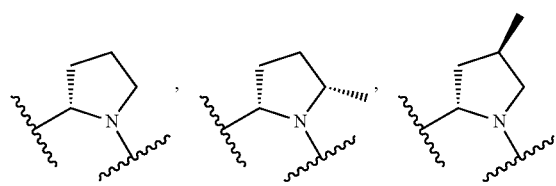

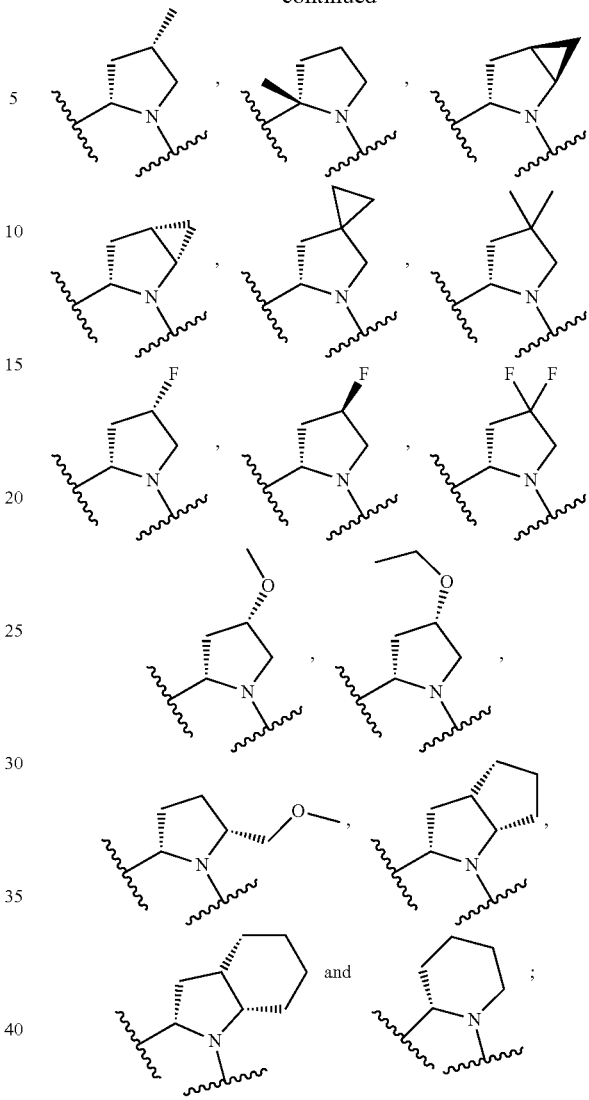

$P^{1b}$ is selected from the group consisting of:

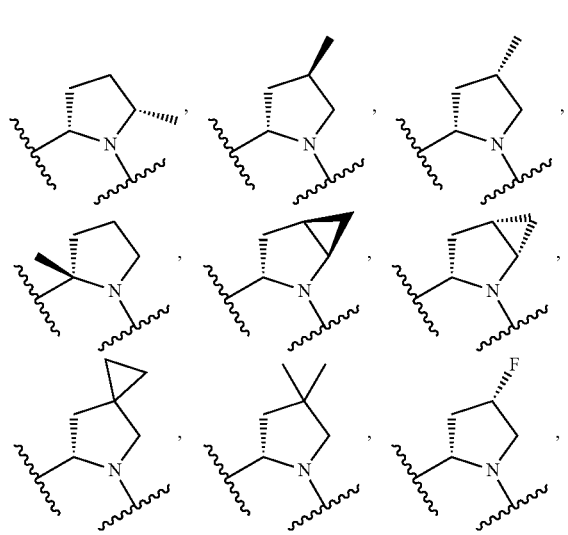

3
-continued

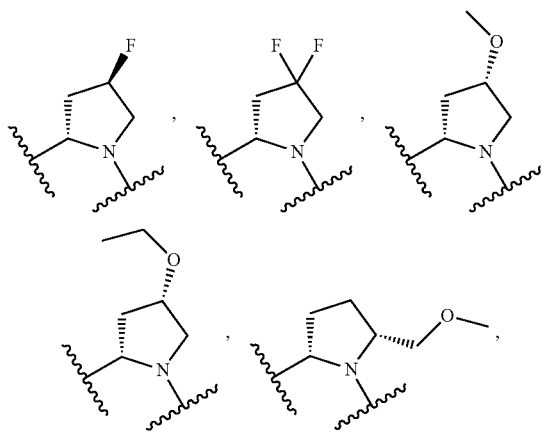

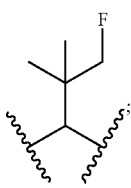

-continued

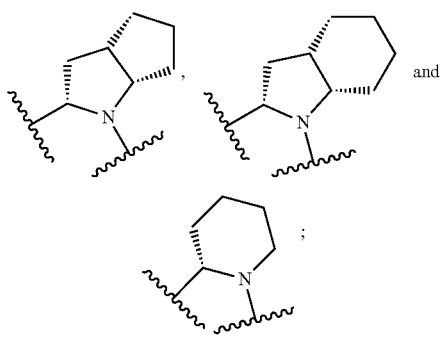

$V^{1a}$ and $V^{1b}$ are each independently selected from the group consisting of:

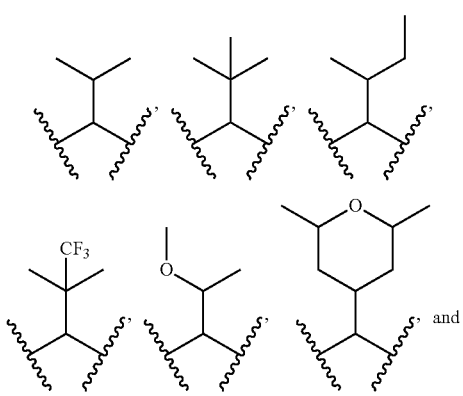

4
-continued $E^{1a}$ and $E^{1b}$ are each independently —N(H)(C$_{1-6}$ alkoxycarbonyl), N(H)(C$_{3-12}$ cycloalkylcarbonyl), N(H)(C$_{1-6}$ alkylcarbonyl), or —N(H)(C$_{3-12}$ cycloalkoxycarbonyl); or a stereoisomer, pharmaceutically acceptable salt or solvate thereof.

In another embodiment, there is provided a pharmaceutical composition comprising a compound of formula (I):

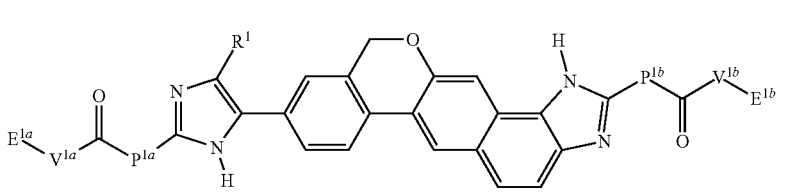

(I)

wherein:
$R^1$ is halo, C$_{1-10}$ alkyl, C$_{3-12}$ cycloalkyl, or cyano;
$P^{1a}$ and $P^{1b}$ are each independently selected from:

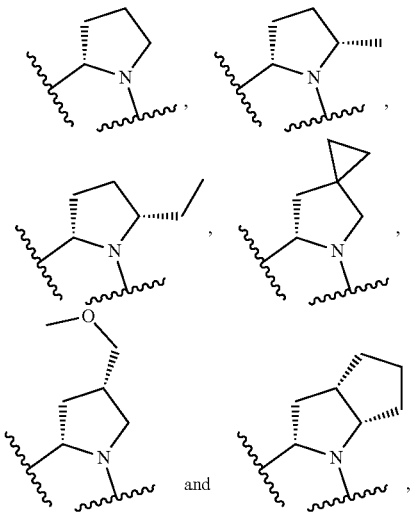

$V^{1a}$ and $V^{1b}$ are each independently selected from:

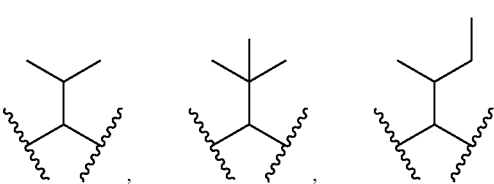

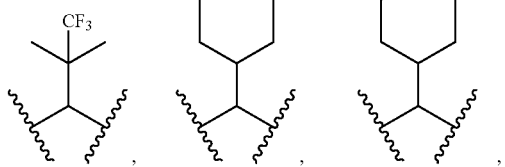

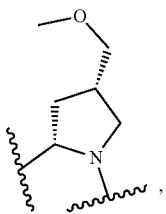 [SMILES: *[C@@H]1C[C@H](COC)CN1*]

$V^{1a}$ and $V^{1b}$ are both

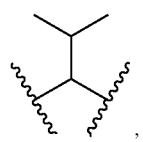 [SMILES: *C(*)C(C)C]

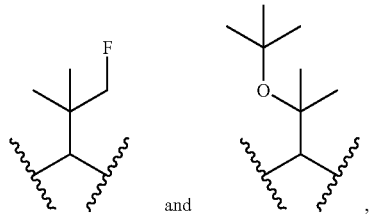

$E^{1a}$ and $E^{1b}$ are each independently —N(H)(C$_{1-6}$ alkoxycarbonyl), N(H)(cycloalkylcarbonyl), N(H)(alkylcarbonyl), or —N(H)(cycloalkoxycarbonyl);

provided that when P$^{1a}$ is then R$^1$ is halo, C$_{1-6}$ alkyl, C$_{4-7}$ cycloalkyl, or cyano; or a pharmaceutically acceptable salt, stereoisomer, or solvate thereof, together with a pharmaceutically acceptable excipient.

In another embodiment of the present invention, there is provided a method of treating a Zika virus infection, in a subject in need thereof, comprising administering to said subject a compound of formula (I):

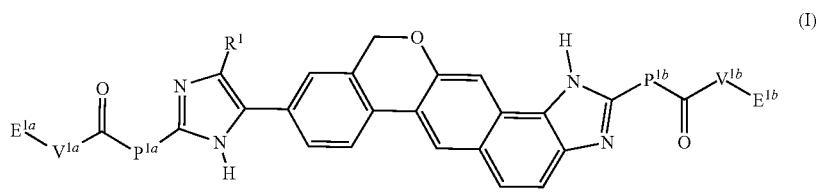

wherein:

R[1] is halo, $C_{1-10}$ alkyl, $C_{3-12}$ cycloalkyl, or cyano;

$P^{1a}$ and $P^{1b}$ are each independently selected from:

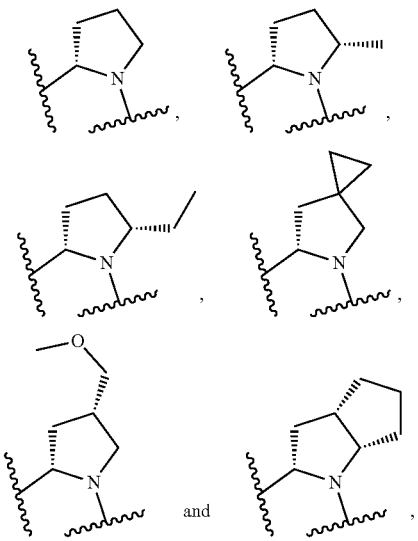

$V^{1a}$ and $V^{1b}$ are each independently selected from:

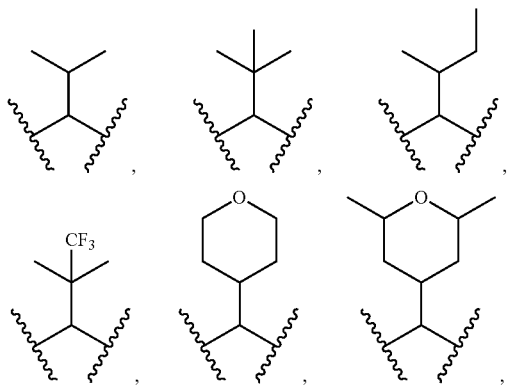

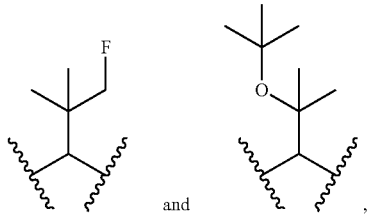

and $E^{1a}$ and $E^{1b}$ are each independently —N(H)($C_{1-6}$ alkoxycarbonyl), N(H)(cycloalkylcarbonyl), N(H)(alkylcarbonyl), or —N(H)(cycloalkoxycarbonyl);

provided that when $P^{1a}$ is

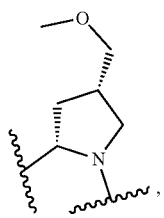 [SMILES: *[C@@H]1C[C@H](COC)CN1*]

$V^{1a}$ and $V^{1b}$ are both

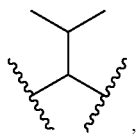 [SMILES: *C(*)C(C)C]

then R[1] is halo, $C_{1-6}$ alkyl, $C_{4-7}$ cycloalkyl, or cyano; or a pharmaceutically acceptable salt, stereoisomer, or solvate thereof.

In another embodiment, the subject is a human.

In another embodiment, the subject is a female subject of childbearing age.

In another embodiment, the subject is a pregnant female.

In another embodiment, the compound is admixed with a pharmaceutically acceptable excipient in a pharmaceutical composition.

In another embodiment, there is provided a method of preventing a Zika virus infection, comprising administering to a subject in need thereof a compound of formula (I):

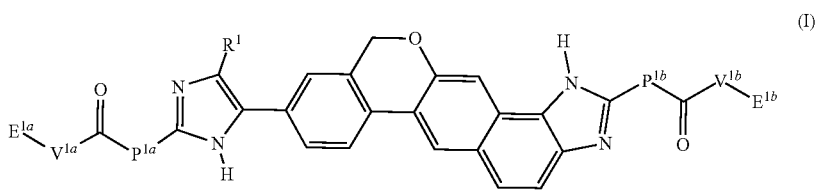

wherein:

$R^1$ is halo, $C_{1-10}$ alkyl, $C_{3-12}$ cycloalkyl, or cyano;

$P^{1a}$ and $P^{1b}$ are each independently selected from:

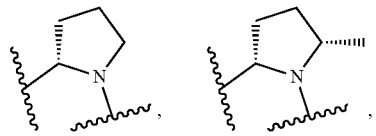

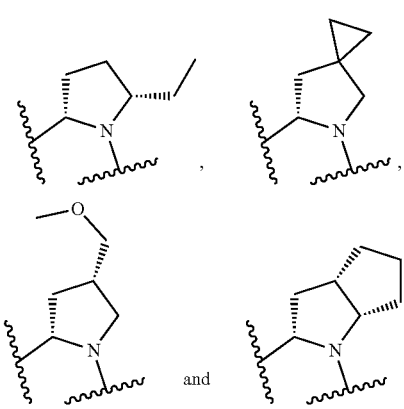

$V^{1a}$ and $V^{1b}$ are each independently selected from:

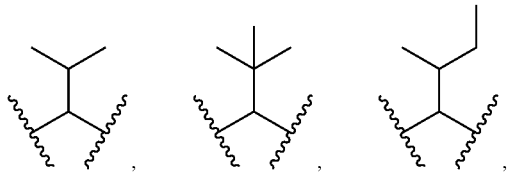

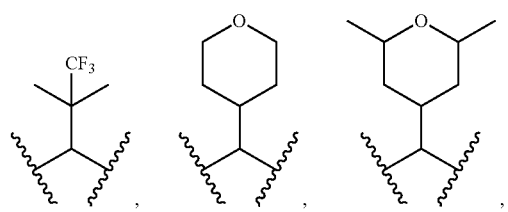

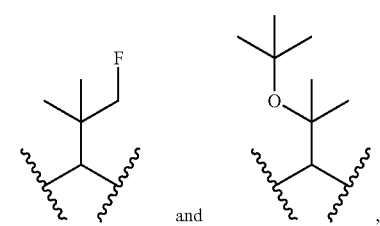

$E^{1a}$ and $E^{1b}$ are each independently —N(H)($C_{1-6}$ alkoxycarbonyl), N(H)(cycloalkylcarbonyl), N(H)(alklcarbonyl), or —N(H)(cycloalkoxycarbonyl);

provided that when $P^{1a}$ is

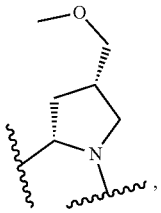 [SMILES: *[C@@H]1C[C@H](COC)CN1*]

$V^{1a}$ and $V^{1b}$ are both

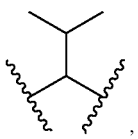 [SMILES: *C(*)C(C)C]

then $R^1$ is halo, $C_{1-6}$ alkyl, $C_{4-7}$ cycloalkyl, or cyano; or a pharmaceutically acceptable salt, stereoisomer, or solvate thereof.

In another embodiment, the subject is a human.

In another embodiment, the subject is a female subject of childbearing age.

In another embodiment, the subject is a pregnant female.

In another embodiment, the compound is admixed with a pharmaceutically acceptable excipient in a pharmaceutical composition. Other and further embodiments will occur to those skilled in the art, and minor modifications are intended to be encompassed by the appended claims.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the embodiments.

Whenever a compound described herein is substituted with more than one of the same designated group, e.g., "$R^1$" or "$A^3$", then it will be understood that the groups may be the same or different, i.e., each group is independently selected.

"Absent"—Some groups are defined such that they can be absent. When a group is absent it becomes a bond connector. The two groups that would otherwise be connected to that absent group are connected to each other through a bond. For example, when W is absent, M is bonded to M.

"Alkyl" is $C_1$-$C_{18}$ hydrocarbon containing normal, secondary, tertiary or cyclic carbon atoms. Examples are methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH₃)CH₂CH₃), 2-methyl-2-propyl (t-Bu, t-butyl, —C(CH₃)₃), 1-pentyl (n-pentyl, —CH₂CH₂CH₂CH₂CH₃), 2-pentyl (—CH(CH₃)CH₂CH₂CH₃), 3-pentyl (—CH(CH₂CH₃)₂), 2-methyl-2-butyl (—C(CH₃)₂CH₂CH₃), 3-methyl-2-butyl (—CH(CH₃)CH(CH₃)₂), 3-methyl-1-butyl (—CH₂CH₂CH(CH₃)₂), 2-methyl-1-butyl (—CH₂CH(CH₃)CH₂CH₃), 1-hexyl (—CH₂CH₂CH₂CH₂CH₂CH₃), 2-hexyl (—CH(CH₃)CH₂CH₂CH₂CH₃), 3-hexyl (—CH(CH₂CH₃)(CH₂CH₂CH₃)), 2-methyl-2-pentyl (—C(CH₃)₂CH₂CH₂CH₃), 3-methyl-2-pentyl (—CH(CH₃)CH(CH₃)CH₂CH₃), 4-methyl-2-pentyl (—CH(CH₃)CH₂CH(CH₃)₂), 3-methyl-3-pentyl (—C(CH₃)(CH₂CH₃)₂), 2-methyl-3-pentyl (—CH(CH₂CH₃)CH(CH₃)₂), 2,3-dimethyl-2-butyl (—C(CH₃)₂CH(CH₃)₂), 3,3-dimethyl-2-butyl (—CH(CH₃)C(CH₃)₃, and cyclopropylmethyl

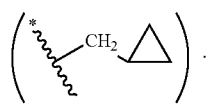

"Alkenyl" is C₂-C₁₈ hydrocarbon containing normal, secondary, tertiary or cyclic carbon atoms with at least one site of unsaturation, i.e. a carbon-carbon, sp² double bond. Examples include, but are not limited to, ethylene or vinyl (—CH=CH₂), allyl (—CH₂CH=CH₂), cyclopentenyl (—C₅H₇), and 5-hexenyl (—CH₂CH₂CH₂CH₂CH=CH₂).

"Alkynyl" is C₂-C₁₈ hydrocarbon containing normal, secondary, tertiary or cyclic carbon atoms with at least one site of unsaturation, i.e. a carbon-carbon, sp triple bond. Examples include, but are not limited to, acetylenic (—C≡CH) and propargyl (—CH₂C≡CH).

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to, methylene (—CH₂—) 1,2-ethyl (—CH₂CH₂—), 1,3-propyl (—CH₂CH₂CH₂—), 1,4-butyl (—CH₂CH₂CH₂CH₂—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to, 1,2-ethylene (—CH=CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to, acetylene (—C≡C—), propargyl (—CH₂C≡C—), and 4-pentynyl (—CH₂CH₂CH₂C≡CH).

"Aryl" means a monovalent aromatic hydrocarbon radical of 6-20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Arylalkyl" refers to an acyclic alkyl radical in which one of the hydrogen atoms bonded to a carbon atom, typically a terminal or sp³ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group comprises 6 to 20 carbon atoms, e.g., the alkyl moiety, including alkanyl, alkenyl or alkynyl groups, of the arylalkyl group is 1 to 6 carbon atoms and the aryl moiety is 5 to 14 carbon atoms.

The term "polycarbocycle" refers to a saturated or unsaturated polycyclic ring system having from about 6 to about 25 carbon atoms and having two or more rings (e.g. 2, 3, 4, or 5 rings). The rings can be fused and/or bridged to form the polycyclic ring system. For example, the term includes bicyclo [4,5], [5,5], [5,6] or [6,6] ring systems, as well as the following bridged ring systems:

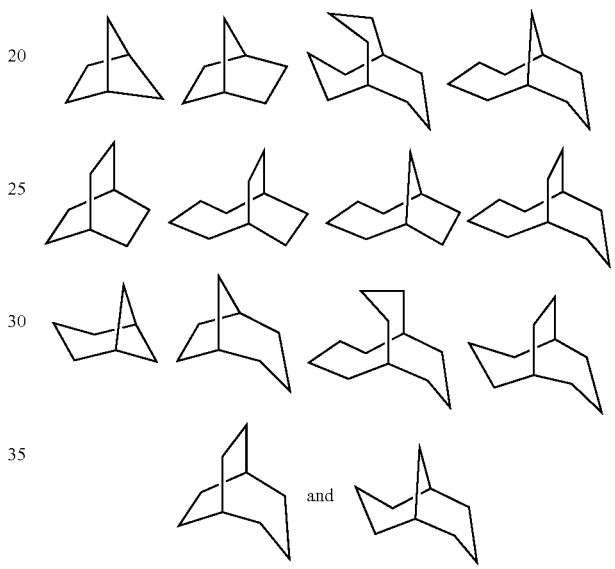

(i.e., [2.1.1], [2.2.1], [3.3.3], [4.3.1], [2.2.2], [4.2.2], [4.2.1], [4.3.2], [3.1.1], [3.2.1], [4.3.3], [3.3.2], [3.2.2] and [3.3.1] polycyclic rings, respectively) that can be linked to the remainder of the compound of formula (I) through any synthetically feasible position. Like the other polycarbocycles, these representative bicyclo and fused ring systems can optionally comprise one or more double bonds in the ring system.

The term "polyheterocycle" refers to a polycarbocycle as defined herein, wherein one or more carbon atoms is replaced with a heteroatom (e.g., O, S, S(O), S(O)₂, N⁺(O⁻)R$_x$, or NR$_x$); wherein each R$_x$ is independently H, (C1-10)alkyl, (C2-10)alkenyl, (C2-10)alkynyl, (C1-10)alkanoyl, S(O)₂NR$_n$R$_p$, S(O)₂R$_x$, or (C1-10)alkoxy, wherein each (C1-10)alkyl, (C2-10)alkenyl, (C2-10)alkynyl, (C1-10)alkanoyl, and (C1-10)alkoxy is optionally substituted with one or more halo).

"Substituted alkyl", "substituted aryl", and "substituted arylalkyl" mean alkyl, aryl, and arylalkyl respectively, in which one or more hydrogen atoms are each independently replaced with a non-hydrogen substituent. Typical substituents include, but are not limited to: halo (e.g. F, Cl, Br, I), —R, —OR, —SR, —NR₂, —CF₃, —CCl₃, —OCF₃, —CN, —NO₂, —N(R)C(=O)R, —C(=O)R, —OC(=O)R, —C(O)OR, —C(=O)NRR, —S(=O)R, —S(=O)₂OR, —S(=O)₂R, —OS(=O)₂OR, —S(=O)₂NRR, and each R is independently —H, alkyl, aryl, arylalkyl, or heterocycle. Alkylene, alkenylene, and alkynylene groups may also be similarly substituted.

The term "optionally substituted" in reference to a particular moiety of the compound of formula I, (e.g., an optionally substituted aryl group) refers to a moiety having 0, 1, 2, or more substituents.

The symbol " ----- " in a ring structure means that a bond is a single or double bond. In a non-limiting example,

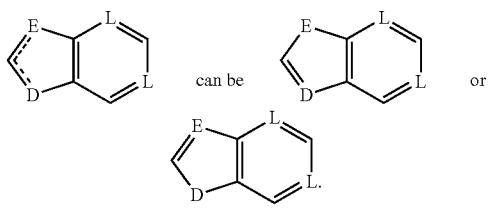

"Haloalkyl" as used herein includes an alkyl group substituted with one or more halogens (e.g. F, Cl, Br, or I). Representative examples of haloalkyl include trifluoromethyl, 2,2,2-trifluoroethyl, and 2,2,2-trifluoro-1-(trifluoromethyl)ethyl.

"Heterocycle" as used herein includes by way of example and not limitation these heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S).

Examples of heterocycles include by way of example and not limitation pyridyl, dihydropyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4H-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

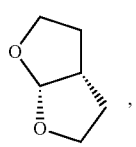

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" refers to a saturated, unsaturated or aromatic ring having up to about 25 carbon atoms. Typically, a carbocycle has about 3 to 7 carbon atoms as a monocycle, about 7 to 12 carbon atoms as a bicycle, and up to about 25 carbon atoms as a polycycle. Monocyclic carbocycles typically have 3 to 6 ring atoms, still more typically 5 or 6 ring atoms. Bicyclic carbocycles typically have 7 to 12 ring atoms, e.g., arranged as a bicyclo [4,5], [5,5], [5,6] or [6,6] system, or 9 or 10 ring atoms arranged as a bicyclo [5,6] or [6,6] system. The term carbocycle includes "cycloalkyl" which is a saturated or unsaturated carbocycle. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The term "treatment" or "treating," to the extent it relates to a disease or condition includes preventing the disease or condition from occurring, inhibiting the disease or condition, eliminating the disease or condition, and/or relieving one or more symptoms of the disease or condition.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes (D and L) or (R and S) are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. The invention includes all stereoisomers of the compounds described herein.

The term "alkenyl," as used herein, refers to a straight or branched chain group of two to six carbon atoms containing at least one carbon-carbon double bond.

The term "alkenyloxy," as used herein, refers to an alkenyl group attached to the parent molecular moiety through an oxygen atom.

The term "alkenyloxycarbonyl," as used herein, refers to an alkenyloxy group attached to the parent molecular moiety through a carbonyl group.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxyalkylcarbonyl," as used herein, refers to an alkoxyalkyl group attached to the parent molecular moiety through a carbonyl group.

The term "alkoxycarbonyl," as used herein, refers to an alkoxy group attached to the parent molecular moiety through a carbonyl group.

The term "alkoxycarbonylalkyl," as used herein, refers to an alkyl group substituted with one, two, or three alkoxycarbonyl groups.

The term "alkyl," as used herein, refers to a group derived from a straight or branched chain saturated hydrocarbon containing from one to six carbon atoms.

The term "alkylcarbonyl," as used herein, refers to an alkyl group attached to the parent molecular moiety through a carbonyl group.

The term "alkylcarbonylalkyl," as used herein, refers to an alkyl group substituted with one, two, or three alkylcarbonyl groups.

The term "alkylcarbonyloxy," as used herein, refers to an alkylcarbonyl group attached to the parent molecular moiety through an oxygen atom.

The term "alkylsulfanyl," as used herein, refers to an alkyl group attached to the parent molecular moiety through a sulfur atom.

The term "alkylsulfonyl," as used herein, refers to an alkyl group attached to the parent molecular moiety through a sulfonyl group.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present disclosure can be attached to the parent molecular moiety through any substitutable carbon atom in the group. Representative examples of aryl groups include, but are not limited to, indanyl, indenyl, naphthyl, phenyl, and tetrahydronaphthyl. The aryl groups of the present disclosure are optionally substituted with one, two, three, four, or five substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR$^X$R$^Y$, —(NR$^X$R$^Y$)alkyl, oxo, and —P(O)OR$_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro.

The term "arylalkenyl," as used herein, refers to an alkenyl group substituted with one, two, or three aryl groups.

The term "arylalkoxy," as used herein, refers to an aryl group attached to the parent molecular moiety through an alkoxy group.

The term "arylalkoxyalkyl," as used herein, refers to an alkyl group substituted with one, two, or three arylalkoxy groups.

The term "arylalkoxyalkylcarbonyl," as used herein, refers to an arylalkoxyalkyl group attached to the parent molecular moiety through a carbonyl group.

The term "arylalkoxycarbonyl," as used herein, refers to an arylalkoxy group attached to the parent molecular moiety through a carbonyl group.

The term "arylalkyl," as used herein, refers to an alkyl group substituted with one, two, or three aryl groups. The alkyl part of the arylalkyl is further optionally substituted with one or two additional groups independently selected from alkoxy, alkylcarbonyloxy, halo, haloalkoxy, haloalkyl, heterocyclyl, hydroxy, and —NR$^c$R$^d$, wherein the heterocyclyl is further optionally substituted with one or two substituents independently selected from alkoxy, alkyl, unsubstituted aryl, unsubstituted arylalkoxy, unsubstituted arylalkoxycarbonyl, halo, haloalkoxy, haloalkyl, hydroxy, and —NR$^X$R$^Y$;

The term "arylalkylcarbonyl," as used herein, refers to an arylalkyl group attached to the parent molecular moiety through a carbonyl group.

The term "arylcarbonyl," as used herein, refers to an aryl group attached to the parent molecular moiety through a carbonyl group.

The term "aryloxy," as used herein, refers to an aryl group attached to the parent molecular moiety through an oxygen atom.

The term "aryloxyalkyl," as used herein, refers to an alkyl group substituted with one, two, or three aryloxy groups.

The term "aryloxycarbonyl," as used herein, refers to an aryloxy group attached to the parent molecular moiety through a carbonyl group.

The term "arylsulfanyl," as used herein, refers to an aryl group attached to the parent molecular moiety through a sulfur atom.

The term "arylsulfonyl," as used herein, refers to an aryl group attached to the parent molecular moiety through a sulfonyl group.

The terms "Cap" and "cap" as used herein, refer to the group which is placed on the nitrogen atom of the terminal nitrogen-containing ring. It should be understood that "Cap" or "cap" can refer to the reagent used to append the group to the terminal nitrogen-containing ring or to the fragment in the final product.

The term "carbonyl," as used herein, refers to —C(=O)—.

The term "carboxy," as used herein, refers to —CO$_2$H.

The term "cyano," as used herein, refers to —CN.

The term "cyanoalkyl" as used herein, refers to an alkyl group having at least one —CN substituent.

The term "cycloalkyl," as used herein, refers to a saturated monocyclic, hydrocarbon ring system having three to seven carbon atoms and zero heteroatoms. Representative examples of cycloalkyl groups include, but are not limited to, cyclopropyl, cyclopentyl, and cyclohexyl. The cycloalkyl groups of the present disclosure are optionally substituted with one, two, three, four, or five substituents independently selected from alkoxy, alkyl, aryl, cyano, halo, haloalkoxy, haloalkyl, heterocyclyl, hydroxy, hydroxyalkyl, nitro, and —NR$^X$R$^Y$ wherein the aryl and the heterocyclyl are further optionally substituted with one, two, or three substituents independently selected from alkoxy, alkyl, cyano, halo, haloalkoxy, haloalkyl, hydroxy, and nitro.

The term "(cycloalkyl)alkenyl," as used herein, refers to an alkenyl group substituted with one, two, or three cycloalkyl groups.

The term "(cycloalkyl)alkyl," as used herein, refers to an alkyl group substituted with one, two, or three cycloalkyl groups. The alkyl part of the (cycloalkyl)alkyl is further optionally substituted with one or two groups independently selected from hydroxy and —NR$^c$R$^d$.

The term "cycloalkyloxy," as used herein, refers to a cycloalkyl group attached to the parent molecular moiety through an oxygen atom.

The term "cycloalkyloxyalkyl," as used herein, refers to an alkyl group substituted with one, two, or three cycloalkyloxy groups.

The term "cycloalkylsulfonyl," as used herein, refers to a cycloalkyl group attached to the parent molecular moiety through a sulfonyl group.

The term "formyl," as used herein, refers to —CHO.

The terms "halo" and "halogen," as used herein, refer to F, Cl, Br, or I.

The term "haloalkoxy," as used herein, refers to a haloalkyl group attached to the parent molecular moiety through an oxygen atom.

The term "haloalkoxycarbonyl," as used herein, refers to a haloalkoxy group attached to the parent molecular moiety through a carbonyl group.

The term "haloalkyl," as used herein, refers to an alkyl group substituted by one, two, three, or four halogen atoms.

The term "haloalkylsulfanyl," as used herein, refers to a haloalkyl group attached to the parent molecular moiety through a sulfur atom.

The term "heterocyclyl," as used herein, refers to a four-, five-, six-, or seven-membered ring containing one, two, three, or four heteroatoms independently selected from nitrogen, oxygen, and sulfur. The four-membered ring has zero double bonds, the five-membered ring has zero to two double bonds, and the six- and seven-membered rings have zero to three double bonds. The term "heterocyclyl" also includes bicyclic groups in which the heterocyclyl ring is fused to another monocyclic heterocyclyl group, or a four- to six-membered aromatic or non-aromatic carbocyclic ring; as well as bridged bicyclic groups such as 7-azabicyclo[2.2.1]hept-7-yl, 2-azabicyclo[2.2.2]oc-2-tyl, and 2-azabicyclo[2.2.2]oc-3-tyl. The heterocyclyl groups of the present disclosure can be attached to the parent molecular moiety through any carbon atom or nitrogen atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, thiomorpholinyl, 7-azabicyclo[2.2.1]hept-7-yl, 2-azabicyclo[2.2.2]oc-2-tyl, and 2-azabicyclo[2.2.2]oc-3-tyl. The heterocyclyl groups of the present disclosure are optionally substituted with one, two, three, four, or five substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^X$R$^Y$, —(NR$^X$R$^Y$)alkyl, and oxo, wherein the alkyl part of the arylalkyl and the heterocyclylalkyl are unsubstituted and wherein the aryl, the aryl part of the arylalkyl, the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro.

The term "heterocyclylalkenyl," as used herein, refers to an alkenyl group substituted with one, two, or three heterocyclyl groups.

The term "heterocyclylalkoxy," as used herein, refers to a heterocyclyl group attached to the parent molecular moiety through an alkoxy group.

The term "heterocyclylalkoxycarbonyl," as used herein, refers to a heterocyclylalkoxy group attached to the parent molecular moiety through a carbonyl group.

The term "heterocyclylalkyl," as used herein, refers to an alkyl group substituted with one, two, or three heterocyclyl groups. The alkyl part of the heterocyclylalkyl is further optionally substituted with one or two additional groups independently selected from alkoxy, alkylcarbonyloxy, aryl, halo, haloalkoxy, haloalkyl, hydroxy, and —NR$^c$R$^d$, wherein the aryl is further optionally substituted with one or two substituents independently selected from alkoxy, alkyl, unsubstituted aryl, unsubstituted arylalkoxy, unsubstituted arylalkoxycarbonyl, halo, haloalkoxy, haloalkyl, hydroxy, and —NR$^X$R$^Y$.

The term "heterocyclylalkylcarbonyl," as used herein, refers to a heterocyclylalkyl group attached to the parent molecular moiety through a carbonyl group.

The term "heterocyclylcarbonyl," as used herein, refers to a heterocyclyl group attached to the parent molecular moiety through a carbonyl group.

The term "heterocyclyloxy," as used herein, refers to a heterocyclyl group attached to the parent molecular moiety through an oxygen atom.

The term "heterocyclyloxyalkyl," as used herein, refers to an alkyl group substituted with one, two, or three heterocyclyloxy groups.

The term "heterocyclyloxycarbonyl," as used herein, refers to a heterocyclyloxy group attached to the parent molecular moiety through a carbonyl group.

The term "hydroxy," as used herein, refers to —OH.

The term "hydroxyalkyl," as used herein, refers to an alkyl group substituted with one, two, or three hydroxy groups.

The term "hydroxyalkylcarbonyl," as used herein, refers to a hydroxyalkyl group attached to the parent molecular moiety through a carbonyl group.

The term "nitro," as used herein, refers to —$NO_2$.

The term "—$NR^aR^b$" as used herein, refers to two groups, $R^a$ and $R^b$, which are attached to the parent molecular moiety through a nitrogen atom. $R^a$ and $R^b$ are independently selected from hydrogen, alkenyl, and alkyl.

The term "($NR^aR^b$)alkyl," as used herein, refers to an alkyl group substituted with one, two, or three —$NR^aR^b$ groups.

The term "($NR^aR^b$)carbonyl," as used herein, refers to an —$NR^aR^b$ group attached to the parent molecular moiety through a carbonyl group.

The term "—$NR^cR^d$," as used herein, refers to two groups, $R^c$ and $R^d$, which are attached to the parent molecular moiety through a nitrogen atom. $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, ($NR^eR^f$)alkyl, ($NR^eR^f$)alkylcarbonyl, ($NR^eR^f$)carbonyl, ($NR^eR^f$)sulfonyl, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro.

The term "($NR^cR^d$)alkenyl," as used herein, refers to an alkenyl group substituted with one, two, or three —$NR^cR^d$ groups.

The term "($NR^cR^d$)alkyl," as used herein, refers to an alkyl group substituted with one, two, or three —$NR^cR^d$ groups. The alkyl part of the ($NR^cR^d$)alkyl is further optionally substituted with one or two additional groups selected from alkoxy, alkoxyalkylcarbonyl, alkoxycarbonyl, alkylsulfanyl, arylalkoxyalkylcarbonyl, carboxy, heterocyclyl, heterocyclylcarbonyl, hydroxy, and ($NR^eR^f$)carbonyl; wherein the heterocyclyl is further optionally substituted with one, two, three, four, or five substituents independently selected from alkoxy, alkyl, cyano, halo, haloalkoxy, haloalkyl, and nitro.

The term "($NR^cR^d$)carbonyl," as used herein, refers to an —$NR^cR^d$ group attached to the parent molecular moiety through a carbonyl group.

The term "—$NR^eR^f$," as used herein, refers to two groups, $R^e$ and $R^f$, which are attached to the parent molecular moiety through a nitrogen atom. $R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, —($NR^XR^Y$)alkyl, and —($NR^XR^Y$)carbonyl.

The term "($NR^eR^f$)alkyl," as used herein, refers to an alkyl group substituted with one, two, or three —$NR^eR^f$ groups.

The term "($NR^eR^f$)alkylcarbonyl," as used herein, refers to an ($NR^eR^f$)alkyl group attached to the parent molecular moiety through a carbonyl group.

The term "($NR^eR^f$)carbonyl," as used herein, refers to an —$NR^eR^f$ group attached to the parent molecular moiety through a carbonyl group.

The term "($NR^eR^f$)sulfonyl," as used herein, refers to an —$NR^eR^f$ group attached to the parent molecular moiety through a sulfonyl group.

The term "—$NR^XR^Y$," as used herein, refers to two groups, $R^X$ and $R^Y$, which are attached to the parent molecular moiety through a nitrogen atom. $R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and ($NR^{X'}R^{Y'}$)carbonyl, wherein $R^{X'}$ and $R^{Y'}$ are independently selected from hydrogen and alkyl.

The term "($NR^XR^Y$)alkyl," as used herein, refers to an alkyl group substituted with one, two, or three —$NR^XR^Y$ groups.

The term "oxo," as used herein, refers to =O.

The term "sulfonyl," as used herein, refers to —$SO_2$—.

The term "trialkylsilyl," as used herein, refers to —$SiR_3$, wherein R is alkyl. The R groups may be the same or different The term "trialkylsilylalkyl," as used herein, refers to an alkyl group substituted with one, two, or three trialkylsilyl groups.

The term "trialkylsilylalkoxy," as used herein, refers to a trialkylsilylalkyl group attached to the parent molecular moiety through an oxygen atom.

The term "trialkylsilylalkoxyalkyl," as used herein, refers to an alkyl group substituted with one, two, or three trialkylsilylalkoxy groups.

Prodrugs

The term "prodrug" as used herein refers to any compound that when administered to a biological system generates a compound of the invention that inhibits Zika virus activity ("the active inhibitory compound"). The compound may be formed from the prodrug as a result of: (i) spontaneous chemical reaction(s), (ii) enzyme catalyzed chemical reaction(s), (iii) photolysis, and/or (iv) metabolic chemical reaction(s).

"Prodrug moiety" refers to a labile functional group which separates from the active inhibitory compound during metabolism, systemically, inside a cell, by hydrolysis, enzymatic cleavage, or by some other process (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191). Enzymes which are capable of an enzymatic activation mechanism with the prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

Exemplary prodrug moieties include the hydrolytically sensitive or labile acyloxymethyl esters —$CH_2OC(=O)R^{99}$ and acyloxymethyl carbonates —$CH_2OC(=O)OR^{99}$ where $R^{99}$ is $C_1$-$C_6$ alkyl, $C_1$-$C_6$ substituted alkyl, $C_6$-$C_{2M}$ aryl or $C_6$-$C_{20}$ substituted aryl. The acyloxyalkyl ester was first used as a prodrug strategy for carboxylic acids and then applied to phosphates and phosphonates by Farquhar et al. (1983) *J. Pharm. Sci.* 72: 324; also U.S. Pat. Nos. 4,816,570, 4,968,788, 5,663,159 and 5,792,756. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) —CH$_2$OC(=O)C(CH$_3$)$_3$. An exemplary acyloxymethyl carbonate prodrug moiety is pivaloyloxymethylcarbonate (POC) —CH$_2$OC(=O)OC(CH$_3$)$_3$.

Aryl esters of phosphorus groups, especially phenyl esters, are reported to enhance oral bioavailability (De Lombaert et al. (1994) *J. Med. Chem.* 37: 498). Phenyl esters containing a carboxylic ester ortho to a phosphate have also been described (Khamnei and Torrence, (1996) *J. Med. Chem.* 39:4109-4115). Benzyl esters are reported to generate parent phosphonic acids. In some cases, substituents at the ortho- or para-position may accelerate the hydrolysis. Benzyl analogs with an acylated phenol or an alkylated phenol may generate the phenolic compound through the action of enzymes, e.g., esterases, oxidases, etc., which in turn undergoes cleavage at the benzylic C—O bond to generate phosphoric acid and a quinone methide intermediate. Examples of this class of prodrugs are described by Mitchell et al. (1992) *J. Chem. Soc. Perkin Trans II.* 2345; Glazier WO 91/19721. Still other benzylic prodrugs have been described containing a carboxylic ester-containing group attached to the benzylic methylene (Glazier WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al. (1993) *Antiviral Res.,* 22: 155-174; Benzaria et al. (1996) *J. Med. Chem.* 39: 4958).

Protecting Groups

In the context of the present invention, protecting groups include prodrug moieties and chemical protecting groups.

"Protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. PGs do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene (John Wiley & Sons, Inc., New York, 1991, ISBN 0-471-62301-6) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below.

By way of example and not limitation, $R^1$, $R^3$, $R^{41}$, $R^{43}$, and $X^4$ are recursive substituents in certain embodiments. Typically, each of these may independently occur 20, 19, 18, 17, 16, 15, 14, 13, 12, 11, 10, 9, 8, 7, 6, 5, 4, 3, 2, 1, or 0, times in a given embodiment. More typically, each of these may independently occur 12 or fewer times in a given embodiment. Whenever a compound described herein is substituted with more than one of the same designated group, e.g., "$R^1$" or "$R^3$", then it will be understood that the groups may be the same or different, i.e., each group is independently selected. Wavy lines indicate the site of covalent bond attachments to the adjoining groups, moieties, or atoms.

In one embodiment of the invention, the compound is in an isolated and purified form. Generally, the term "isolated and purified" means that the compound is substantially free from biological materials (e.g. blood, tissue, cells, etc.). In one specific embodiment of the invention, the term means that the compound or conjugate of the invention is at least about 50 wt. % free from biological materials; in another specific embodiment, the term means that the compound or conjugate of the invention is at least about 75 wt. % free from biological materials; in another specific embodiment, the term means that the compound or conjugate of the invention is at least about 90 wt. % free from biological materials; in another specific embodiment, the term means that the compound or conjugate of the invention is at least about 98 wt. % free from biological materials; and in another embodiment, the term means that the compound or conjugate of the invention is at least about 99 wt. % free from biological materials. In another specific embodiment, the invention provides a compound or conjugate of the invention that has been synthetically prepared (e.g., ex vivo).

Stereoisomers

The compounds of the invention may have chiral centers, e.g., chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Salts and Hydrates

Examples of physiologically acceptable salts of the compounds of the invention include salts derived from an appropriate base, such as an alkali metal (for example, sodium), an alkaline earth metal (for example, magnesium), ammonium and $NX_4^+$ (wherein X is $C_1$-$C_4$ alkyl). Physiologically acceptable salts of a hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound of a hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds of the invention will typically be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the invention in their un-ionized, as well as zwitterionic form, and combinations with stoichiometric amounts of water as in hydrates.

Also included within the scope of this invention are the salts of the parental compounds with one or more amino acids. Any of the natural or unnatural amino acids are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Methods of Inhibition of Zika Virus

Another aspect of the invention relates to methods of inhibiting the activity of Zika virus comprising the step of treating a sample suspected of containing Zika virus with a compound or composition of the invention.

Compounds of the invention may act as inhibitors of Zika virus, as intermediates for such inhibitors or have other utilities as described below. The inhibitors will generally bind to locations on the surface or in a cavity of the liver. Compounds binding in the liver may bind with varying degrees of reversibility. Those compounds binding substantially irreversibly are ideal candidates for use in this method of the invention. Once labeled, the substantially irreversibly binding compounds are useful as probes for the detection of Zika virus. Accordingly, the invention relates to methods of detecting NS3 in a sample suspected of containing Zika virus comprising the steps of: treating a sample suspected of containing Zika virus with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl or amino. In one embodiment the invention provides a compound of formula (I) that comprises or that is bound or linked to one or more detectable labels. Within the context of the invention samples suspected of containing Zika virus include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing Zika virus. Samples can be contained in any medium including water and organic solvent/water mixtures. Samples include living organisms such as humans, and man made materials such as cell cultures.

The treating step of the invention comprises adding the compound of the invention to the sample or it comprises adding a precursor of the composition to the sample. The addition step comprises any method of administration as described above.

If desired, the activity of Zika virus after application of the compound can be observed by any method including direct and indirect methods of detecting Zika virus activity. Quantitative, qualitative, and semiquantitative methods of determining Zika virus activity are all contemplated. Typically one of the screening methods described above are applied, however, any other method such as observation of the physiological properties of a living organism are also applicable.

Many organisms contain Zika virus. The compounds of this invention are useful in the treatment or prophylaxis of conditions associated with Zika virus activation in animals or in man.

However, in screening compounds capable of inhibiting Zika virus activity it should be kept in mind that the results of enzyme assays may not always correlate with cell culture assays. Thus, a cell based assay should typically be the primary screening tool.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, PA). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of conditions associated with Zika virus activity.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provides compositions comprising one or more compounds of the invention formulated for sustained or controlled release.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

List of abbreviations and acronyms.

| Abbreviation | Definition |
|---|---|
| Ac | acetate |
| Ar | argon |
| ACN, $CH_3CN$, MeCN | acetonitrile |
| Boc | tert-butoxycarbonyl |
| cat | catalyst |
| $CS_2CO_3$ | Cesium carbonate |
| DCM | dichloromethane |
| DIPEA | N,N-diisopropylethy lamine |
| DMEM | Dulbecco's Modified Eagle Medium |
| DMSO | dimethylsulfoxide |
| DMF | dimethylformamide |
| EDTA | Ethylene diamine tetra acetic acid |
| ES/MS | electrospray mass spectrometry |
| Et | ethyl |
| $Et_3N$ | triethylamine |
| EtOAc | ethyl acetate |
| HATU | 1-[Bis(dimethylamino)methylene]-1H-1,2,3-triazolo[4,5-b] pyridinium 3-oxide hexafluorophosphate, Hexafluorophosphate Azabenzotriazole Tetramethyl Uronium) |

| Abbreviation | Definition |
| --- | --- |
| HCl | hydrochloric acid |
| HPLC | high performance liquid chromatography |
| iPr | isopropyl |
| iPrOH | Isopropyl alcohol |
| $K_2CO_3$ | Potassium carbonate |
| LC | liquid chromatography |
| Me | methyl |
| MeOH | methanol |
| Moc-L-valine | (S)-2-((Methoxycarbonyl)amino)-3-methylbutanoic acid |
| m/z | mass to charge ratio |
| NBS | N-Bromosuccinimide |
| NCS | N-Chlorosuccinimide |
| $NH_4OAc$ | Ammonium Acetate |
| NMP | N-methyl-2-pyrrolidone |
| NMR | Nuclear Magnetic Resonance |
| Palau'Chlor | 2-Chloro-1,3-bis(methoxycarbonyl)guanidine |
| Ph | phenyl |
| Pd(dppf)$Cl_2$ | [1,1'-Bis(diphenylphosphino)ferrocene]dichloropalladium(II) |
| Pd(OAc)$_2$ | Palladium (II) Acetate |
| Pr | propyl |
| RP | reverse phase |
| $SiO_2$ | Silicon dioxide |
| TFA | trifluoroacetic acid |
| THF | tetrahydrofuran |
| TBHP | tert-butyl hydroperoxide |
| δ | parts per million referenced to residual non-deuterated solvent peak |
| ZIKV | Zika virus |

EXAMPLE PROCEDURES AND COMPOUND EXAMPLES

Procedure 1 Example 24

Methyl ((S)-1-((2S,5S)-2-(4-chloro-5-(2-((2S,5S)-5-methyl-1-((S)-4,4,4-trifluoro-2-((methoxycarbonyl)amino)-3,3-dimethylbutanoyl)pyrrolidin-2-yl)-1,11-dihydroisochromeno[4',3':6,7]naphtho[1,2-d]imidazol-9-yl)-1H-imidazol-2-yl)-5-methylpyrrolidin-1-yl)-4,4,4-trifluoro-3,3-dimethyl-1-oxobutan-2-yl)carbamate

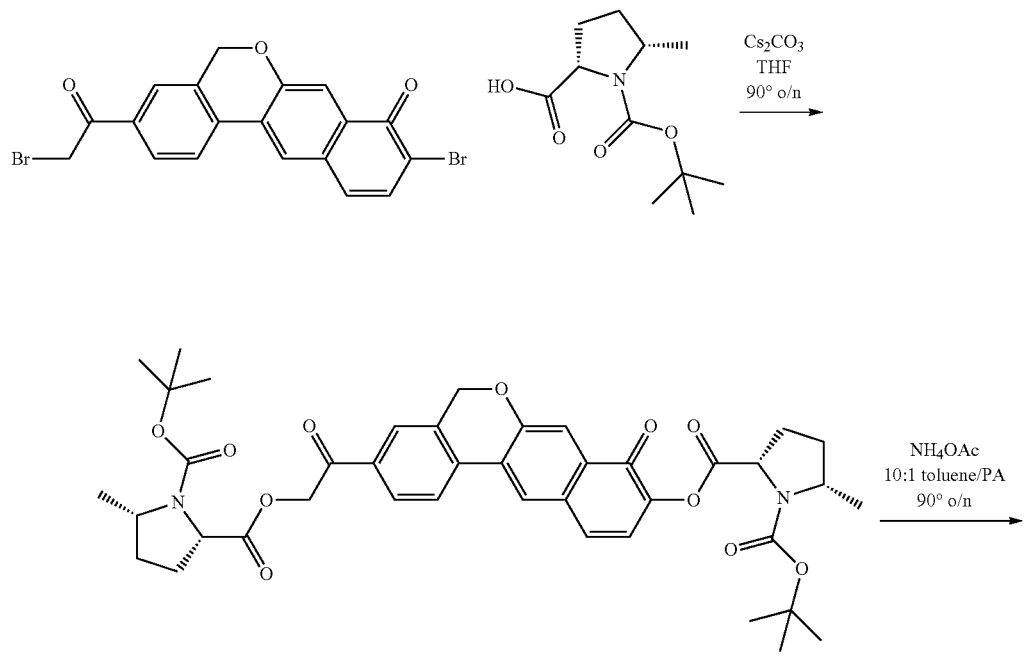

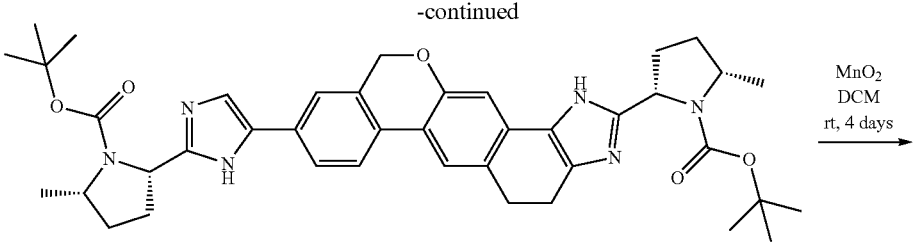

MnO₂
DCM
rt, 4 days

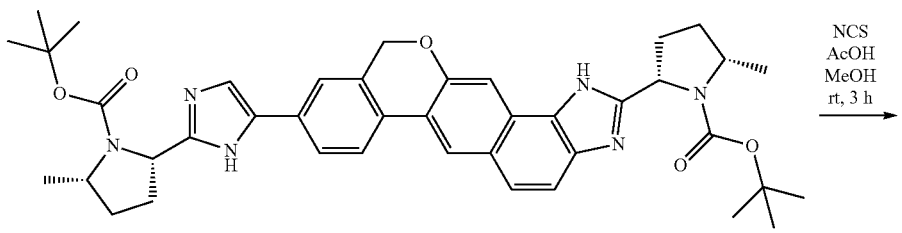

NCS
AcOH
MeOH
rt, 3 h

1. HCl (4M in dioxane)
   4:1 DCM/MeOH, 40°
   5 h
2. HATU, DIPEA rt o/n

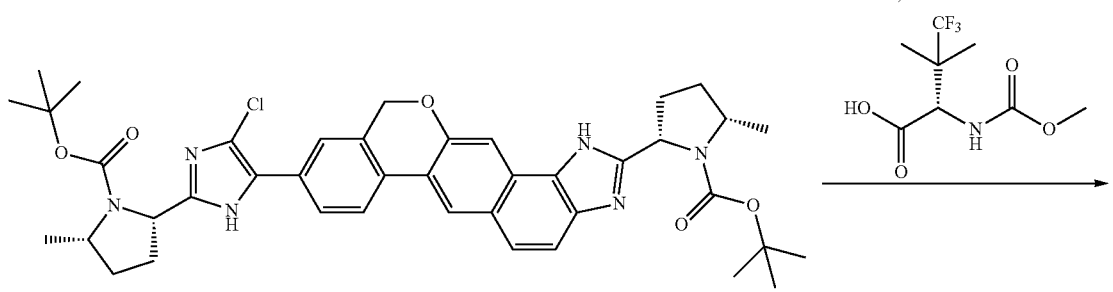

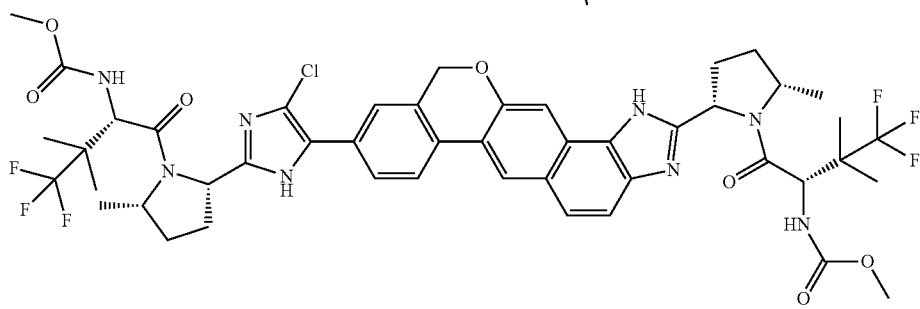

2-(2-(9-(((2S,4S)-1-(tert-butoxycarbonyl)-4-methylpyrrolidine-2-carbonyl)oxy)-8-oxo-8,9,10,11-tetrahydro-5H-dibenzo[c,g]chromen-3-yl)-2-oxoethyl) 1-(tert-butyl) (2S,5S)-5-methylpyrrolidine-1,2-dicarboxylate A suspension of 9-bromo-3-(2-bromoacetyl)-10,11-dihydro-5H-dibenzo[c,g]chromen-8(9H)-one (5 g, 11.11 mmol), (2S,5S)-1-(tert-butoxycarbonyl)-5-methylpyrrolidine-2-carboxylic acid (6.37 g, 27.77 mmol), and cesium carbonate (4.52 g, 13.89 mmol) in THF (100 mL) was heated at 40 deg for 24 hr. The reaction was quenched with 75 mL EtOAc and 60 mL water. The brown solution was partitioned. Added 50 mL 1N HCl. The aqueous was back extracted with EtOAc 2×40 mL. The combined organics were dried over sodium sulfate.

ES/MS: 746.7 (M⁺).

tert-butyl (2S,5S)-2-(5-(2-((2S,5S)-1-(tert-butoxycarbonyl)-5-methylpyrrolidin-2-yl)-1,4,5,11-tetrahydroisochromeno[4',3':6,7]naphtho[1,2-d]imidazol-9-yl)-1H-imidazol-2-yl)-5-methylpyrrolidine-1-carboxylate A suspension of 2-(2-(9-(((2S,4S)-1-(tert-butoxycarbonyl)-4-methylpyrrolidine-2-carbonyl)oxy)-8-oxo-8,9,10,11-tetrahydro-5H-dibenzo[c,g]chromen-3-yl)-2-oxoethyl) 1-(tert-butyl) (2s,5s)-5-methylpyrrolidine-1,2-dicarboxylate (8.3 g, 11.11 mmol) and ammonium acetate (17.12 g, 222.16 mmol) in toluene (100 mL) and isopropanol (10 mL), was heated at 90 deg o/n. The reaction was partitioned with water. The aqueous was back extracted with EtOAc. The combined organics were transferred to a 500 mL rb with 30 mL MeOH. Added 5 g Celite, 25 mL brine and slowly, 13 mL of 6N NaOH (~6 eq). Stirred for 30 min, then filtered through a plug of Celite. Rinsed with toluene and IPA (50 mL). Separated organic extract, washed with water. Organic extract was dried over sodium sulfate and purified by normal phase SiO$_2$ chromatography (eluent: ethyl acetate/DCM) to provide the desired product.

ES/MS: 707.3 (M$^+$).

1H NMR (400 MHz, Chloroform-d) δ 10.57 (d, J=106.4 Hz, 2H), 7.88-7.39 (m, 5H), 6.75 (s, 1H), 5.13 (d, J=10.6 Hz, 3H), 5.07-4.80 (m, 3H), 3.96 (s, 4H), 3.02 (s, 3H), 2.86 (s, 6H), 2.03 (s, 12H), 1.99-1.73 (m, 4H), 1.50 (d, J=5.3 Hz, 31H), 1.30-1.04 (m, 15H).

tert-butyl (2S,5S)-2-(5-(2-((2S,5S)-1-(tert-butoxycarbonyl)-5-methylpyrrolidin-2-yl)-1,11-dihydroisochromeno[4',3':6,7]naphtho[1,2-d]imidazol-9-yl)-1H-imidazol-2-yl)-5-methylpyrrolidine-1-carboxylate To a solution of tert-butyl (2S,5S)-2-(5-(2-((2S,5S)-1-(tert-butoxycarbonyl)-5-methylpyrrolidin-2-yl)-1,4,5,11-tetrahydroisochromeno[4',3':6,7]naphtho[1,2-d]imidazol-9-yl)-1H-imidazol-2-yl)-5-methylpyrrolidine-1-carboxylate (4.51 g, 6.38 mmol) in DCM (60 mL), was added manganese dioxide (16.63 g, 191.32 mmol). The reaction was stirred at rt for 4 days, open to air. Added 150 mL DCM and 30 g Celite. Filtered through Celite plug. Concentrated to give the desired product.

ES/MS: 705.3 (M$^+$).

1H NMR (400 MHz, Chloroform-d) δ 8.24 (s, 1H), 7.74 (d, J=90.6 Hz, 8H), 5.25 (d, J=35.1 Hz, 5H), 4.99 (d, J=7.4 Hz, 2H), 4.00 (s, 4H), 2.42-2.09 (m, 7H), 1.89 (s, 3H), 1.52 (d, J=10.1 Hz, 38H), 1.14 (d, J=68.3 Hz, 17H).

tert-butyl (2S,5S)-2-(5-(2-((2S,5S)-1-(tert-butoxycarbonyl)-5-methylpyrrolidin-2-yl)-1,11-dihydroisochromeno[4',3':6,7]naphtho[1,2-d]imidazol-9-yl)-4-chloro-1H-imidazol-2-yl)-5-methylpyrrolidine-1-carboxylate To a suspension of tert-butyl (2S,5S)-2-(5-(2-((2S,5S)-1-(tert-butoxycarbonyl)-5-methylpyrrolidin-2-yl)-1,11-dihydroisochromeno[4',3':6,7]naphtho[1,2-d]imidazol-9-yl)-1H-imidazol-2-yl)-5-methylpyrrolidine-1-carboxylate (999.3 mg, 1.418 mmol) in MeOH (40 mL), was added AcOH (0.05 ml, 0.873 mmol) and n-chlorosuccinimide (208.9 mg, 1.564 mmol). The orange solution was stirred at rt o/n. The reaction was diluted with DCM and washed with sat'd NaHCO3 solution and dried with sodium sulfate. Purification by normal phase SiO$_2$ chromatography (eluent: ethyl acetate/DCM) to provide the desired product.

ES/MS: 739.2 (M$^+$).

1H NMR (400 MHz, Methanol-d4) δ 8.43 (s, 1H), 7.79 (d, J=8.4 Hz, 1H), 7.72 (d, J=8.9 Hz, 1H), 7.60 (s, 1H), 5.48 (s, 4H), 5.23 (s, 2H), 5.10 (s, 3H), 4.09 (q, J=7.1 Hz, 1H), 4.02 (s, 1H), 2.68 (s, 1H), 2.38 (s, 2H), 2.24 (s, 4H), 2.00 (s, 1H), 1.77 (s, 2H), 1.48 (d, J=5.5 Hz, 5H), 1.41 (d, J=6.4 Hz, 4H), 1.32 (s, 16H), 1.23 (t, J=7.1 Hz, 1H).

methyl ((S)-1-((2S,5S)-2-(4-chloro-5-(2-((2S,5S)-5-methyl-1-((S)-4,4,4-trifluoro-2-((methoxycarbonyl)amino)-3,3-dimethylbutanoyl)pyrrolidin-2-yl)-1,11-dihydroisochromeno[4',3':6,7]naphtho[1,2-d]imidazol-9-yl)-1H-imidazol-2-yl)-5-methylpyrrolidin-1-yl)-4,4,4-trifluoro-3,3-dimethyl-1-oxobutan-2-yl)carbamate To a solution of tert-butyl (2S,5S)-2-(5-(2-((2S,5S)-1-(tert-butoxycarbonyl)-5-methylpyrrolidin-2-yl)-1,11-dihydroisochromeno[4',3':6,7]naphtho[1,2-d]imidazol-9-yl)-4-chloro-1H-imidazol-2-yl)-5-methylpyrrolidine-1-carboxylate (50.1 mg, 0.068 mmol) in methyl ((S)-1-((2S,5S)-2-(5-(2-((2S,5S)-1-((methoxycarbonyl)-L-valyl)-5-methylpyrrolidin-2-yl)-1,11-dihydroisochromeno[4',3':6,7]naphtho[1,2-d]imidazol-9-yl)-1H-imidazol-2-yl)-5-methylpyrrolidin-1-yl)-3-methyl-1-oxobutan-2-yl)carbamateDCM (4 mL) and MeOH (1 mL), was added 4M hydrochloric acid (4M in dioxane) (0.475 ml). The reaction was heated to 40 deg for 4 hr. The reaction was concentrated to dryness.

To a solution of hydrochloric acid salt (41.47 mg, 0.068 mmol), moc-trifluoro-L-tert-leucine (34.6 mg, 0.142 mmol), and HATU (55.5 mg, 0.146 mmol) in DMF (1.5 mL), was added N,N-diisopropylethylamine (120 µl, 0.689 mmol). Stirred at rt o/n. The reaction mixture cooled to 0 degrees and 0.2 mL TFA was added. Purified by RP-HPLC (eluent: water/MeCN*0.1% TFA) to yield product as a bis-trifluoroacetate salt.

ES/MS: 989.4 (M$^+$).

1H NMR (400 MHz, Methanol-d4) δ 8.58 (d, J=2.4 Hz, 1H), 8.11 (t, J=7.8 Hz, 1H), 8.02-7.80 (m, 3H), 7.69-7.57 (m, 3H), 7.48 (dd, J=26.1, 11.1 Hz, 1H), 5.33-5.20 (m, 4H), 5.01-4.92 (m, 1H), 4.78-4.57 (m, 2H), 3.68 (d, J=8.1 Hz, 5H), 3.57 (s, 1H), 3.28 (s, 1H), 2.61-2.24 (m, 5H), 2.20-1.98 (m, 2H), 1.92 (dd, J=12.4, 6.4 Hz, 1H), 1.66 (d, J=6.6 Hz, 3H), 1.56 (d, J=6.6 Hz, 3H), 1.51-1.35 (m, 1H), 1.40-1.27 (m, 5H), 1.24 (q, J=7.7, 7.3 Hz, 7H), 1.08 (d, J=7.3 Hz, 5H).

Procedure 2 Example 10

Methyl ((S)-2-((2S,5S)-2-(4-bromo-5-(2-((2S,5S)-1-((S)-2-((2R,6R)-2,6-dimethyltetrahydro-2H-pyran-4-yl)-2-((methoxycarbonyl)amino)acetyl)-5-methylpyrrolidin-2-yl)-1,11-dihydroisochromeno[4',3':6,7]naphtho[1,2-d]imidazol-9-yl)-1H-imidazol-2-yl)-5-methylpyrrolidin-1-yl)-1-((2R,6R)-2,6-dimethyltetrahydro-2H-pyran-4-yl)-2-oxoethyl)carbamate

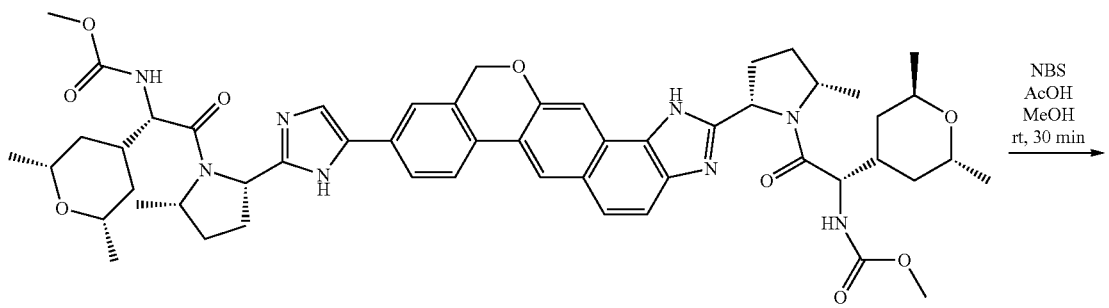

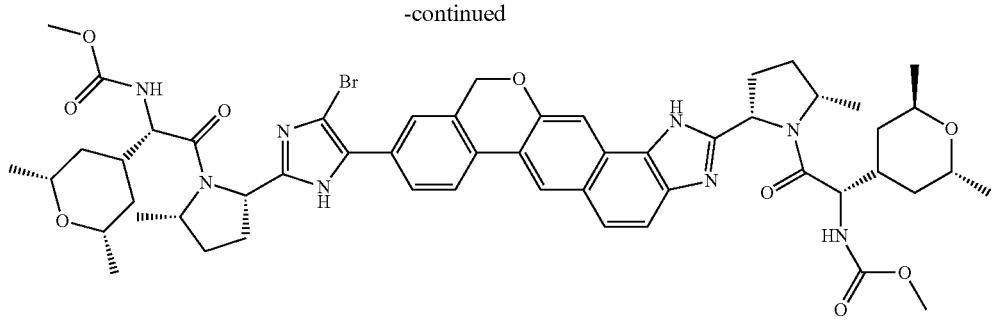

A solution of methyl ((S)-1-((2R,6R)-2,6-dimethyltetrahydro-2H-pyran-4-yl)-2-((2S,5S)-2-(5-(2-((2S,5S)-1-((S)-2-((2R,6R)-2,6-dimethyltetrahydro-2H-pyran-4-yl)-2-((methoxycarbonyl)amino)acetyl)-5-methylpyrrolidin-2-yl)-1,11-dihydroisochromeno[4',3':6,7]naphtho[1,2-d]imidazol-9-yl)-1H-imidazol-2-yl)-5-methylpyrrolidin-1-yl)-2-oxoethyl)carbamate (80.0 mg, 0.0834 mmol), n-bromosuccinimide (18.0 mg, 0.101 mmol), and acetic acid (2.5 mg, 0.0417 mmol) in methanol (1 mL) was stirred at room temperature for 30 min. Purified by RP-HPLC (eluent: water/MeCN*0.1% TFA) to yield product as a trifluoroacetate salt.

ES/MS: 1038.9 (M+).

1H NMR (400 MHz, Methanol-d4) δ 8.59 (dd, J=8.4, 3.5 Hz, 1H), 8.16-7.97 (m, 2H), 7.94-7.76 (m, 2H), 7.70-7.57 (m, 2H), 5.29 (dt, J=11.1, 5.3 Hz, 3H), 5.00 (dd, J=9.9, 7.6 Hz, 1H), 4.81-4.67 (m, 1H), 4.42-4.02 (m, 4H), 3.79 (d, J=8.9 Hz, OH), 3.71-3.58 (m, 5H), 3.52 (q, J=14.0, 10.4 Hz, 1H), 2.90-2.74 (m, 1H), 2.68-1.84 (m, 7H), 1.80-1.34 (m, 8H), 1.33-1.02 (m, 13H), 1.00-0.82 (m, 3H).

Procedure 3 Example 33

Methyl ((S)-1-((2S,5S)-2-(4-fluoro-5-(2-((2S,5S)-1-((methoxycarbonyl)-L-valyl)-5-methylpyrrolidin-2-yl)-1,11-dihydroisochromeno[4',3':6,7]naphtho[1,2-d]imidazol-9-yl)-1H-imidazol-2-yl)-5-methylpyrrolidin-1-yl)-3-methyl-1-oxobutan-2-yl)carbamate

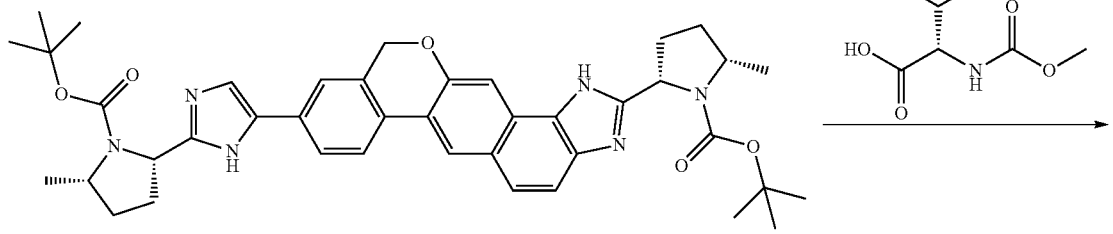

1. HCl (4M in dioxane)
   4:1 DCM/MeOH, 40°
   5 h
2. HATU, DIPEA rt o/n

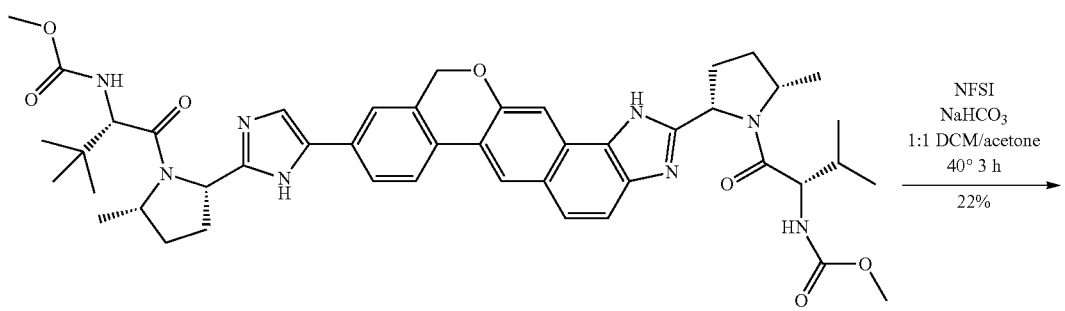

NFSI
NaHCO₃
1:1 DCM/acetone
40° 3 h
22%

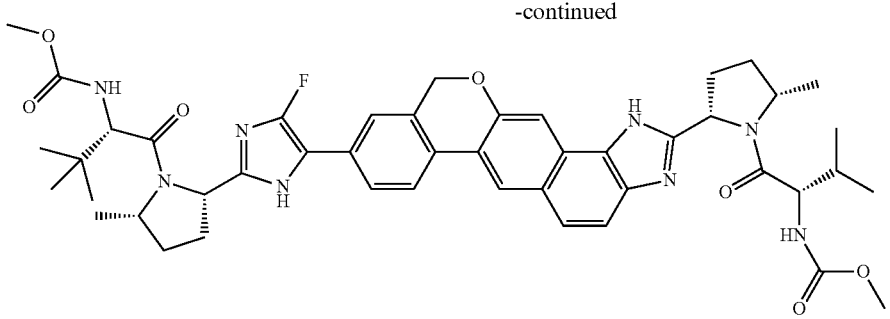

Methyl ((S)-1-((2S,5S)-2-(5-(2-((2S,5S)-1-((methoxycarbonyl)-L-valyl)-5-methylpyrrolidin-2-yl)-1,11-dihydroisochromeno[4',3':6,7]naphtho[1,2-d]imidazol-9-yl)-1H-imidazol-2-yl)-5-methylpyrrolidin-1-yl)-3-methyl-1-oxobutan-2-yl) carbamate To a solution of tert-butyl (2S,5S)-2-(5-(2-((2S,5S)-1-(tert-butoxycarbonyl)-5-methylpyrrolidin-2-yl)-1,11-dihydroisochromeno[4',3':6,7]naphtho[1,2-d]imidazol-9-yl)-1H-imidazol-2-yl)-5-methylpyrrolidine-1-carboxylate (100.1 mg, 0.142 mmol) in DCM (8 mL) and MeOH (2 mL), was added 4M hydrochloric acid (4M in dioxane) (1.0 ml). The reaction was heated to 40 deg for 3 hr. The reaction was concentrated to dryness.

To a solution of hydrochloride salt (82.02 mg, 0.142 mmol), Moc-L-valine (52.8 mg, 0.301 mmol), and HATU (113.4 mg, 0.298 mmol) in DMF (2.0 mL), was added N,N-diisopropylethylamine (250 µl, 1.435 mmol). Stirred at rt o/n. Reaction mixture cooled to 0 degrees and 0.2 mL TFA was added. Purified by RP-HPLC (eluent: water/MeCN*0.1% TFA) to yield product as a bis-trifluoroacetate salt.

The product was washed with sodium bicarbonate and diluted with ethyl acetate, organic layer dried over sodium sulfate and concentrated to dryness to give desired product.

ES/MS: 819.5 (M$^+$).

1H NMR (400 MHz, Methanol-d4) δ 8.33 (t, J=14.8 Hz, 2H), 8.10 (s, 1H), 8.00-7.86 (m, 2H), 7.74-7.55 (m, 4H), 7.51 (s, 2H), 7.34 (d, J=7.0 Hz, 1H), 5.60 (s, 1H), 5.37 (s, 2H), 5.29-5.04 (m, 7H), 4.74 (dt, J=13.7, 6.9 Hz, 1H), 4.24 (dq, J=20.0, 7.1 Hz, 2H), 4.16-4.02 (m, 3H), 3.88 (s, 2H), 3.73-3.60 (m, 8H), 2.33 (dt, J=13.6, 7.3 Hz, 1H), 2.19-1.99 (m, 2H), 2.00 (s, 2H), 1.97 (s, 2H), 1.56 (d, J=6.6 Hz, 3H), 1.48 (d, J=6.6 Hz, 4H), 1.32-1.18 (m, 4H), 1.10 (s, 19H), 1.08-0.90 (m, 13H), 0.86 (s, 1H), 0.84 (s, 8H).

Methyl ((S)-1-((2S,5S)-2-(4-fluoro-5-(2-((2S,5S)-1-((methoxycarbonyl)-L-valyl)-5-methylpyrrolidin-2-yl)-1,11-dihydroisochromeno[4',3':6,7]naphtho[1,2-d]imidazol-9-yl)-1H-imidazol-2-yl)-5-methylpyrrolidin-1-yl)-3-methyl-1-oxobutan-2-yl) carbamate To a slurry of methyl ((S)-1-((2S,5S)-2-(5-(2-((2S,5S)-1-((methoxycarbonyl)-L-valyl)-5-methylpyrrolidin-2-yl)-1,11-dihydroisochromeno[4',3':6,7]naphtho[1,2-d]imidazol-9-yl)-1H-imidazol-2-yl)-5-methylpyrrolidin-1-yl)-3-methyl-1-oxobutan-2-yl)carbamate (61.8 mg, 0.075 mmol) and NaHCO3 (9.9 mg, 0.228 mmol) in DCM/acetone(1 mL each), was added N-fluorobenzenesulfonimide (26.18 mg, 0.083 mmol). Stirred at 40 degrees for 1.5 hr. The reaction mixture was cooled to 0 degrees and 10 drops of TFA were added. Purified by RP-HPLC (eluent: water/MeCN*0.1% TFA) to yield product as a bis-trifluoroacetate salt.

ES/MS: 837.4 (M$^+$).

1H NMR (400 MHz, Methanol-d4) δ 8.58 (d, J=9.8 Hz, 1H), 8.21 (d, J=4.8 Hz, OH), 8.06 (dd, J=19.4, 8.2 Hz, 2H), 7.90 (d, J=12.6 Hz, 1H), 7.70-7.58 (m, 2H), 7.47 (s, 1H), 5.87 (s, OH), 5.39 (d, J=6.8 Hz, OH), 5.28 (d, J=6.1 Hz, 3H), 4.32 (s, OH), 4.22 (d, J=8.0 Hz, 1H), 4.14 (d, J=8.9 Hz, 1H), 4.05 (d, J=9.4 Hz, 1H), 3.79 (s, 2H), 3.66 (d, J=6.4 Hz, 4H), 2.81 (s, OH), 2.69 (d, J=9.4 Hz, OH), 2.65-2.55 (m, 1H), 2.40 (s, 3H), 2.39-2.24 (m, 1H), 2.17-2.07 (m, OH), 2.08-1.88 (m, 2H), 1.63 (d, J=6.8 Hz, 3H), 1.50 (d, J=6.6 Hz, 2H), 1.27 (d, J=6.4 Hz, 1H), 1.19 (d, J=6.3 Hz, 1H), 1.05 (dd, J=26.3, 6.7 Hz, 4H), 0.95 (t, J=7.2 Hz, 4H), 0.85 (dd, J=6.8, 3.3 Hz, 4H), 0.09 (d, J=2.2 Hz, OH).

Procedure 4 Example 31

Methyl ((S)-1-((2S,5S)-2-(4-bromo-5-(2-((2S,5S)-5-methyl-1-(propionyl-L-valyl)pyrrolidin-2-yl)-1,11-dihydroisochromeno[4',3':6,7]naphtho[1,2-d]imidazol-9-yl)-1H-imidazol-2-yl)-5-methylpyrrolidin-1-yl)-3-methyl-1-oxobutan-2-yl)carbamate

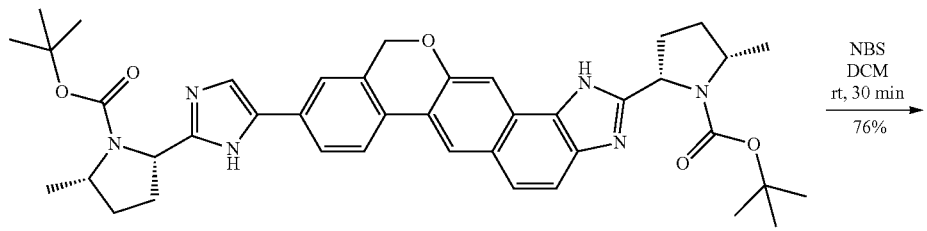

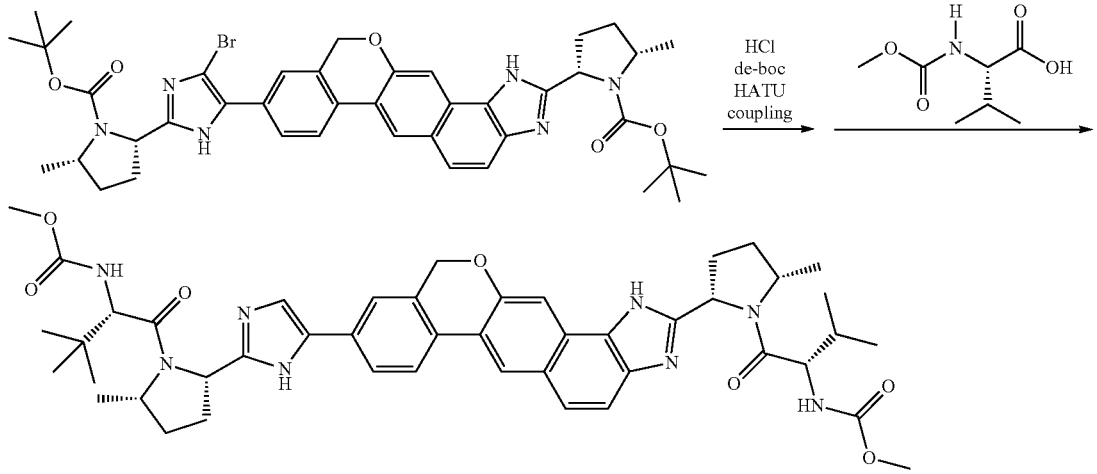

tert-butyl (2S,5S)-2-(9-(4-bromo-2-((2S,5S)-1-(tert-butoxycarbonyl)-5-methylpyrrolidin-2-yl)-1H-imidazol-5-yl)-1,11-dihydroisochromeno[4',3':6,7]naphtho[1,2-d]imidazol-2-yl)-5-methylpyrrolidine-1-carboxylate To a slurry of tert-butyl (2S,5S)-2-(5-(2-((2S,5S)-1-(tert-butoxycarbonyl)-5-methylpyrrolidin-2-yl)-1,11-dihydroisochromeno[4',3':6,7]naphtho[1,2-d]imidazol-9-yl)-1H-imidazol-2-yl)-5-methylpyrrolidine-1-carboxylate (500.3 mg, 0.710 mmol) in DCM (20 mL) at 0 degrees, was added N-bromosuccinimide (138.9 mg, 0.780 mmol). The reaction was gradually warmed to rt and stirred for 30 min. The reaction was diluted with EtOAc and washed with sat'd NaHCO3 solution. The organic extract was dried over sodium sulfate and purified by normal phase SiO$_2$ chromatography (eluent: ethyl acetate/hexane) to provide the desired product.

ES/MS: 785.2 (M$^+$).

1H NMR (400 MHz, Methanol-d4) δ 8.43 (s, OH), 8.06 (d, J=8.3 Hz, OH), 7.96 (s, 1H), 7.79 (d, J=8.2 Hz, OH), 7.72 (d, J=8.9 Hz, OH), 7.58 (d, J=15.7 Hz, 1H), 5.23 (s, 1H), 5.09 (s, 1H), 4.09 (q, J=7.1 Hz, 3H), 3.34 (s, 2H), 2.67 (s, 1H), 2.38 (s, OH), 2.24 (s, 1H), 2.25-2.17 (m, OH), 2.00 (s, 4H), 1.76 (s, 1H), 1.44 (dd, J=29.0, 6.4 Hz, 3H), 1.36-1.19 (m, 16H), 0.93-0.82 (m, 2H).

methyl ((s)-1-((2S,5S)-2-(4-bromo-5-(2-((2S,5S)-5-methyl-1-(propionyl-L-valyl)pyrrolidin-2-yl)-1,11-dihydroisochromeno[4',3':6,7]naphtho[1,2-d]imidazol-9-yl)-1H-imidazol-2-yl)-5-methylpyrrolidin-1-yl)-3-methyl-1-oxobutan-2-yl)carbamate To a solution of tert-butyl (2S,5S)-2-(9-(4-bromo-2-((2S,5S)-1-(tert-butoxycarbonyl)-5-methylpyrrolidin-2-yl)-1H-imidazol-5-yl)-1,11-dihydroisochromeno[4',3':6,7]naphtho[1,2-d]imidazol-2-yl)-5-methylpyrrolidine-1-carboxylate (32.6 mg, 0.042 mmol) in DCM (4 mL) and MeOH (1 mL), was added 4M hydrochloric acid (4M in dioxane) (0.300 ml). The reaction was heated to 40 deg for 5 hr. The reaction was concentrated to dryness. Carried onto step below, assume 100% yield.

To a solution of hydrochloride salt (27.30 mg, 0.045 mmol), Moc-L-valine (17.9 mg, 0.095 mmol), and HATU (36.4 mg, 0.096 mmol) in DMF (1.5 mL), was added N,N-diisopropylethylamine (80 μl, 0.459 mmol). Stirred at rt o/n. The reaction mixture cooled to 0 degrees and 0.2 mL TFA was added. Purified by RP-HPLC (eluent: water/MeCN*0.1% TFA) to yield product as a bis-trifluoroacetate salt.

ES/MS: 899.3 (M$^+$).

1H NMR (400 MHz, Methanol-d4) δ 8.62 (d, J=6.0 Hz, 1H), 8.15-7.96 (m, 3H), 7.92-7.83 (m, 1H), 7.67 (s, 1H), 7.71-7.59 (m, 1H), 5.31 (d, J=4.3 Hz, 3H), 5.05-4.96 (m, 1H), 4.23 (dd, J=12.8, 5.7 Hz, 1H), 4.21-4.11 (m, 1H), 4.07 (d, J=9.4 Hz, 1H), 3.79 (d, J=4.4 Hz, 1H), 3.72-3.63 (m, 6H), 2.79 (s, 1H), 2.68-2.55 (m, 1H), 2.45 (s, 3H), 2.34 (dtt, J=20.5, 13.0, 6.2 Hz, 2H), 2.20-2.04 (m, 1H), 2.04 (s, 3H), 1.94 (ddd, J=18.5, 11.3, 4.9 Hz, 2H), 1.63 (d, J=6.7 Hz, 3H), 1.51 (d, J=6.7 Hz, 2H), 1.28 (d, J=6.2 Hz, 1H), 1.20 (d, J=6.2 Hz, 2H), 1.12-0.91 (m, 10H), 0.89-0.82 (m, 5H).

Procedure 5 Example 43

Methyl ((S)-1-((2S,5S)-2-(4-isopropyl-5-(2-((2S,5S)-1-((methoxycarbonyl)-L-valyl)-5-methylpyrrolidin-2-yl)-1,11-dihydroisochromeno[4',3':6,7]naphtho[1,2-d]imidazol-9-yl)-1H-imidazol-2-yl)-5-methylpyrrolidin-1-yl)-3-methyl-1-oxobutan-2-yl)carbamate

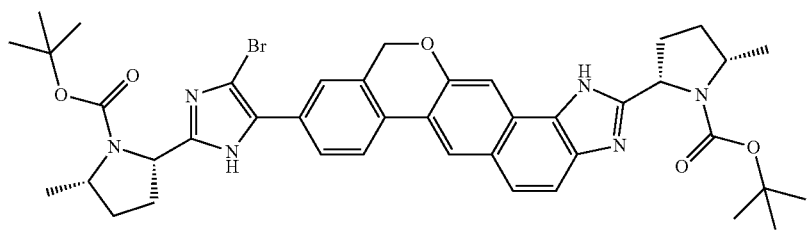

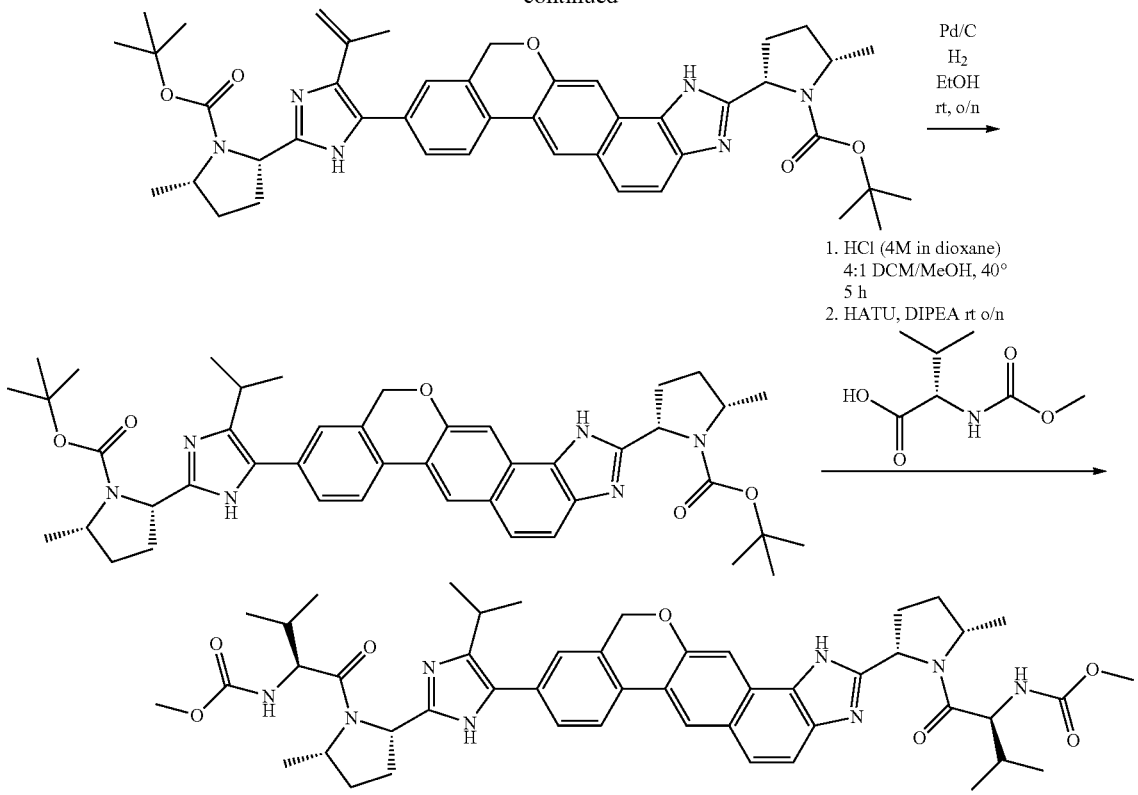

tert-butyl (2S,5S)-2-(5-(2-((2S,5S)-1-(tert-butoxycarbonyl)-5-methylpyrrolidin-2-yl)-1,11-dihydroisochromeno[4',3':6,7]naphtho[1,2-d]imidazol-9-yl)-4-(prop-1-en-2-yl)-1H-imidazol-2-yl)-5-methylpyrrolidine-1-carboxylate A solution of tert-butyl (2S,5S)-2-(9-(4-bromo-2-((2S, 5S)-1-(tert-butoxycarbonyl)-5-methylpyrrolidin-2-yl)-1H-imidazol-5-yl)-1,11-dihydroisochromeno[4',3':6,7]naphtho [1,2-d]imidazol-2-yl)-5-methylpyrrolidine-1-carboxylate (323.1 mg, 0.412 mmol), Isopropenylboronic acid pinacol ester 95% (310 μl, 1.649 mmol), Palladium acetate (9.5 mg, 0.042 mmol), Butyldi-1-adamantylphosphine min. 95% (29.8 mg, 0.083 mmol) and Potassium carbonate (228.9 mg, 1.656 mmol) in dioxane (12.8 mL) and water (6.4 mL) was degassed with argon for 10 min, then heated at 100 deg o/n. The reaction was diluted with EtOAc and washed with brine. The organic extract was dried over sodium sulfate and purified by normal phase $SiO_2$ chromatography (eluent: ethyl acetate/DCM) to provide the desired product.

ES/MS: 745.5 (M+).

1H NMR (400 MHz, Methanol-d4) δ 8.39 (s, 1H), 7.97 (d, J=8.1 Hz, 1H), 7.84 (s, 1H), 7.69 (d, J=8.8 Hz, 1H), 7.62-7.52 (m, 2H), 7.42 (s, 1H), 5.19 (s, 2H), 4.87 (s, 5H), 4.80 (s, 1H), 4.09 (q, J=7.1 Hz, 2H), 4.01 (s, 1H), 2.37 (s, 1H), 2.25 (s, 4H), 2.26-2.09 (m, 1H), 2.01 (d, J=7.2 Hz, 4H), 1.78-1.69 (m, 2H), 1.44 (dd, J=27.3, 6.2 Hz, 6H), 1.37-1.30 (m, 17H), 1.29-1.16 (m, 2H).

tert-butyl (2S,5S)-2-(5-(2-((2S,5S)-1-(tert-butoxycarbonyl)-5-methylpyrrolidin-2-yl)-1,11-dihydroisochromeno[4',3':6,7]naphtho[1,2-d]imidazol-9-yl)-4-isopropyl-1H-imidazol-2-yl)-5-methylpyrrolidine-1-carboxylate A solution of tert-butyl (2S,5S)-2-(5-(2-((2S,5S)-1-(tert-butoxycarbonyl)-5-methylpyrrolidin-2-yl)-1,11-dihydroisochromeno[4',3':6,7]naphtho[1,2-d]imidazol-9-yl)-4-(prop-1-en-2-yl)-1H-imidazol-2-yl)-5-methylpyrrolidine-1-carboxylate (266.1 mg, 344 μmol) in EtOH (15 mL) was degassed with Ar/Vac 3×. Added Pd/C (10%, 19 mg, 17.85 μmol) and stirred at rt with a balloon of hydrogen overnight. The reaction was filtered over a Celite plug and rinsed with DCM. Concentrated and carried onto next step without purification

ES/MS: 747.3 (M+).

1H NMR (400 MHz, Methanol-d4) δ 8.40 (s, 1H), 8.01 (d, J=8.2 Hz, 1H), 7.92 (s, 1H), 7.70 (d, J=8.9 Hz, 1H), 7.60-7.51 (m, 2H), 7.36 (d, J=1.5 Hz, 1H), 5.21 (s, 2H), 5.07 (s, 1H), 4.09 (s, 1H), 4.02 (s, 1H), 3.60 (q, J=7.0 Hz, 5H), 3.27 (t, J=6.8 Hz, OH), 2.37 (d, J=7.8 Hz, 1H), 2.29 (s, 2H), 2.21 (s, 2H), 2.26-2.05 (m, 1H), 1.45 (dd, J=23.7, 6.3 Hz, 6H), 1.36-1.22 (m, 7H), 1.17 (t, J=7.1 Hz, 10H).

methyl ((s)-1-((2S,5S)-2-(4-isopropyl-5-(2-((2S,5S)-1-((methoxycarbonyl)-L-valyl)-5-methylpyrrolidin-2-yl)-1,11-dihydroisochromeno[4',3':6,7]naphtho[1,2-d]imidazol-9-yl)-1H-imidazol-2-yl)-5-methylpyrrolidin-1-yl)-3-methyl-1-oxobutan-2-yl) carbamate To a solution of tert-butyl (2S,5S)-2-(5-(2-((2S,5S)-1-(tert-butoxycarbonyl)-5-methylpyrrolidin-2-yl)-1,11-dihydroisochromeno[4',3':6,7]naphtho[1,2-d]imidazol-9-yl)-4-isopropyl-1H-imidazol-2-yl)-5-methylpyrrolidine-1-carboxylate (50.6 mg, 0.068 mmol) in DCM (4 mL) and MeOH (1 mL), was added 4M hydrochloric acid (4M in dioxane) (0.5 ml). The reaction was heated to 40 deg for 6 hr. The reaction was concentrated to dryness.

To a solution of hydrochloride salt (41.98 mg, 0.068 mmol), Moc-L-valine (25.2 mg, 0.144 mmol), and HATU (54.4 mg, 0.143 mmol) in DMF (1.5 mL), was added N,N-diisopropylethylamine (120 μl, 0.684 mmol). Stirred at rt o/n. The reaction mixture cooled to 0 degrees and 0.2 mL TFA was added. Purified by RP-HPLC (eluent: water/MeCN*0.1% TFA) to yield product as a bis-trifluoroacetate salt.

ES/MS: 861.5 (M$^+$).

1H NMR (400 MHz, Methanol-d4) δ 8.62 (d, J=11.4 Hz, 1H), 8.26-8.18 (m, 1H), 8.04-7.91 (m, 2H), 7.67 (d, J=8.8 Hz, 1H), 7.66-7.54 (m, 1H), 7.42 (d, J=5.5 Hz, 1H), 5.36-5.24 (m, 3H), 5.08 (dd, J=10.9, 6.8 Hz, 1H), 4.28 (dd, J=22.6, 8.0 Hz, 1H), 4.17-4.05 (m, 2H), 3.79 (s, 1H), 3.73-3.63 (m, 5H), 2.86 (d, J=12.5 Hz, OH), 2.54 (ddt, J=32.9, 11.8, 6.3 Hz, 2H), 2.41-2.31 (m, 1H), 2.32 (s, 3H), 2.09-1.89 (m, 3H), 1.59 (dd, J=23.3, 6.6 Hz, 5H), 1.48-1.32 (m, 6H), 1.24 (dd, J=8.5, 6.3 Hz, 2H), 1.13-0.81 (m, 13H).

Procedure 6 Example 9

Methyl ((S)-2-((2S,5S)-2-(4-chloro-5-(2-((2S,5S)-1-((S)-2-((2R,6R)-2,6-dimethyltetrahydro-2H-pyran-4-yl)-2-((methoxycarbonyl)amino)acetyl)-5-methylpyrrolidin-2-yl)-1,11-dihydroisochromeno[4',3':6,7]naphtho[1,2-d]imidazol-9-yl)-1H-imidazol-2-yl)-5-methylpyrrolidin-1-yl)-1-((2R,6R)-2,6-dimethyltetrahydro-2H-pyran-4-yl)-2-oxoethyl)carbamate

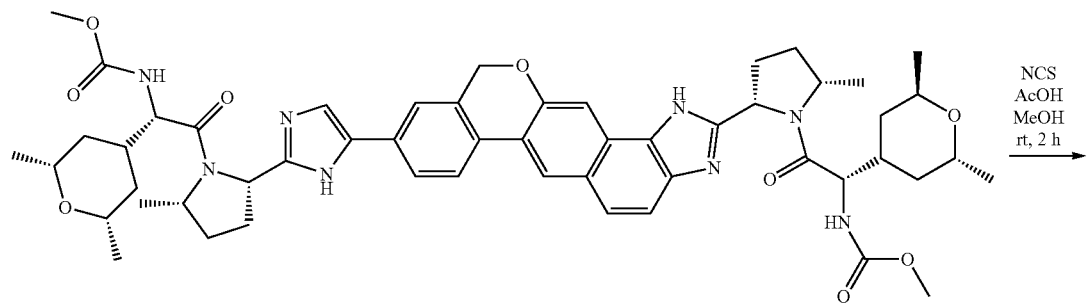

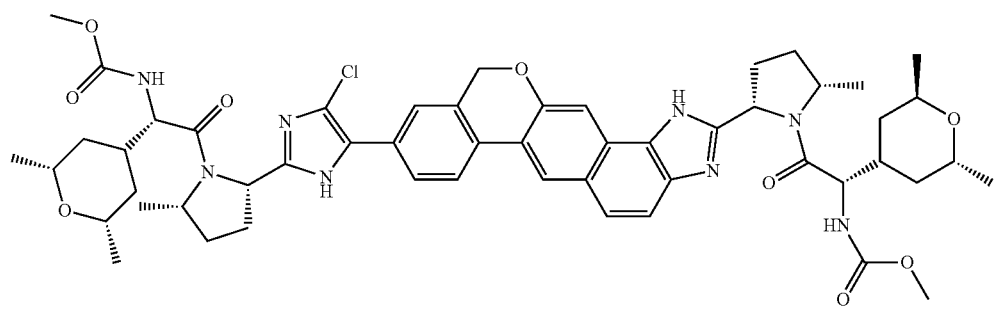

A solution of methyl ((S)-1-((2R,6R)-2,6-dimethyltetrahydro-2H-pyran-4-yl)-2-((2S,5S)-2-(5-(2-((2S,5S)-1-((S)-2-((2R,6R)-2,6-dimethyltetrahydro-2H-pyran-4-yl)-2-((methoxycarbonyl)amino)acetyl)-5-methylpyrrolidin-2-yl)-1,11-dihydroisochromeno[4',3':6,7]naphtho[1,2-d]imidazol-9-yl)-1H-imidazol-2-yl)-5-methylpyrrolidin-1-yl)-2-oxoethyl)carbamate (40.0 mg, 0.0417 mmol), n-chlorosuccinimide (6.1 mg, 0.0459 mmol), and acetic acid (1.25 mg, 0.0209 mmol) in methanol (1 mL) was stirred at room temperature for 2 hr. Purified by RP-HPLC (eluent: water/MeCN*0.1% TFA) to yield product as a trifluoroacetate salt.

ES/MS: 993.6 (M+).

1H NMR (400 MHz, Methanol-d4) δ 8.65-8.47 (m, 1H), 8.12-7.93 (m, 2H), 7.88-7.71 (m, 2H), 7.69-7.55 (m, 2H), 5.42 (d, J=6.4 Hz, OH), 5.36-5.18 (m, 3H), 5.06-4.91 (m, 1H), 4.38-4.05 (m, 4H), 3.86-3.73 (m, 1H), 3.67 (dd, J=15.4, 9.2 Hz, 6H), 3.59-3.39 (m, 1H), 2.71-1.99 (m, 5H), 1.90 (dd, J=12.4, 6.3 Hz, 1H), 1.83-1.49 (m, 7H), 1.43 (td, J=13.3, 6.2 Hz, 1H), 1.28 (d, J=6.1 Hz, 2H), 1.19 (dd, J=6.6, 4.1 Hz, 3H), 1.14-1.04 (m, 6H), 1.00-0.81 (m, 3H).

Procedure 7 Example 18

Methyl ((2S,3S)-1-((2S,4S)-2-(4-cyclopropyl-5-(2-((2S,5S)-1-((methoxycarbonyl)-L-alyl)-5-methylpyrrolidin-2-yl)-1,11-dihydroisochromeno[4',3':6,7]naphtho[1,2-d]imidazol-9-yl)-1H-imidazol-2-yl)-4-(methoxymethyl)pyrrolidin-1-yl)-3-methyl-1-oxopentan-2-yl)carbamate

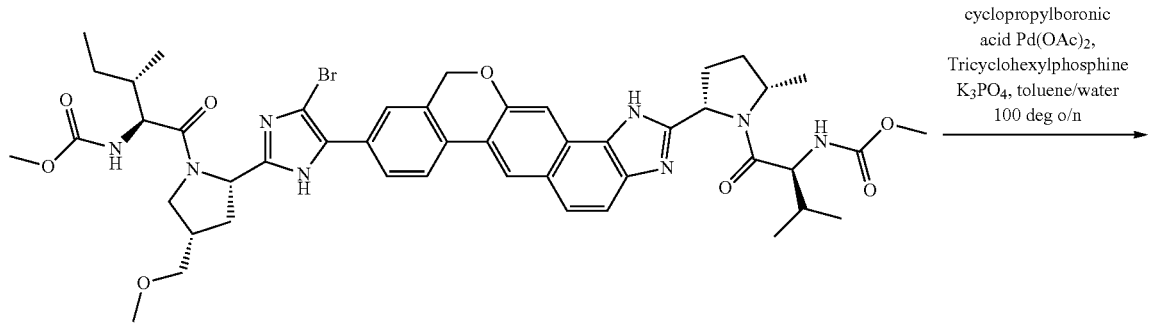

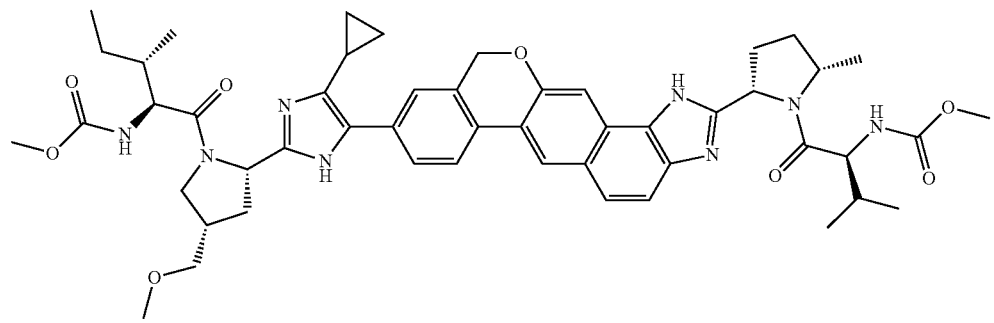

A mixture of methyl ((2S,3S)-1-((2S,4S)-2-(4-bromo-5-(2-((2S,5S)-1-((methoxycarbonyl)-L-valyl)-5-methylpyrrolidin-2-yl)-1,11-dihydroisochromeno[4',3':6,7]naphtho[1,2-d]imidazol-9-yl)-1H-imidazol-2-yl)-4-(methoxymethyl)pyrrolidin-1-yl)-3-methyl-1-oxopentan-2-yl)carbamate (40 mg, 0.0425 mmol), cyclopropylboronic acid (5.5 mg, 0.0637 mmol), palladium acetate (0.667 mg, 0.0030 mmol), tricyclohexylphosphine (2.38 mg, 0.0085 mmol) and potassium phosphate (27 mg, 0.127 mmol) in toluene/water (20/1 v/v, 2 mL) was heated at 100° C. overnight. The reaction mixture was evaporated to dryness, dissolved in water, extracted with ethyl acetate. The organic layer was washed with water and brine, dried over anhydrous sodium sulfate, then evaporated to dryness. The residue was purified by RP-HPLC (eluent: water/MeCN*0.1% TFA) to yield product as a trifluoroacetate salt.

ES/MS: 903.5 (M⁺).

1H NMR (400 MHz, Methanol-d4) δ 8.64 (d, J=5.9 Hz, 1H), 8.30-8.18 (m, 1H), 8.01 (dd, J=12.4, 9.0 Hz, 1H), 7.92 (s, 1H), 7.84-7.76 (m, 1H), 7.75-7.57 (m, 2H), 5.38-5.25 (m, 3H), 5.15 (dd, J=10.8, 7.2 Hz, 1H), 4.45-4.07 (m, 3H), 3.80 (s, 1H), 3.72-3.45 (m, 8H), 3.40 (s, 3H), 3.30-3.24 (m, 10H), 2.85-2.72 (m, 1H), 2.61 (dd, J=12.9, 6.9 Hz, 2H), 2.51-2.26 (m, 2H), 2.24-1.87 (m, 2H), 1.77 (s, 1H), 1.62 (d, J=6.6 Hz, 2H), 1.48 (d, J=11.7 Hz, 1H), 1.31-1.01 (m, 6H), 1.01-0.79 (m, 10H), 0.82-0.69 (m, 2H).

Procedure 8 Example 16

Methyl ((2S,3S)-1-((2S,4S)-2-(4-cyano-5-(2-((2S,5S)-1-((methoxycarbonyl)-L-valyl)-5-methylpyrrolidin-2-yl)-1,11-dihydroisochromeno[4',3':6,7]naphtho[1,2-d]imidazol-9-yl)-1H-imidazol-2-yl)-4-(methoxymethyl)pyrrolidin-1-yl)-3-methyl-1-oxopentan-2-yl)carbamate

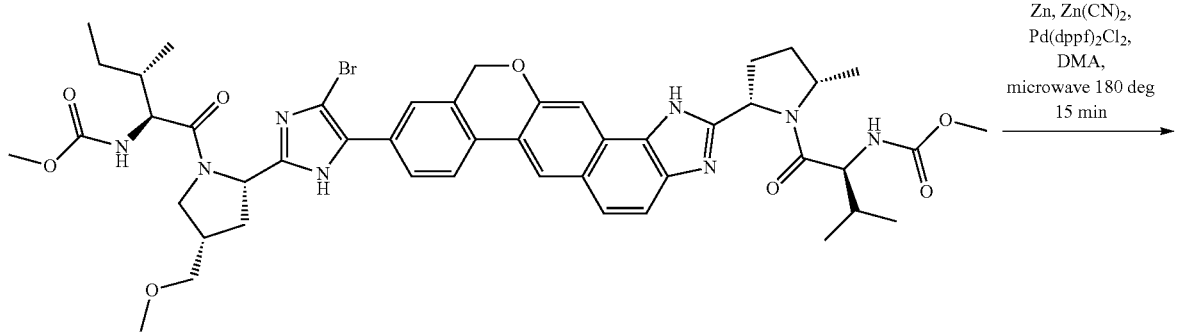

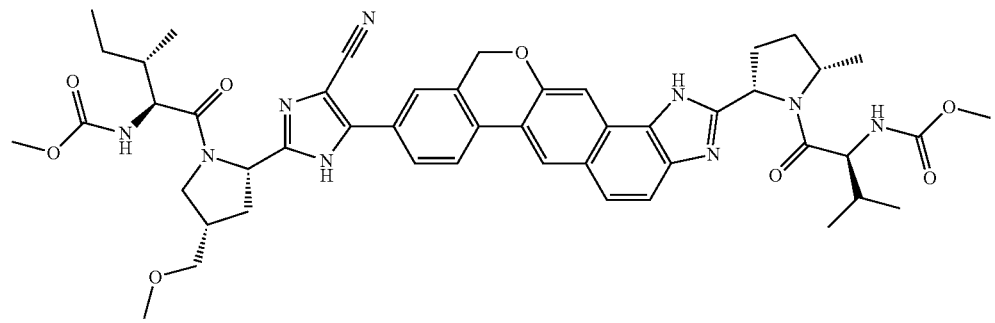

A mixture of methyl ((2S,3S)-1-((2S,4S)-2-(4-bromo-5-(2-((2S,5S)-1-((methoxycarbonyl)-L-valyl)-5-methylpyrrolidin-2-yl)-1-11-dihydroisochromeno[4',3':6,7]naphtho[1,2-d]imidazol-9-yl)-1H-imidazol-2-yl)-4-(methoxymethyl)pyrrolidin-1-yl)-3-methyl-1-oxopentan-2-yl)carbamate (15 mg, 0.0159 mml), Pd(dppf)Cl$_2$ (1.17 mg, 0.00159 mmol), Zn powder (0.521 mg, 0.00796 mmol), and Zn(CN)$_2$ (5.61 mg, 0.0478 mmol) in dimethyacetamide (0.3 mL) was degassed with argon for 2 min. The reaction was heated in a microwave at 180 deg for 15 min. The reaction mixture was filtered and purified by RP-HPLC (eluent: water/MeCN*0.1% TFA) to yield product as a trifluoroacetate salt.

ES/MS: 889.4 (M$^+$).

1H NMR (400 MHz, Methanol-d4) δ 8.58 (s, 1H), 8.35-8.07 (m, 2H), 8.07-7.79 (m, 3H), 7.77-7.49 (m, 2H), 5.28 (d, J=11.9 Hz, 3H), 5.07 (t, J=8.7 Hz, 1H), 4.46-4.03 (m, 4H), 3.79 (s, 1H), 3.72-3.35 (m, 12H), 2.93-2.22 (m, 4H), 2.16-1.89 (m, 3H), 1.86-1.37 (m, 4H), 1.32-0.63 (m, 16H).

Compound Table

The following compounds were prepared according to the Examples and Procedures described herein and indicated in Table 1 using the appropriate starting material(s) and appropriate protecting group chemistry as needed.

TABLE 1

| # | ES/MS m/z | Procedure |
|---|---|---|
| 1 | (M+) 924.4 | 6 |
| 2 | (M+) 877.8 | 1 |
| 3 | (MH+) 906.7 | 1 |
| 4 | (M+) 1013.8 | 1 |
| 5 | (M+) 900.6 | 1 |
| 6 | (M+) 925.8 | 1 |
| 7 | (M+) 883.6 | 6 |
| 8 | (M+) 929.6 | 4 |
| 9 | (M+) 993.6 | 6 |
| 10 | (M+) 1038.9 | 2 |
| 11 | (M+) 1000.2 | 7 |
| 12 | (M+) 909.6 | 6 |
| 13 | (M+) 874.8 | 8 |
| 14 | (M+) 898.6 | 1 |
| 15 | (M+) 909.4 | 6 |
| 16 | (M+) 889.4 | 8 |
| 17 | (M+) 943.4 | 4 |
| 18 | (M+) 903.5 | 7 |
| 19 | (M+) 897.4 | 6 |
| 20 | (M+) 951.6 | 6 |
| 21 | (M+) 853.4 | 1 |
| 22 | (M+) 881.4 | 1 |
| 23 | (M+) 881.4 | 1 |
| 24 | (M+) 989.4 | 1 |
| 25 | (M+) 881.5 | 1 |
| 26 | (M+) 825.4 | 1 |
| 27 | (M+) 853.5 | 1 |
| 28 | (M+) 853.4 | 1 |
| 29 | (M+) 961.3 | 1 |
| 30 | (M+) 853.4 | 1 |
| 31 | (M+) 899.3 | 1 |
| 32 | (M+) 917.4 | 1 |
| 33 | (M+) 837.1 | 3 |
| 34 | (M+) 905.4 | 1 |
| 35 | (M+) 933.4 | 1 |
| 36 | (M+) 1045.6 | 1 |
| 37 | (M+) 1041.3 | 1 |
| 38 | (M+) 859.4 | 5 |
| 39 | (M+) 887.5 | 5 |
| 40 | (M+) 887.5 | 5 |
| 41 | (M+) 995.5 | 5 |
| 42 | (M+) 924.5 | 5 |
| 43 | (M+) 861.5 | 5 |
| 44 | (M+) 889.6 | 5 |
| 45 | (M+) 997.5 | 5 |
| 46 | (M+) 889.5 | 5 |
| 47 | (M+) 925.5 | 5 |

1HNMR

Proton NMR data is shown in Table 2.

TABLE 2

(EC-need to fix integrations on some, check master xls table)

| # | 1H-NMR |
|---|---|
| 1 | 1H NMR (400 MHz, Methanol-d4) δ 8.83-7.50 (m, 7H), 6.26 (d, J = 7.0 Hz, 1H), 5.43 (d, J = 6.4 Hz, 1H), 5.33 (d, J = 9.3 Hz, 3H), 4.84 (s, 2H), 4.48-4.19 (m, 2H), 4.08 (t, J = 8.6 Hz, 1H), 3.91 (t, J = 6.1 Hz, 0H), 3.79 (d, J = 4.7 Hz, 1H), 3.77-3.65 (m, 5H), 2.77 (d, J = 8.9 Hz, 1H), 2.70-2.59 (m, 0H), 2.50 (s, 1H), 2.35 (d, J = 19.5 Hz, 2H), 2.06 (dddd, J = 55.8, 33.6, 15.6, 8.7 Hz, 3H), 1.66 (d, J = 6.7 Hz, 2H), 1.53 (d, J = 6.7 Hz, 2H), 1.36 (d, J = 6.3 Hz, 1H), 1.24 (d, J = 9.4 Hz, 7H), 1.18-0.94 (m, 5H), 1.06 (s, 6H), 0.88 (d, J = 6.8 Hz, 2H). |
| 2 | 1H NMR (400 MHz, Methanol-d4) δ 8.76 (dd, J = 4.4, 1.4 Hz, 0H), 8.66 (d, J = 3.3 Hz, 0H), 8.62 (s, 1H), 8.45 (dd, J = 8.4, 1.4 Hz, 0H), 8.21-8.00 (m, 3H), 7.90-7.82 (m, 2H), 7.75 (s, 0H), 7.68 (t, J = 4.5 Hz, 1H), 7.63 (d, J = 8.0 Hz, 2H), 7.54 (dd, J = 8.4, 4.5 Hz, 0H), 5.56 (dd, J = 9.4, 7.0 Hz, 1H), 5.41-5.26 (m, 3H), 5.22 (t, J = 7.9 Hz, 1H), 4.15 (ddd, J = 23.3, 20.9, 8.8 Hz, 4H), 3.98 (dd, J = 22.6, 9.8 Hz, 2H), 3.79 (d, J = 10.2 Hz, 1H), 3.68 (d, J = 6.6 Hz, 7H), 3.56 (s, 1H), 3.13 (d, J = 2.9 Hz, 1H), 2.60-2.47 (m, 1H), 2.41 (ddd, J = 16.7, 12.8, 7.8 Hz, 2H), 2.09 (ddd, J = 18.9, 13.3, 7.5 Hz, 5H), 0.83-0.74 (m, 2H), 0.67 (q, J = 6.8, 6.2 Hz, 2H). |
| 3 | 1H NMR (400 MHz, Methanol-d4) δ 8.76 (dd, J = 4.5, 1.4 Hz, 1H), 8.67 (d, J = 3.2 Hz, 1H), 8.64 (s, 1H), 8.46 (dd, J = 8.4, 1.4 Hz, 1H), 8.20-8.01 (m, 5H), 7.90-7.84 (m, 3H), 7.72-7.61 (m, 4H), 7.54 (dd, J = 8.4, 4.5 Hz, 1H), 5.56 (t, J = 8.3 Hz, 2H), 5.33 (d, J = 9.0 Hz, 4H), 5.22 (t, J = 8.0 Hz, 2H), 4.26-4.05 (m, 7H), 3.99 (t, J = 10.1 Hz, 3H), 3.79 (dd, J = 20.3, 10.3 Hz, 2H), 3.68 (d, J = 8.0 Hz, 13H), 3.55 (s, 1H), 3.08 (d, J = 2.5 Hz, 1H), 2.65-2.52 (m, 2H), 2.46 (dd, J = 12.8, 8.3 Hz, 2H), 2.37 (dd, J = 13.0, 7.7 Hz, 2H), 2.20-1.95 (m, 2H), 1.84 (d, J = 44.1 Hz, 5H), 1.67-1.43 (m, 1H), 1.29-1.07 (m, 4H), 1.07-0.82 (m, 38H), 0.82-0.72 (m, 4H), 0.67 (d, J = 10.2 Hz, 3H). |
| 4 | 1H NMR (400 MHz, Methanol-d4) δ 8.66 (d, J = 3.9 Hz, 1H), 8.16 (d, J = 8.3 Hz, 1H), 8.10 (d, J = 9.0 Hz, 1H), 7.97-7.84 (m, 2H), 7.72-7.64 (m, 2H), 5.66-5.45 (m, 1H), 5.35 (d, J = 3.1 Hz, 2H), 5.19 (d, J = 8.0 Hz, 1H), 4.85-4.75 (m, 1H), 4.74-4.62 (m, 1H), 4.16 (d, J = 9.8 Hz, 1H), 4.02 (d, J = 9.7 Hz, 1H), 3.93 (d, J = 9.9 Hz, 1H), 3.85-3.56 (m, 6H), 3.46 (s, 1H), 3.01 (dd, J = 13.4, 7.9 Hz, 0H), 2.90 (s, 1H), 2.64 (dd, J = |

TABLE 2-continued (EC-need to fix integrations on some, check master xls table)

| # | 1H-NMR |
|---|---|
| | 13.3, 9.1 Hz, 1H), 2.48 (dd, J = 12.8, 8.1 Hz, 1H), 2.35 (dd, J = 13.1, 7.6 Hz, 1H), 2.21-2.01 (m, 1H), 1.91 (d, J = 12.5 Hz, 0H), 1.39-1.13 (m, HH), 1.11 (s, 2H), 1.04-0.91 (m, 1H), 0.93-0.57 (m, 2H), 0.53-0.37 (m, 1H). |
| 5 | 1H NMR (400 MHz, Methanol-d4) δ 8.53 (d, J = 23.7 Hz, 1H), 8.09-7.93 (m, 2H), 7.85-7.73 (m, 1H), 7.70-7.48 (m, 2H), 5.32 (dd, J = 10.7, 7.0 Hz, 1H), 5.28-5.15 (m, 2H), 5.07 (ddd, J = 11.0, 7.9, 3.3 Hz, 1H), 4.53-4.31 (m, 1H), 4.26-4.09 (m, 2H), 3.77 (s, 1H), 3.66 (d, J = 8.5 Hz, 6H), 3.63-3.47 (m, 3H), 3.44-3.24 (m, HH), 2.81 (t, J = 9.2 Hz, 0H), 2.72-2.58 (m, 1H), 2.58-2.30 (m, 1H), 2.11-1.91 (m, 2H), 1.64 (d, J = 6.7 Hz, 2H), 1.28 (d, J = 6.2 Hz, 1H), 1.17 (t, J = 5.7 Hz, 3H), 1.08 (dd, J = 12.1, 6.8 Hz, 1H), 0.96 (d, J = 6.6 Hz, 2H), 0.88 (d, J = 6.9 Hz, 2H). |
| 6 | 1H NMR (400 MHz, Methanol-d4) δ 8.53 (d, J = 22.1 Hz, 1H), 8.01 (dt, J = 23.0, 9.6 Hz, 2H), 7.81-7.72 (m, 2H), 7.68-7.43 (m, 2H), 5.40-5.15 (m, 3H), 5.03 (dd, J = 9.8, 7.5 Hz, 1H), 4.41-4.07 (m, 3H), 4.00-3.89 (m, 2H), 3.77 (s, 1H), 3.74-3.48 (m, 8H), 3.45-3.25 (m, 10H), 2.63 (dq, J = 23.6, 6.1 Hz, 1H), 2.55-2.32 (m, 2H), 2.15-1.89 (m, 3H), 1.61 (dd, J = 21.4, 9.2 Hz, 4H), 1.55-1.20 (m, 2H), 1.08 (dd, J = 12.1, 6.7 Hz, 2H), 0.93 (dd, J = 31.0, 6.7 Hz, 4H). |
| 7 | 1H NMR (400 MHz, Methanol-d4) δ 8.56 (d, J = 19.5 Hz, 1H), 8.14-7.93 (m, 2H), 7.91-7.76 (m, 1H), 7.76-7.50 (m, 2H), 5.43-5.16 (m, 3H), 5.03 (dd, J = 10.0, 7.5 Hz, 1H), 4.21 (ddd, J = 24.6, 20.3, 9.2 Hz, 3H), 3.78 (d, J = 3.7 Hz, 1H), 3.66 (d, J = 11.6 Hz, 5H), 3.63-3.44 (m, 3H), 3.45-3.25 (m, 11H), 2.62 (dq, J = 18.7, 5.8 Hz, 1H), 2.56-2.31 (m, 2H), 2.15-1.88 (m, 3H), 1.64 (d, J = 6.7 Hz, 2H), 1.35-1.20 (m, 1H), 1.14-1.05 (m, 1H), 1.03-0.81 (m, 10H). |
| 8 | 1H NMR (400 MHz, Methanol-d4) δ 8.57 (d, J = 12.0 Hz, 1H), 8.49 (s, 2H), 8.21 (s, 1H), 8.08-7.87 (m, 6H), 7.79 (d, J = 8.3 Hz, 4H), 7.66-7.42 (m, 5H), 5.91 (d, J = 6.3 Hz, 1H), 5.31 (dd, J = 10.6, 6.8 Hz, 3H), 5.26-5.14 (m, 5H), 5.05 (ddd, J = 11.2, 7.6, 3.7 Hz, 3H), 4.37-4.11 (m, 9H), 3.78 (d, J = 4.7 Hz, 3H), 3.66 (d, J = 12.5 Hz, 15H), 3.53 (td, J = 13.9, 13.1, 6.3 Hz, 7H), 3.38 (s, 9H), 2.89-2.30 (m, 12H), 2.15-1.90 (m, 12H), 1.63 (dd, J = 6.7, 3.4 Hz, 7H), 1.31-1.20 (m, 4H), 1.07 (dd, J = 12.2, 6.7 Hz, 5H), 1.02-0.76 (m, 31H). |
| 9 | 1H NMR (400 MHz, Methanol-d4) δ 8.65-8.47 (m, 1H), 8.12-7.93 (m, 2H), 7.88-7.71 (m, 2H), 7.69-7.55 (m, 2H), 5.42 (d, J = 6.4 Hz, 0H), 5.36-5.18 (m, 3H), 5.06-4.91 (m, 1H), 4.38-4.05 (m, 4H), 3.86-3.73 (m, 1H), 3.67 (dd, J = 15.4, 9.2 Hz, 6H), 3.59-3.39 (m, 1H), 2.71-1.99 (m, 5H), 1.90 (dd, J = 12.4, 6.3 Hz, 1H), 1.83-1.49 (m, 7H), 1.43 (td, J = 13.3, 6.2 Hz, 1H), 1.28 (d, J = 6.1 Hz, 2H), 1.19 (dd, J = 6.6, 4.1 Hz, 3H), 1.14-1.04 (m, 6H), 1.00-0.81 (m, 3H). |
| 10 | 1H NMR (400 MHz, Methanol-d4) δ 8.59 (dd, J = 8.4, 3.5 Hz, 1H), 8.16-7.97 (m, 2H), 7.94-7.76 (m, 2H), 7.70-7.57 (m, 2H), 5.29 (dt, J = 11.1, 5.3 Hz, 3H), 5.00 (dd, J = 9.9, 7.6 Hz, 1H), 4.81-4.67 (m, 1H), 4.42-4.02 (m, 4H), 3.79 (d, J = 8.9 Hz, 0H), 3.71-3.58 (m, 5H), 3.52 (q, J = 14.0, 10.4 Hz, 1H), 2.90-2.74 (m, 1H), 2.68-1.84 (m, 7H), 1.80-1.34 (m, 8H), 1.33-1.02 (m, 13H), 1.00-0.82 (m, 3H). |
| 11 | 1H NMR (400 MHz, Methanol-d4) δ 8.66 (d, J = 3.1 Hz, 1H), 8.29-8.17 (m, 1H), 8.04 (d, J = 9.0 Hz, 1H), 7.95 (d, J = 3.5 Hz, 1H), 7.82-7.76 (m, 1H), 7.73-7.58 (m, 2H), 5.40-5.26 (m, 3H), 5.05 (dd, J = 11.1, 6.9 Hz, 1H), 4.85-4.68 (m, 2H), 4.39-4.05 (m, 5H), 3.91-3.58 (m, 8H), 3.58-3.45 (m, 1H), 2.90-1.89 (m, 6H), 1.84-1.51 (m, 6H), 1.50-1.37 (m, 1H), 1.30-0.80 (m, 19H), 0.73 (s, 1H). |
| 12 | 1H NMR (400 MHz, Methanol-d4) δ 8.60 (dd, J = 7.2, 4.0 Hz, 1H), 8.04 (ddd, J = 21.8, 13.6, 8.3 Hz, 3H), 7.91-7.73 (m, 2H), 7.70-7.57 (m, 2H), 5.29 (q, J = 4.6 Hz, 3H), 4.99 (dd, J = 9.9, 7.7 Hz, 1H), 4.49 (s, 1H), 4.21 (d, J = 9.0 Hz, 2H), 4.06 (d, J = 9.4 Hz, 1H), 3.95 (dd, J = 25.8, 10.8 Hz, 1H), 3.82 (d, J = 4.3 Hz, 1H), 3.75-3.54 (m, 5H), 3.43 (dd, J = 22.4, 11.3 Hz, 1H), 3.19 (t, J = 11.6 Hz, 1H), 2.94-2.68 (m, 1H), 2.59 (s, 1H), 2.55-2.27 (m, 1H), 2.17 (dd, J = 30.0, 7.9 Hz, 1H), 2.11-1.77 (m, 3H), 1.66 (dt, J = 29.8, 11.6 Hz, 1H), 1.51 (d, J = 6.7 Hz, 2H), 1.45-1.29 (m, 0H), 1.25-1.09 (m, 3H), 1.08 (s, 1H), 0.99 (dd, J = 17.9, 6.7 Hz, 3H), 0.90-0.69 (m, 3H). |
| 13 | 1H NMR (400 MHz, Methanol-d4) δ 8.67-8.53 (m, 1H), 8.12 (t, J = 8.3 Hz, 1H), 8.0 7.94 (m, 1H), 7.85 (d, J = 8.3 Hz, 2H), 7.61 (dd, J = 26.7, 7.8 Hz, 2H), 5.29 (d, J = 26.0 Hz, 3H), 5.07 (t, J = 8.5 Hz, 1H), 4.40-4.04 (m, 2H), 3.78 (s, 1H), 3.66 (d, J = 10.4 Hz, 4H), 3.61-3.45 (m, 3H), 3.38 (s, 3H), 2.83-2.28 (m, 5H), 2.15-1.90 (m, 3H), 1.63 (d, J = 6.7 Hz, 2H), 1.26 (d, J = 6.2 Hz, 1H), 1.15-0.73 (m, 11H). |
| 14 | 1H NMR (400 MHz, Methanol-d4) δ 8.56 (d, J = 11.9 Hz, 1H), 8.22 (s, 0H), 8.03 (dd, J = 17.0, 8.8 Hz, 2H), 7.90-7.71 (m, 2H), 7.71-7.53 (m, 2H), 5.39-5.19 (m, 3H), 5.03 (t, J = 8.7 Hz, 1H), 4.40-4.10 (m, 3H), 3.79 (s, 1H), 3.66 (d, J = 12.0 Hz, 5H), 3.60-3.45 (m, 3H), 3.38 (s, 3H), 2.74-2.30 (m, 5H), 2.15-1.89 (m, 2H), 1.75 (s, 1H), 1.63 (d, J = 6.6 Hz, 2H), 1.48 (d, J = 10.3 Hz, 1H), 1.27 (d, J = 6.2 Hz, 1H), 1.22-0.76 (m, 13H). |
| 15 | 1H NMR (400 MHz, Methanol-d4) δ 8.67-8.49 (m, 1H), 8.20 (d, J = 4.5 Hz, 0H), 8.16-7.94 (m, 2H), 7.94-7.75 (m, 2H), 7.73-7.55 (m, 1H), 5.30 (d, J = 4.3 Hz, 2H), 4.99 (t, J = 8.7 Hz, 1H), 4.76 (t, J = 6.9 Hz, 0H), 4.40-4.09 (m, 3H), 4.09-3.79 (m, 2H), 3.79-3.57 (m, 5H), 3.49-3.35 (m, 0H), 3.26-3.09 (m, 1H), 2.78 (s, 1H), 2.60 (dt, J = 12.7, 6.6 Hz, 1H), 2.37 (dddd, J = 33.4, 26.5, 16.7, 9.7 Hz, 3H), 2.21-1.98 (m, 2H), 1.91 (dd, J = 12.4, 6.7 Hz, 1H), 1.84-1.56 (m, 4H), 1.56-1.06 (m, 5H), 1.03-0.69 (m, 6H). |
| 16 | 1H NMR (400 MHz, Methanol-d4) δ 8.58 (s, 1H), 8.35-8.07 (m, 2H), 8.07-7.79 (m, 3H), 7.77-7.49 (m, 2H), 5.28 (d, J = 11.9 Hz, 3H), 5.07 (t, J = 8.7 Hz, 1H), 4.46-4.03 (m, 4H), 3.79 (s, 1H), 3.72-3.35 (m, 12H), 2.93-2.22 (m, 4H), 2.16-1.89 (m, 3H), 1.86-1.37 (m, 4H), 1.32-0.63 (m, 16H). |
| 17 | 1H NMR (400 MHz, Methanol-d4) δ 8.57 (d, J = 8.0 Hz, 1H), 8.27 (d, J = 40.6 Hz, 0H), 8.04 (dt, J = 21.0, 8.5 Hz, 2H), 7.92-7.77 (m, 2H), 7.62 (td, J = 13.2, 12.8, 9.0 Hz, 2H), 5.88 (s, 0H), 5.37-5.18 (m, 3H), 5.04 (t, J = 8.8 Hz, 1H), 4.40-4.01 (m, 3H), 3.79 (s, |

TABLE 2-continued (EC-need to fix integrations on some, check master xls table)

| # | 1H-NMR |
|---|---|
| | 1H), 3.71-3.44 (m, 8H), 3.40-3.24 (m, 20H), 2.89-2.76 (m, 0H), 2.74-2.57 (m, 1H), 2.43 (ddq, J = 36.2, 13.5, 6.9 Hz, 2H), 2.16-1.90 (m, 2H), 1.76 (s, 1H), 1.67-1.44 (m, 4H), 1.34-1.00 (m, 4H), 0.99-0.75 (m, 11H). |
| 18 | 1H NMR (400 MHz, Methanol-d4) δ 8.64 (d, J = 5.9 Hz, 1H), 8.30-8.18 (m, 1H), 8.01 (dd, J = 12.4, 9.0 Hz, 1H), 7.92 (s, 1H), 7.84-7.76 (m, 1H), 7.75-7.57 (m, 2H), 5.38-5.25 (m, 3H), 5.15 (dd, J = 10.8, 7.2 Hz, 1H), 4.45-4.07 (m, 3H), 3.80 (s, 1H), 3.72-3.45 (m, 8H), 3.40 (s, 3H), 3.30-3.24 (m, 10H), 2.85-2.72 (m, 1H), 2.61 (dd, J = 12.9, 6.9 Hz, 2H), 2.51-2.26 (m, 2H), 2.24-1.87 (m, 2H), 1.77 (s, 1H), 1.62 (d, J = 6.6 Hz, 2H), 1.48 (d, J = 11.7 Hz, 1H), 1.31-1.01 (m, 6H), 1.01-0.79 (m, 10H), 0.82-0.69 (m, 2H). |
| 19 | 1H NMR (400 MHz, Methanol-d4) δ 8.50 (d, J = 20.8 Hz, 1H), 7.98 (td, J = 19.4, 18.6, 8.7 Hz, 2H), 7.85-7.70 (m, 2H), 7.70-7.39 (m, 2H), 5.40-5.29 (m, 1H), 5.26-5.08 (m, 2H), 5.03 (dd, J = 9.7, 7.3 Hz, 1H), 4.42 (t, J = 6.2 Hz, 1H), 4.38-4.11 (m, 2H), 3.77 (s, 1H), 3.66 (d, J = 15.1 Hz, 5H), 3.63-3.47 (m, 3H), 3.38 (s, 3H), 2.92-2.30 (m, 3H), 2.17 (d, J = 18.9 Hz, 0H), 2.02 (s, 43H), 1.64 (d, J = 6.6 Hz, 2H), 1.46 (dt, J = 13.5, 6.7 Hz, 1H), 1.24 (dq, J = 20.8, 6.8 Hz, 2H), 1.08 (dd, J = 12.4, 6.7 Hz, 2H), 1.02-0.70 (m, 10H). |
| 20 | 1H NMR (400 MHz, Methanol-d4) δ 8.64-8.36 (m, 1H), 8.03-7.82 (m, 2H), 7.81-7.69 (m, 2H), 7.65-7.27 (m, 3H), 5.37-5.23 (m, 1H), 5.22-5.10 (m, 2H), 5.01 (dt, J = 9.7, 7.4 Hz, 1H), 4.47-4.04 (m, 2H), 3.84-3.64 (m, 5H), 3.64-3.50 (m, 2H), 3.38 (s, 3H), 2.76-2.25 (m, 3H), 2.14-1.93 (m, 3H), 1.64 (d, J = 6.7 Hz, 2H), 1.22 (tq, J = 14.9, 7.1, 6.2 Hz, 7H), 1.08 (dd, J = 14.1, 6.7 Hz, 2H), 1.01-0.78 (m, 4H). |
| 21 | 1H NMR (400 MHz, Methanol-d4) δ 8.63-8.55 (m, 1H), 8.09 (t, J = 8.9 Hz, 1H), 8.08-7.96 (m, 1H), 7.90-7.75 (m, 2H), 7.62 (t, J = 7.6 Hz, 1H), 5.29 (d, J = 9.5 Hz, 3H), 4.99 (t, J = 8.8 Hz, 1H), 4.23 (d, J = 6.9 Hz, 1H), 4.23-4.11 (m, 3H), 4.07 (d, J = 9.4 Hz, 1H), 3.78 (d, J = 3.2 Hz, 1H), 3.73-3.62 (m, 5H), 2.78 (s, 1H), 2.61 (dt, J = 12.1, 6.3 Hz, 1H), 2.44 (s, 2H), 2.49-2.24 (m, 1H), 2.20-2.00 (m, 1H), 1.98 (s, 3H), 1.63 (dd, J = 6.7, 1.7 Hz, 3H), 1.51 (d, J = 6.7 Hz, 2H), 1.28 (d, J = 6.1 Hz, 1H), 1.19 (d, J = 6.3 Hz, 1H), 1.12-0.91 (m, 8H), 0.85 (dd, J = 6.8, 2.6 Hz, 4H). |
| 22 | 1H NMR (400 MHz, Methanol-d4) δ 8.60 (t, J = 5.7 Hz, 2H), 8.14-8.02 (m, 2H), 8.02 (d, J = 7.8 Hz, 2H), 7.92-7.76 (m, 3H), 7.68-7.59 (m, 3H), 5.33-5.26 (m, 5H), 4.99 (t, J = 8.7 Hz, 1H), 4.27-4.11 (m, 4H), 3.78 (d, J = 5.3 Hz, 1H), 3.72 (s, 2H), 3.65 (d, J = 7.3 Hz, 6H), 2.75 (s, 1H), 2.67-2.56 (m, 1H), 2.35 (s, 5H), 2.08-2.00 (m, 1H), 1.75 (s, 5H), 1.63 (d, J = 6.7 Hz, 5H), 1.51 (d, J = 6.6 Hz, 3H), 1.22 (dd, J = 28.2, 6.3 Hz, 5H), 1.05-0.75 (m, 18H). |
| 23 | 1H NMR (400 MHz, Methanol-d4) δ 8.62 (d, J = 4.5 Hz, 2H), 8.21-8.10 (m, 2H), 8.13-7.95 (m, 5H), 7.91 (s, 1H), 7.84 (d, J = 8.3 Hz, 1H), 7.77 (s, 1H), 7.65 (s, 2H), 7.65 (d, J = 19.0 Hz, 1H), 5.46 (d, J = 6.7 Hz, 1H), 5.34-5.22 (m, 6H), 4.74 (d, J = 7.7 Hz, 1H), 4.37-4.23 (m, 6H), 3.76-3.64 (m, 12H), 2.70-2.53 (m, 3H), 2.30 (dt, J = 22.9, 8.5 Hz, 2H), 2.13-1.99 (m, 3H), 1.66 (d, J = 6.7 Hz, 5H), 1.52 (d, J = 6.6 Hz, 3H), 1.27 (d, J = 6.3 Hz, 3H), 1.20 (d, J = 6.3 Hz, 4H), 1.08 (d, J = 10.4 Hz, 19H), 0.94 (d, J = 15.3 Hz, 19H). |
| 24 | 1H NMR (400 MHz, Methanol-d4) δ 8.58 (d, J = 2.4 Hz, 1H), 8.11 (t, J = 7.8 Hz, 1H), 8.02-7.80 (m, 3H), 7.69-7.57 (m, 3H), 7.48 (dd, J = 26.1, 11.1 Hz, 1H), 5.33-5.20 (m, 4H), 5.01-4.92 (m, 1H), 4.78-4.57 (m, 2H), 3.68 (d, J = 8.1 Hz, 5H), 3.57 (s, 1H), 3.28 (s, 1H), 2.61-2.24 (m, 5H), 2.20-1.98 (m, 2H), 1.92 (dd, J = 12.4, 6.4 Hz, 1H), 1.66 (d, J = 6.6 Hz, 3H), 1.56 (d, J = 6.6 Hz, 3H), 1.51-1.35 (m, 1H), 1.40-1.27 (m, 5H), 1.24 (q, J = 7.7, 7.3 Hz, 7H), 1.08 (d, J = 7.3 Hz, 5H). |
| 25 | 1H NMR (400 MHz, Methanol-d4) δ 8.57 (t, J = 9.1 Hz, 2H), 8.14-8.05 (m, 2H), 7.99 (s, 2H), 7.90-7.74 (m, 4H), 7.67-7.58 (m, 4H), 5.71 (s, 1H), 5.34-5.23 (m, 7H), 5.00 (t, J = 8.8 Hz, 1H), 4.83-4.75 (m, 1H), 4.29 (dd, J = 15.2, 7.5 Hz, 3H), 4.20 (d, J = 8.8 Hz, 2H), 3.79-3.63 (m, 13H), 2.82 (s, 1H), 2.68-2.53 (m, 2H), 2.37 (dddd, J = 32.4, 25.6, 18.2, 10.6 Hz, 8H), 2.11 (s, 2H), 2.07-1.99 (m, 1H), 1.91 (dd, J = 12.4, 6.7 Hz, 1H), 1.77 (s, 5H), 1.61 (d, J = 6.5 Hz, 5H), 1.56-1.46 (m, 4H), 1.24 (dd, J = 20.0, 6.2 Hz, 5H), 1.04 (d, J = 6.6 Hz, 6H), 1.00-0.81 (m, 20H). |
| 26 | 1H NMR (400 MHz, Methanol-d4) δ 8.63 (d, J = 8.9 Hz, 2H), 8.16-7.99 (m, 4H), 7.85 (s, 3H), 7.63 (dd, J = 12.8, 8.9 Hz, 4H), 5.40 (t, J = 7.3 Hz, 2H), 5.31 (d, J = 7.0 Hz, 5H), 5.12-5.04 (m, 2H), 4.27 (d, J = 7.3 Hz, 2H), 4.20 (t, J = 9.1 Hz, 4H), 4.02-3.81 (m, 3H), 3.66 (d, J = 6.2 Hz, 11H), 3.52 (s, 1H), 2.66 (d, J = 6.6 Hz, 3H), 2.31 (ddd, J = 27.7, 12.2, 5.9 Hz, 9H), 2.20-2.00 (m, 6H), 1.04-0.84 (m, 23H). |
| 27 | 1H NMR (400 MHz, cd3od) δ 8.61 (d, J = 17.1 Hz, 1H), 8.19-7.95 (m, 2H), 7.83 (d, J = 6.7 Hz, 2H), 7.74-7.54 (m, 2H), 5.40 (t, J = 7.5 Hz, 1H), 5.29 (dd, J = 13.7, 2.9 Hz, 2H), 5.08 (dd, J = 7.7, 5.9 Hz, 1H), 4.27 (dd, J = 9.9, 8.2 Hz, 2H), 4.11 (q, J = 10.2, 9.5 Hz, 0H), 3.95 (q, J = 8.2, 7.8 Hz, 1H), 3.86 (q, J = 7.2 Hz, 1H), 3.66 (d, J = 1.5 Hz, 2H), 3.65 (s, 2H), 3.51 (s, 0H), 3.05 (s, 0H), 2.67 (dd, J = 10.4, 5.2 Hz, 1H), 2.31 (ddt, J = 29.7, 23.0, 9.1 Hz, 4H), 2.20-2.09 (m, 0H), 2.09-1.90 (m, 0H), 1.77 (s, 2H), 1.65-1.37 (m, 1H), 1.22-0.98 (m, 0H), 0.98-0.72 (m, 11H). |
| 28 | 1H NMR (400 MHz, Methanol-d4) δ 8.62 (d, J = 7.0 Hz, 1H), 8.12 (d, J = 8.2 Hz, 1H), 8.08-7.97 (m, 1H), 7.85 (s, 1H), 7.67-7.58 (m, 2H), 5.40 (t, J = 7.5 Hz, 1H), 5.31 (d, J = 5.3 Hz, 2H), 5.12-5.04 (m, 1H), 4.49 (d, J = 5.6 Hz, 1H), 4.41 (d, J = 6.0 Hz, 1H), 4.10 (s, 1H), 3.94 (s, 2H), 3.86 (t, J = 8.1 Hz, 1H), 3.65 (d, J = 3.3 Hz, 5H), 2.38-2.32 (m, 2H), 2.26 (s, 2H), 2.09 (s, 1H), 2.16-2.00 (m, 1H), 1.93-1.85 (m, 1H), 1.51-1.16 (m, 3H), 0.96 (td, J = 7.4, 3.6 Hz, 6H), 0.82 (dd, J = 22.2, 6.8 Hz, 5H). |
| 29 | 1H NMR (400 MHz, cd3od) δ 8.62 (d, J = 2.6 Hz, 1H), 8.13 (dd, J = 8.4, 4.1 Hz, 1H), 8.02 (dd, J = 15.6, 8.9 Hz, 1H), 7.95-7.75 (m, 3H), 7.70-7.56 (m, 3H), 5.37 (t, J = 7.6 Hz, 1H), 5.31 (d, J = 5.6 Hz, 2H), 5.12-5.03 (m, 1H), 4.98-4.90 (m, 1H), 4.69-4.52 |

TABLE 2-continued (EC-need to fix integrations on some, check master xls table)

| # | 1H-NMR |
|---|---|
| | (m, 1H), 4.20 (s, 1H), 3.95 (ddd, J = 25.7, 19.3, 11.7 Hz, 3H), 3.69 (s, 3H), 3.67 (s, 3H), 3.42 (s, 1H), 2.65 (s, 0H), 2.33 (td, J = 13.3, 12.7, 6.4 Hz, 2H), 2.26-2.10 (m, 1H), 2.10-1.92 (m, 2H), 1.42-1.20 (m, 6H), 1.18 (d, J = 6.0 Hz, 8H), 1.09 (s, 3H). |
| 30 | 1H NMR (400 MHz, cd3od) δ 8.73 (dd, J = 4.4, 1.4 Hz, 0H), 8.59 (d, J = 18.6 Hz, 1H), 8.43 (dd, J = 8.5, 1.4 Hz, 0H), 8.20-7.93 (m, 2H), 7.92-7.77 (m, 2H), 7.70-7.60 (m, 1H), 7.60-7.54 (m, 1H), 7.51 (dd, J = 8.5, 4.5 Hz, 0H), 5.38 (t, J = 7.7 Hz, 1H), 5.33-5.18 (m, 2H), 5.09 (dd, J = 7.6, 6.1 Hz, 1H), 4.35 (dd, J = 6.0, 3.3 Hz, 2H), 4.21 (d, J = 0H), 4.10-3.89 (m, 2H), 3.89-3.78 (m, 1H), 3.66 (dd, J = 8.2, 2.8 Hz, 5H), 3.50-3.42 (m, 1H), 3.01 (s, 0H), 2.72-2.55 (m, 1H), 2.46-2.08 (m, 6H), 2.08-1.95 (m, 1H), 1.09-0.96 (m, 11H), 0.94 (d, J = 5.2 Hz, 7H). |
| 31 | 1H NMR (400 MHz, Methanol-d4) δ 8.62 (d, J = 6.0 Hz, 1H), 8.15-7.96 (m, 3H), 7.92-7.83 (m, 1H), 7.67 (s, 1H), 7.71-7.59 (m, 1H), 5.31 (d, J = 4.3 Hz, 3H), 5.05-4.96 (m, 1H), 4.23 (dd, J = 12.8, 5.7 Hz, 1H), 4.21-4.11 (m, 1H), 4.07 (d, J = 9.4 Hz, 1H), 3.79 (d, J = 4.4 Hz, 1H), 3.72-3.63 (m, 6H), 2.79 (s, 1H), 2.68-2.55 (m, 1H), 2.45 (s, 3H), 2.34 (dtt, J = 20.5, 13.0, 6.2 Hz, 2H), 2.20-2.04 (m, 1H), 2.04 (s, 3H), 1.94 (ddd, J = 18.5, 11.3, 4.9 Hz, 2H), 1.63 (d, J = 6.7 Hz, 3H), 1.51 (d, J = 6.7 Hz, 2H), 1.28 (d, J = 6.2 Hz, 1H), 1.20 (d, J = 6.2 Hz, 2H), 1.12-0.91 (m, 10H), 0.89-0.82 (m, 5H). |
| 32 | 1H NMR (400 MHz, Methanol-d4) δ 8.65-8.59 (m, 2H), 8.13 (d, J = 8.6 Hz, 3H), 8.05 (t, J = 9.4 Hz, 2H), 7.95 (d, J = 23.1 Hz, 3H), 7.89-7.81 (m, 1H), 7.76 (s, 1H), 7.69-7.61 (m, 3H), 5.41 (d, J = 6.7 Hz, 1H), 5.35-5.22 (m, 5H), 4.74 (t, J = 7.1 Hz, 1H), 4.66-4.49 (m, 4H), 4.34 (dd, J = 17.7, 9.0 Hz, 1H), 4.28-3.90 (m, 5H), 3.72-3.64 (m, 9H), 3.55 (d, J = 4.5 Hz, 2H), 2.60 (dt, J = 13.0, 6.6 Hz, 2H), 2.46 (dt, J = 13.3, 7.0 Hz, 2H), 2.33 (dd, J = 13.1, 6.9 Hz, 2H), 2.08 (ddd, J = 34.0, 12.7, 6.3 Hz, 2H), 1.67 (d, J = 6.6 Hz, 5H), 1.53 (d, J = 6.6 Hz, 3H), 1.35 (d, J = 6.5 Hz, 2H), 1.24 (d, J = 6.4 Hz, 3H), 1.15-1.03 (m, 10H), 1.03-0.83 (m, 15H). |
| 33 | 1H NMR (400 MHz, Methanol-d4) δ 8.58 (d, J = 9.8 Hz, 1H), 8.21 (d, J = 4.8 Hz, 0H), 8.06 (dd, J = 19.4, 8.2 Hz, 2H), 7.90 (d, J = 12.6 Hz, 1H), 7.70-7.58 (m, 2H), 7.47 (s, 1H), 5.87 (s, 0H), 5.39 (d, J = 6.8 Hz, 0H), 5.28 (d, J = 6.1 Hz, 3H), 4.32 (s, 0H), 4.22 (d, J = 8.0 Hz, 1H), 4.14 (d, J = 8.9 Hz, 1H), 4.05 (d, J = 9.4 Hz, 1H), 3.79 (s, 2H), 3.66 (d, J = 6.4 Hz, 4H), 2.81 (s, 0H), 2.69 (d, J = 9.4 Hz, 0H), 2.65-2.55 (m, 1H), 2.40 (s, 3H), 2.39-2.24 (m, 1H), 2.17-2.07 (m, 0H), 2.08-1.88 (m, 2H), 1.63 (d, J = 6.8 Hz, 3H), 1.50 (d, J = 6.6 Hz, 2H), 1.27 (d, J = 6.4 Hz, 1H), 1.19 (d, J = 6.3 Hz, 1H), 1.05 (dd, J = 26.3, 6.7 Hz, 4H), 0.95 (t, J = 7.2 Hz, 4H), 0.85 (dd, J = 6.8, 3.3 Hz, 4H), 0.09 (d, J = 2.2 Hz, 0H). |
| 34 | 1H NMR (400 MHz, Methanol-d4) δ 8.60 (d, J = 15.6 Hz, 1H), 8.15-7.94 (m, 3H), 7.89-7.80 (m, 2H), 7.60 (s, 1H), 5.36-5.24 (m, 3H), 5.09-4.99 (m, 1H), 4.78 (d, J = 7.6 Hz, 1H), 4.62 (s, 1H), 4.23 (d, J = 8.4 Hz, 1H), 4.15 (t, J = 9.3 Hz, 1H), 3.73-3.62 (m, 7H), 3.09 (s, 2H), 2.98 (s, 1H), 2.85 (s, 2H), 2.83-2.73 (m, 1H), 2.67 (dt, J = 13.9, 7.2 Hz, 1H), 2.44 (dt, J = 14.7, 7.6 Hz, 1H), 2.33 (t, J = 7.8 Hz, 1H), 2.18 (s, 4H), 2.00 (dddd, J = 37.8, 30.0, 23.0, 8.8 Hz, 4H), 1.47-1.25 (m, 1H), 1.06 (s, 2H), 1.11-0.98 (m, 2H), 0.98-0.87 (m, 12H). |
| 35 | 1H NMR (400 MHz, Methanol-d4) δ 8.60 (d, J = 13.3 Hz, 1H), 8.24 (s, 0H), 8.08 (dt, J = 16.4, 8.9 Hz, 2H), 8.00 (d, J = 12.5 Hz, 1H), 7.89-7.80 (m, 2H), 7.76 (s, 0H), 7.61 (q, J = 9.2, 7.4 Hz, 2H), 5.87 (s, 0H), 5.39 (d, J = 7.9 Hz, 0H), 5.29 (d, J = 12.2 Hz, 4H), 5.09-5.00 (m, 1H), 4.25 (dd, J = 16.7, 9.5 Hz, 2H), 4.15 (d, J = 8.1 Hz, 0H), 3.84 (s, 0H), 3.73-3.62 (m, 7H), 3.08 (s, 2H), 2.84 (d, J = 18.7 Hz, 2H), 2.77 (d, J = 13.6 Hz, 1H), 2.67 (dt, J = 13.6, 7.1 Hz, 1H), 2.50-2.37 (m, 1H), 2.34 (d, J = 7.5 Hz, 1H), 2.17 (s, 5H), 2.14-1.92 (m, 3H), 1.93-1.86 (m, 2H), 1.74 (s, 6H), 1.60-1.51 (m, 2H), 1.18 (dt, J = 14.2, 7.6 Hz, 2H), 1.00 (dd, J = 16.1, 6.9 Hz, 1H), 0.95-0.81 (m, 12H), 0.09 (s, 0H). |
| 36 | 1H NMR (400 MHz, Methanol-d4) δ 8.56 (d, J = 16.3 Hz, 1H), 8.05 (dd, J = 15.5, 6.7 Hz, 1H), 7.99 (t, J = 8.4 Hz, 1H), 7.86-7.72 (m, 2H), 7.66-7.56 (m, 2H), 5.37-5.18 (m, 3H), 5.07 (t, J = 8.7 Hz, 1H), 4.20 (dt, J = 18.1, 8.9 Hz, 4H), 3.79 (s, 0H), 3.66 (d, J = 8.1 Hz, 6H), 3.58 (s, 1H), 3.08 (s, 1H), 2.87 (d, J = 9.0 Hz, 1H), 2.78-2.62 (m, 1H), 2.51-2.34 (m, 1H), 2.27-2.00 (m, 8H), 2.02-1.85 (m, 2H), 1.82-1.73 (m, 1H), 1.69 (s, 1H), 1.66-1.49 (m, 2H), 1.42 (td, J = 12.8, 5.5 Hz, 2H), 1.24 (d, J = 18.2, 6.9 Hz, 4H), 1.13 (dd, J = 8.1, 6.5 Hz, 6H), 1.05 (s, 1H), 1.07-0.87 (m, 3H). |
| 37 | 1H NMR (400 MHz, Methanol-d4) δ 8.63 (s, 2H), 8.10 (dd, J = 22.6, 8.7 Hz, 4H), 7.88 (s, 2H), 7.93-7.81 (m, 2H), 7.72-7.59 (m, 5H), 7.45 (d, J = 10.0 Hz, 1H), 5.34-5.22 (m, 6H), 5.07-4.96 (m, 5H), 4.67 (d, J = 7.2 Hz, 2H), 3.68 (d, J = 8.5 Hz, 9H), 3.08 (s, 3H), 2.85 (t, J = 8.1 Hz, 2H), 2.67 (dt, J = 13.8, 7.2 Hz, 2H), 2.43 (dt, J = 13.4, 8.0 Hz, 2H), 2.25 (d, J = 7.2 Hz, 1H), 2.20 (s, 6H), 2.07 (p, J = 12.5, 11.9 Hz, 4H), 1.93 (ddt, J = 25.9, 13.0, 6.6 Hz, 4H), 1.30-1.06 (m, 25H). |
| 38 | 1H NMR (400 MHz, Methanol-d4) δ 8.66 (d, J = 5.9 Hz, 2H), 8.29-8.19 (m, 2H), 8.05 (t, J = 8.7 Hz, 2H), 7.94 (s, 1H), 7.77 (d, J = 8.4 Hz, 1H), 7.73-7.58 (m, 3H), 5.37-5.25 (m, 4H), 5.04 (dd, J = 10.8, 6.7 Hz, 1H), 4.76 (t, J = 6.9 Hz, 1H), 4.36-4.20 (m, 1H), 4.11 (dd, J = 20.6, 8.7 Hz, 3H), 3.80 (s, 2H), 3.73-3.63 (m, 8H), 2.60 (dt, J = 13.0, 6.6 Hz, 1H), 2.51-2.23 (m, 3H), 2.08-1.92 (m, 2H), 1.97 (s, 2H), 1.59 (dd, J = 24.3, 6.6 Hz, 8H), 1.27 (dd, J = 8.7, 6.3 Hz, 3H), 1.18-1.00 (m, 8H), 0.97 (dd, J = 17.6, 6.7 Hz, 8H), 0.86 (dd, J = 10.9, 6.7 Hz, 8H), 0.76-0.67 (m, 2H). |

TABLE 2-continued (EC-need to fix integrations on some, check master xls table)

| # | 1H-NMR |
|---|---|
| 39 | 1H NMR (400 MHz, Methanol-d4) δ 8.67 (d, J = 7.3 Hz, 1H), 8.29-8.19 (m, 2H), 8.05 (t, J = 9.4 Hz, 1H), 7.95 (s, 1H), 7.77 (d, J = 8.1 Hz, 1H), 7.73-7.59 (m, 2H), 5.38-5.25 (m, 3H), 5.04 (dd, J = 10.9, 6.8 Hz, 1H), 4.29 (dd, J = 22.9, 11.7 Hz, 1H), 4.23-4.06 (m, 2H), 3.78 (s, 1H), 3.73-3.61 (m, 7H), 2.60 (dt, J = 12.8, 7.0 Hz, 1H), 2.52-2.44 (m, 1H), 2.38 (dd, J = 12.8, 6.4 Hz, 1H), 2.36-2.23 (m, 1H), 2.13 (qd, J = 9.3, 8.7, 5.1 Hz, 1H), 2.09-1.94 (m, 1H), 1.81-1.72 (m, 1H), 1.60 (dd, J = 24.2, 6.7 Hz, 6H), 1.31-1.08 (m, 6H), 1.05-0.67 (m, 16H). |
| 40 | 1H NMR (400 MHz, Methanol-d4) δ 8.66 (d, J = 10.6 Hz, 1H), 8.27-8.20 (m, 2H), 8.04 (dd, J = 16.3, 9.0 Hz, 1H), 7.94 (s, 1H), 7.77 (d, J = 8.2 Hz, 1H), 7.68 (t, J = 8.1 Hz, 2SH), 7.61 (d, J = 5.4 Hz, 1H), 5.38-5.25 (m, 4H), 5.04 (dd, J = 10.6, 6.7 Hz, 1H), 4.72 (t, J = 6.8 Hz, 1H), 4.34-4.20 (m, 3H), 3.76 (s, 1H), 3.73-3.62 (m, 8H), 2.59 (dt, J = 12.5, 7.1 Hz, 1H), 2.46 (d, J = 6.0 Hz, 1H), 2.35 (s, 4H), 2.29 (t, J = 6.9 Hz, 1H), 2.13 (ddd, J = 13.5, 8.6, 5.3 Hz, 1H), 2.07-1.93 (m, 1H), 1.78 (s, 3H), 1.58 (dd, J = 24.5, 6.6 Hz, 6H), 1.28 (q, J = 7.1, 6.6 Hz, 3H), 1.25-1.08 (m, 3H), 1.07-0.80 (m, 18H), 0.71 (q, J = 5.3 Hz, 2H). |
| 41 | 1H NMR (400 MHz, Methanol-d4) δ 8.65 (d, J = 15.6 Hz, 1H), 8.23 (d, J = 8.2 Hz, 1H), 8.09-7.93 (m, 2H), 7.86-7.73 (m, 1H), 7.70-7.49 (m, 4H), 5.38-5.21 (m, 3H), 5.01 (dd, J = 11.1, 6.8 Hz, 1H), 4.99-4.89 (m, 1H), 4.67 (d, J = 6.8 Hz, 1H), 4.57 (t, J = 7.2 Hz, 1H), 4.38-4.28 (m, 0H), 3.69 (d, J = 3.3 Hz, 6H), 3.56 (s, 1H), 3.26 (s, 1H), 2.59 (dt, J = 13.1, 6.7 Hz, 1H), 2.47 (dp, J = 12.2, 5.9 Hz, 2H), 2.35 (dd, J = 11.0, 5.2 Hz, 1H), 2.26 (ddt, J = 19.7, 13.3, 6.4 Hz, 1H), 2.13 (tt, J = 8.3, 5.2 Hz, 1H), 2.00 (ddd, J = 27.6, 13.2, 5.8 Hz, 2H), 1.64 (dd, J = 25.1, 6.6 Hz, 6H), 1.43 (d, J = 16.2, 6.5 Hz, 1H), 1.25 (dd, J = 19.8, 11.9 Hz, 9H), 1.18-1.04 (m, 8H), 0.79 (s, 1H), 0.76-0.67 (m, 2H). |
| 42 | 1H NMR (400 MHz, Methanol-d4) δ 8.67 (d, J = 8.0 Hz, 1H), 8.23 (dd, J = 8.3, 2.9 Hz, 1H), 8.06 (dd, J = 11.9, 8.9 Hz, 1H), 7.96 (s, 1H), 7.81-7.74 (m, 1H), 7.71-7.59 (m, 2H), 5.38-5.23 (m, 3H), 5.02 (dd, J = 11.1, 6.9 Hz, 1H), 4.72 (d, J = 6.9 Hz, 0H), 4.62 (dd, J = 15.4, 6.9 Hz, 2H), 4.47-3.90 (m, 4H), 3.66 (dd, J = 14.5, 3.9 Hz, 5H), 3.55 (s, 1H), 2.59 (dt, J = 13.1, 6.7 Hz, 1H), 2.46 (dt, J = 12.5, 6.1 Hz, 1H), 2.40-2.19 (m, 2H), 2.14 (tt, J = 8.8, 5.1 Hz, 1H), 1.99 (ddd, J = 28.0, 12.4, 5.9 Hz, 1H), 1.63 (dd, J = 24.1, 6.6 Hz, 5H), 1.34 (dd, J = 6.4, 4.3 Hz, 2H), 1.18-1.08 (m, 4H), 1.08-0.88 (m, 12H), 0.88-0.80 (m, 1H), 0.77-0.68 (m, 2H). |
| 43 | 1H NMR (400 MHz, Methanol-d4) δ 8.62 (d, J = 11.4 Hz, 1H), 8.26-8.18 (m, 1H), 8.04-7.91 (m, 2H), 7.67 (d, J = 8.8 Hz, 1H), 7.66-7.54 (m, 1H), 7.42 (d, J = 5.5 Hz, 1H), 5.36-5.24 (m, 3H), 5.08 (dd, J = 10.9, 6.8 Hz, 1H), 4.28 (dd, J = 22.6, 8.0 Hz, 1H), 4.17-4.05 (m, 2H), 3.79 (s, 1H), 3.73-3.63 (m, 5H), 2.86 (d, J = 12.5 Hz, 0H), 2.54 (ddt, J = 32.9, 11.8, 6.3 Hz, 2H), 2.41-2.31 (m, 1H), 2.32 (s, 3H), 2.09-1.89 (m, 3H), 1.59 (dd, J = 23.3, 6.6 Hz, 5H), 1.48-1.32 (m, 6H), 1.24 (d, J = 8.5, 6.3 Hz, 2H), 1.13-0.81 (m, 13H). |
| 44 | 1H NMR (400 MHz, Methanol-d4) δ 8.63 (d, J = 5.0 Hz, 1H), 8.26-8.18 (m, 1H), 7.99 (t, J = 9.5 Hz, 1H), 7.91 (s, 1H), 7.67 (d, J = 9.6 Hz, 1H), 7.66-7.54 (m, 1H), 7.54-7.39 (m, 1H), 5.30 (dt, J = 14.3, 5.1 Hz, 3H), 5.08 (dd, J = 11.0, 6.9 Hz, 1H), 4.78 (d, J = 7.0 Hz, 0H), 4.33-4.24 (m, 1H), 4.18 (dd, J = 16.4, 9.6 Hz, 2H), 3.78 (s, 1H), 3.72-3.59 (m, 6H), 3.40-3.30 (m, 1H), 2.85 (d, J = 12.8 Hz, 0H), 2.65-2.38 (m, 2H), 2.41-2.33 (m, 1H), 2.30 (ddt, J = 18.8, 12.7, 6.0 Hz, 1H), 2.00 (ddd, J = 23.1, 12.2, 5.7 Hz, 2H), 1.76 (q, J = 9.7, 8.6 Hz, 1H), 1.59 (dd, J = 25.1, 6.6 Hz, 6H), 1.50-1.33 (m, 6H), 1.25 (s, 3H), 1.25 (d, J = 11.4 Hz, 1H), 1.25-1.12 (m, 1H), 1.05-0.76 (m, 12H). |
| 45 | 1H NMR (400 MHz, Methanol-d4) δ 8.64 (s, 1H), 8.59 (s, 0H), 8.21 (t, J = 7.6 Hz, 1H), 8.01 (d, J = 9.2 Hz, 1H), 7.94 (s, 1H), 7.69-7.53 (m, 4H), 7.50-7.39 (m, 1H), 5.63 (t, J = 6.4 Hz, 0H), 5.48 (d, J = 19.4 Hz, 0H), 5.36-5.21 (m, 3H), 5.06 (dd, J = 11.3, 6.9 Hz, 1H), 5.00-4.86 (m, 2H), 4.68 (q, J = 6.8 Hz, 1H), 4.59 (dt, J = 14.0, 7.7 Hz, 1H), 4.33 (dt, J = 12.7, 6.3 Hz, 0H), 3.69 (d, J = 1.9 Hz, 5H), 3.58 (s, 1H), 3.34 (d, J = 7.0 Hz, 0H), 3.27 (s, 1H), 2.53 (ddt, J = 31.9, 13.3, 6.6 Hz, 2H), 2.33 (dtd, J = 39.5, 12.9, 12.5, 6.4 Hz, 2H), 2.08-1.93 (m, 2H), 1.63 (dd, J = 25.3, 6.6 Hz, 6H), 1.47-1.32 (m, 8H), 1.28 (d, J = 6.7 Hz, 5H), 1.21 (d, J = 6.5 Hz, 4H), 1.13 (s, 3H), 1.07 (s, 3H). |
| 46 | 1H NMR (400 MHz, Methanol-d4) δ 8.64 (d, J = 13.4 Hz, 1H), 8.23 (d, J = 8.4 Hz, 1H), 8.07-7.92 (m, 1H), 7.66 (dd, J = 9.0, 4.7 Hz, 1H), 7.58 (d, J = 8.0 Hz, 1H), 7.43 (d, J = 6.1 Hz, 1H), 5.71 (d, J = 6.4 Hz, 0H), 5.36-5.25 (m, 2H), 5.08 (dd, J = 10.8, 6.7 Hz, 1H), 4.34-4.20 (m, 2H), 4.15 (d, J = 7.6 Hz, 0H), 3.73 (d, J = 18.2 Hz, 1H), 3.72-3.60 (m, 4H), 3.34 (d, J = 7.9 Hz, 0H), 2.83 (d, J = 13.5 Hz, 0H), 2.64-2.42 (m, 1H), 2.44-2.24 (m, 2H), 2.07-1.93 (m, 1H), 1.78 (s, 2H), 1.57 (dd, J = 24.4, 6.6 Hz, 4H), 1.40 (ddd, J = 17.4, 11.0, 6.9 Hz, 5H), 1.27 (d, J = 6.2 Hz, 2H), 1.23-1.14 (m, 0H), 1.04 (t, J = 5.5 Hz, 1H), 1.00-0.83 (m, 7H), 0.83 (d, J = 7.3 Hz, 2H). |
| 47 | 1H NMR (400 MHz, Methanol-d4) δ 8.64 (d, J = 15.9 Hz, 1H), 8.22 (t, J = 6.8 Hz, 1H), 8.12 (s, 0H), 8.07-7.93 (m, 1H), 7.66 (d, J = 8.9 Hz, 1H), 7.58 (d, J = 7.9 Hz, 1H), 7.49 (s, 0H), 7.46-7.40 (m, 1H), 7.23 (d, J = 9.2 Hz, 1H), 5.80 (s, 0H), 5.36-5.22 (m, 3H), 5.07 (dd, J = 11.2, 6.9 Hz, 1H), 4.67-4.51 (m, 2H), 4.42 (s, 1H), 4.39-4.30 (m, 1H), 4.34-4.08 (m, 2H), 4.10-3.91 (m, 1H), 3.73-3.64 (m, 5H), 3.56 (s, 1H), 2.70 (s, 0H), 2.58 (dt, J = 13.2, 6.9 Hz, 1H), 2.54-2.21 (m, 4H), 2.07-1.92 (m, 2H), 1.63 (dd, J = 23.0, 6.6 Hz, 5H), 1.47-1.34 (m, 6H), 1.31 (t, J = 7.2 Hz, 2H), 1.12 (s, 2H), 1.08-0.93 (m, 9H), 0.91 (d, J = 2.1 Hz, 2H). |

TABLE 3

| # | Name |
|---|------|
| 1 | methyl ((S)-1-((2S,5S)-2-(5-(2-((2S,5S)-1-(O-(tert-butyl)-N-(methoxycarbonyl)-L-threonyl)-5-methylpyrrolidin-2-yl)-1,11-dihydroisochromeno[4',3':6,7]naphtho[1,2-d]imidazol-9-yl)-4-chloro-1H-imidazol-2-yl)-5-methylpyrrolidin-1-yl)-3-methyl-1-oxobutan-2-yl)carbamate |
| 2 | methyl ((S)-1-((S)-6-(4-chloro-5-(2-((S)-5-((methoxycarbonyl)-L-valyl)-5-azaspiro[2.4]heptan-6-yl)-1,11-dihydroisochromeno[4',3':6,7]naphtho[1,2-d]imidazol-9-yl)-1H-imidazol-2-yl)-5-azaspiro[2.4]heptan-5-yl)-3-methyl-1-oxobutan-2-yl)carbamate |
| 3 | methyl ((2S,3S)-1-((S)-6-(4-chloro-5-(2-((S)-5-((methoxycarbonyl)-L-isoleucyl)-5-azaspiro[2.4]heptan-6-yl)-1-dihydroisochromeno[4',3':6,7]naphtho[1,2-d]imidazol-9-yl)-1H-imidazol-2-yl)-5-azaspiro[2.4]heptan-5-yl)-3-methyl-1-oxopentan-2-yl)carbamate |
| 4 | methyl ((S)-1-((S)-6-(4-chloro-5-((S)-5-((S)-4,4,4-trifluoro-2-((methoxycarbonyl)amino)-3,3-dimethylbutanoyl)-5-azaspiro[2.4]heptan-6-yl)-1,11-dihydroisochromeno[4',3':6,7]naphtho[1,2-d]imidazol-9-yl)-1H-imidazol-2-yl)-5-azaspiro[2.4]heptan-5-yl)-4,4,4-trifluoro-3,3-dimethyl-1-oxobutan-2-yl)carbamate |
| 5 | methyl ((S)-1-((2S,5S)-2-(9-(4-chloro-2-((2S,4S)-1-(N-(methoxycarbonyl)-O-methyl-L-threonyl)-4-(methoxymethyl)pyrrolidin-2-yl)-1H-imidazol-5-yl)-1,11-dihydroisochromeno[4',3':6,7]naphtho[1,2-d]imidazol-2-yl)-5-methylpyrrolidin-1-yl)-3-methyl-1-oxobutan-2-yl)carbamate |
| 6 | methyl ((S)-1-((2S,5S)-2-(9-(4-chloro-2-((2S,4S)-1-((S)-2-((methoxycarbonyl)amino)-2-(tetrahydro-2H-pyran-4-yl)acetyl)-4-(methoxymethyl)pyrrolidin-2-yl)-1H-imidazol-5-yl)-1,11-dihydroisochromeno[4',3':6,7]naphtho[1,2-d]imidazol-2-yl)-5-methylpyrrolidin-1-yl)-3-methyl-1-oxobutan-2-yl)carbamate |
| 7 | methyl ((S)-1-((2S,5S)-2-(9-(4-chloro-2-((2S,4S)-1-((methoxycarbonyl)-L-valyl)-4-(methoxymethyl)pyrrolidin-2-yl)-1H-imidazol-5-yl)-1,11-dihydroisochromeno[4',3':6,7]naphtho[1,2-d]imidazol-2-yl)-5-methylpyrrolidin-1-yl)-3-methyl-1-oxobutan-2-yl)carbamate |
| 8 | methyl ((S)-1-((2S,5S)-2-(9-(4-bromo-2-((2S,4S)-1-((methoxycarbonyl)-L-valyl)-4-(methoxymethyl)pyrrolidin-2-yl)-1H-imidazol-5-yl)-1,11-dihydroisochromeno[4',3':6,7]naphtho[1,2-d]imidazol-2-yl)-5-methylpyrrolidin-1-yl)-3-methyl-1-oxobutan-2-yl)carbamate |
| 9 | methyl ((S)-2-((2S,5S)-2-(9-(4-chloro-2-((2S,5S)-1-((S)-2-((2R,6R)-2,6-dimethyltetrahydro-2H-pyran-4-yl)-2-((methoxycarbonyl)amino)acetyl)-5-methylpyrrolidin-2-yl)-1H-imidazol-5-yl)-1,11-dihydroisochromeno[4',3':6,7]naphtho[1,2-d]imidazol-2-yl)-5-methylpyrrolidin-1-yl)-1-((2R,6R)-2,6-dimethyltetrahydro-2H-pyran-4-yl)-2-oxoethyl)carbamate |
| 10 | methyl ((S)-2-((2S,5S)-2-(9-(4-bromo-2-((2S,5S)-1-((S)-2-((2R,6R)-2,6-dimethyltetrahydro-2H-pyran-4-yl)-2-((methoxycarbonyl)amino)acetyl)-5-methylpyrrolidin-2-yl)-1H-imidazol-5-yl)-1,11-dihydroisochromeno[4',3':6,7]naphtho[1,2-d]imidazol-2-yl)-5-methylpyrrolidin-1-yl)-1-((2R,6R)-2,6-dimethyltetrahydro-2H-pyran-4-yl)-2-oxoethyl)carbamate |
| 11 | methyl ((S)-2-((2S,5S)-2-(9-(4-cyclopropyl-2-((2S,5S)-1-((S)-2-((2R,6R)-2,6-dimethyltetrahydro-2H-pyran-4-yl)-2-((methoxycarbonyl)amino)acetyl)-5-methylpyrrolidin-2-yl)-1H-imidazol-5-yl)-1,11-dihydroisochromeno[4',3':6,7]naphtho[1,2-d]imidazol-2-yl)-5-methylpyrrolidin-1-yl)-1-((2R,6R)-2,6-dimethyltetrahydro-2H-pyran-4-yl)-2-oxoethyl)carbamate |
| 12 | methyl ((S)-2-((2S,5S)-2-(9-(4-chloro-2-((2S,5S)-1-((methoxycarbonyl)-L-valyl)-5-methylpyrrolidin-2-yl)-1H-imidazol-5-yl)-1,11-dihydroisochromeno[4',3':6,7]naphtho[1,2-d]imidazol-2-yl)-5-ethylpyrrolidin-1-yl)-2-oxo-1-(tetrahydro-2H-pyran-4-yl)ethyl)carbamate |
| 13 | methyl ((S)-1-((2S,5S)-2-(9-(4-cyano-2-((2S,4S)-1-((methoxycarbonyl)-L-valyl)-4-(methoxymethyl)pyrrolidin-2-yl)-1H-imidazol-5-yl)-1,11-dihydroisochromeno[4',3':6,7]naphtho[1,2-d]imidazol-2-yl)-5-methylpyrrolidin-1-yl)-3-methyl-1-oxobutan-2-yl)carbamate |
| 14 | methyl ((S)-1-((2S,5S)-2-(9-(4-chloro-2-((2S,4S)-1-((methoxycarbonyl)-L-isoleucyl)-4-(methoxymethyl)pyrrolidin-2-yl)-1H-imidazol-5-yl)-1,11-dihydroisochromeno[4',3':6,7]naphtho[1,2-d]imidazol-2-yl)-5-methylpyrrolidin-1-yl)-3-methyl-1-oxobutan-2-yl)carbamate |
| 15 | methyl ((S)-2-((2S,5S)-2-(9-(4-chloro-2-((2S,5S)-1-((methoxycarbonyl)-L-isoleucyl)-5-methylpyrrolidin-2-yl)-1H-imidazol-5-yl)-1,11-dihydroisochromeno[4',3':6,7]naphtho[1,2-d]imidazol-2-yl)-5-methylpyrrolidin-1-yl)-2-oxo-1-(tetrahydro-2H-pyran-4-yl)ethyl)carbamate |
| 16 | methyl ((S)-1-((2S,5S)-2-(9-(4-cyano-2-((2S,4S)-1-((methoxycarbonyl)-L-isoleucyl)-4-(methoxymethyl)pyrrolidin-2-yl)-1H-imidazol-5-yl)-1,11-dihydroisochromeno[4',3':6,7]naphtho[1,2-d]imidazol-2-yl)-5-methylpyrrolidin-1-yl)-3-methyl-1-oxobutan-2-yl)carbamate |
| 17 | methyl ((S)-1-((2S,5S)-2-(9-(4-bromo-2-((2S,4S)-1-((methoxycarbonyl)-L-isoleucyl)-4-(methoxymethyl)pyrrolidin-2-yl)-1H-imidazol-5-yl)-1,11-dihydroisochromeno[4',3':6,7]naphtho[1,2-d]imidazol-2-yl)-5-methylpyrrolidin-1-yl)-3-methyl-1-oxobutan-2-yl)carbamate |
| 18 | methyl ((S)-1-((2S,5S)-2-(9-(4-cyclopropyl-2-((2S,4S)-1-((methoxycarbonyl)-L-isoleucyl)-4-(methoxymethyl)pyrrolidin-2-yl)-1H-imidazol-5-yl)-1,11-dihydroisochromeno[4',3':6,7]naphtho[1,2-d]imidazol-2-yl)-5-methylpyrrolidin-1-yl)-3-methyl-1-oxobutan-2-yl)carbamate |
| 19 | methyl ((S)-1-((2S,5S)-2-(9-(4-chloro-2-((2S,4S)-1-((methoxycarbonyl)-L-alloisoleucyl)-4-(methoxymethyl)pyrrolidin-2-yl)-1H-imidazol-5-yl)-1,11-dihydroisochromeno[4',3':6,7]naphtho[1,2-d]imidazol-2-yl)-5-methylpyrrolidin-1-yl)-3-methyl-1-oxobutan-2-yl)carbamate |

TABLE 3-continued

| # | Name |
|---|------|
| 20 | methyl ((S)-1-((2S,5S)-2-(9-(4-chloro-2-((2S,4S)-4-(methoxymethyl)-1-((S)-4,4,4-trifluoro-2-((methoxycarbonyl)amino)-3,3-dimethylbutanoyl)pyrrolidin-2-yl)-1H-imidazol-5-yl)-1,11-dihydroisochromeno[4',3':6,7]naphtho[1,2-d]imidazol-2-yl)-5-methylpyrrolidin-1-yl)-3-methyl-1-oxobutan-2-yl)carbamate |
| 21 | methyl ((S)-1-((2S,5S)-2-(4-chloro-5-(2-((2S,5S)-1-((methoxycarbonyl)-L-valyl)-5-methylpyrrolidin-2-yl)-1,11-dihydroisochromeno[4',3':6,7]naphtho[1,2-d]imidazol-9-yl)-1H-imidazol-2-yl)-5-methylpyrrolidin-1-yl)-3-methyl-1-oxobutan-2-yl)carbamate |
| 22 | methyl ((2S,3S)-1-((2S,5S)-2-(4-chloro-5-(2-((2S,5S)-1-((methoxycarbonyl)-L-isoleucyl)-5-methylpyrrolidin-2-yl)-1,11-dihydroisochromeno[4',3':6,7]naphtho[1,2-d]imidazol-9-yl)-1H-imidazol-2-yl)-5-methylpyrrolidin-1-yl)-3-methyl-1-oxopentan-2-yl)carbamate |
| 23 | methyl ((S)-1-((2S,5S)-2-(4-chloro-5-(2-((2S,5S)-1-((S)-2-((methoxycarbonyl)amino)-3,3-dimethylbutanoyl)-5-methylpyrrolidin-2-yl)-1,11-dihydroisochromeno[4',3':6,7]naphtho[1,2-d]imidazol-9-yl)-1H-imidazol-2-yl)-5-methylpyrrolidin-1-yl)-3,3-dimethyl-1-oxobutan-2-yl)carbamate |
| 24 | methyl ((S)-1-((2S,5S)-2-(4-chloro-5-(2-((2S,5S)-5-methyl-1-((S)-4,4,4-trifluoro-2-((methoxycarbonyl)amino)-3,3-dimethylbutanoyl)pyrrolidin-2-yl)-1,11-dihydroisochromeno[4',3':6,7]naphtho[1,2-d]imidazol-9-yl)-1H-imidazol-2-yl)-5-methylpyrrolidin-1-yl)-4,4,4-trifluoro-3,3-dimethyl-1-oxobutan-2-yl)carbamate |
| 25 | methyl ((2S,3R)-1-((2S,5S)-2-(4-chloro-5-(2-((2S,5S)-1-((methoxycarbonyl)-L-alloisoleucyl)-5-methylpyrrolidin-2-yl)-1,11-dihydroisochromeno[4',3':6,7]naphtho[1,2-d]imidazol-9-yl)-1H-imidazol-2-yl)-5-methylpyrrolidin-1-yl)-3-methyl-1-oxopentan-2-yl)carbamate |
| 26 | methyl ((S)-1-((S)-2-(4-chloro-5-(2-((S)-1-((methoxycarbonyl)-L-valyl)pyrrolidin-2-yl)-1,11-dihydroisochromeno[4',3':6,7]naphtho[1,2-d]imidazol-9-yl)-1H-imidazol-2-yl)pyrrolidin-1-yl)-3-methyl-1-oxobutan-2-yl)carbamate |
| 27 | methyl ((2S,3S)-1-((S)-2-(4-chloro-5-(2-((S)-1-((methoxycarbonyl)-L-isoleucyl)pyrrolidin-2-yl)-1,11-dihydroisochromeno[4',3':6,7]naphtho[1,2-d]imidazol-9-yl)-1H-imidazol-2-yl)pyrrolidin-1-yl)-3-methyl-1-oxopentan-2-yl)carbamate |
| 28 | methyl ((2S,3R)-1-((S)-2-(4-chloro-5-(2-((S)-1-((methoxycarbonyl)-L-alloisoleucyl)pyrrolidin-2-yl)-1,11-dihydroisochromeno[4',3':6,7]naphtho[1,2-d]imidazol-9-yl)-1H-imidazol-2-yl)pyrrolidin-1-yl)-3-methyl-1-oxopentan-2-yl)carbamate |
| 29 | methyl ((S)-1-((S)-2-(4-chloro-5-(2-((S)-1-((S)-4,4,4-trifluoro-2-((methoxycarbonyl)amino)-3,3-dimethylbutanoyl)pyrrolidin-2-yl)-1,11-dihydroisochromeno[4',3':6,7]naphtho[1,2-d]imidazol-9-yl)-1H-imidazol-2-yl)pyrrolidin-1-yl)-4,4,4-trifluoro-3,3-dimethyl-1-oxobutan-2-yl)carbamate |
| 30 | methyl ((S)-1-((S)-2-(4-chloro-5-(2-((S)-1-((S)-2-((methoxycarbonyl)amino)-3,3-dimethylbutanoyl)pyrrolidin-2-yl)-1,11-dihydroisochromeno[4',3':6,7]naphtho[1,2-d]imidazol-9-yl)-1H-imidazol-2-yl)pyrrolidin-1-yl)-3,3-dimethyl-1-oxobutan-2-yl)carbamate |
| 31 | methyl ((S)-1-((2S,5S)-2-(4-bromo-5-(2-((2S,5S)-1-((methoxycarbonyl)-L-valyl)-5-methylpyrrolidin-2-yl)-1,11-dihydroisochromeno[4',3':6,7]naphtho[1,2-d]imidazol-9-yl)-1H-imidazol-2-yl)-5-methylpyrrolidin-1-yl)-3-methyl-1-oxobutan-2-yl)carbamate |
| 32 | methyl ((S)-1-((2S,5S)-2-(4-chloro-5-(2-((2S,5S)-1-((S)-4-fluoro-2-((methoxycarbonyl)amino)-3,3-dimethylbutanoyl)-5-methylpyrrolidin-2-yl)-1,11-dihydroisochromeno[4',3':6,7]naphtho[1,2-d]imidazol-9-yl)-1H-imidazol-2-yl)-5-methylpyrrolidin-1-yl)-4-fluoro-3,3-dimethyl-1-oxobutan-2-yl)carbamate |
| 33 | methyl ((S)-1-((2S,5S)-2-(9-(4-fluoro-2-((2S,5S)-1-((methoxycarbonyl)-L-valyl)-5-methylpyrrolidin-2-yl)-1H-imidazol-5-yl)-1,11-dihydroisochromeno[4',3':6,7]naphtho[1,2-d]imidazol-2-yl)-5-methylpyrrolidin-1-yl)-3-methyl-1-oxobutan-2-yl)carbamate |
| 34 | methyl ((S)-1-((2S,3aS,6aS)-2-(4-chloro-5-(2-((2S,3aS,6aS)-1-((methoxycarbonyl)-L-valyl)octahydrocyclopenta[b]pyrrol-2-yl)-1,11-dihydroisochromeno[4',3':6,7]naphtho[1,2-d]imidazol-9-yl)-1H-imidazol-2-yl)hexahydrocyclopenta[b]pyrrol-1(2H)-yl)-3-methyl-1-oxobutan-2-yl)carbamate |
| 35 | methyl ((2S,3S)-1-((2S,3aS,6aS)-2-(4-chloro-5-(2-((2S,3aS,6aS)-1-((methoxycarbonyl)-L-isoleucyl)octahydrocyclopenta[b]pyrrol-2-yl)-1,11-dihydroisochromeno[4',3':6,7]naphtho[1,2-d]imidazol-9-yl)-1H-imidazol-2-yl)hexahydrocyclopenta[b]pyrrol-1(2H)-yl)-3-methyl-1-oxopentan-2-yl)carbamate |
| 36 | methyl ((S)-2-((2S,3aS,6aS)-2-(4-chloro-5-(2-((2S,3aS,6aS)-1-((S)-2-((2R,6R)-2,6-dimethyltetrahydro-2H-pyran-4-yl)-2-((methoxycarbonyl)amino)acetyl)octahydrocyclopenta[b]pyrrol-2-yl)-1,11-dihydroisochromeno[4',3':6,7]naphtho[1,2-d]imidazol-9-yl)-1H-imidazol-2-yl)hexahydrocyclopenta[b]pyrrol-1(2H)-yl)-1-((2R,6R)-2,6-dimethyltetrahydro-2H-pyran-4-yl)-2-oxoethyl)carbamate |
| 37 | methyl ((S)-1-((2S,3aS,6aS)-2-(4-chloro-5-(2-((2S,3aS,6aS)-1-((S)-4,4,4-trifluoro-2-((methoxycarbonyl)amino)-3,3-dimethylbutanoyl)octahydrocyclopenta[b]pyrrol-2-yl)-1,11-dihydroisochromeno[4',3':6,7]naphtho[1,2-d]imidazol-9-yl)-1H-imidazol-2-yl)hexahydrocyclopenta[b]pyrrol-1(2H)-yl)-4,4,4-trifluoro-3,3-dimethyl-1-oxobutan-2-yl)carbamate |
| 38 | methyl ((S)-1-((2S,5S)-2-(4-cyclopropyl-5-(2-((2S,5S)-1-((methoxycarbonyl)-L-valyl)-5-methylpyrrolidin-2-yl)-1,11-dihydroisochromeno[4',3':6,7]naphtho[1,2-d]imidazol-9-yl)-1H-imidazol-2-yl)-5-methylpyrrolidin-1-yl)-3-methyl-1-oxobutan-2-yl)carbamate |
| 39 | methyl ((2S,3S)-1-((2S,5S)-2-(4-cyclopropyl-5-(2-((2S,5S)-1-((methoxycarbonyl)-L-isoleucyl)-5-methylpyrrolidin-2-yl)-1,11-dihydroisochromeno[4',3':6,7]naphtho[1,2-d]imidazol-9-yl)-1H-imidazol-2-yl)-5-methylpyrrolidin-1-yl)-3-methyl-1-oxopentan-2-yl)carbamate |

TABLE 3-continued

| # | Name |
|---|---|
| 40 | methyl ((2S,3R)-1-((2S,5S)-2-(4-cyclopropyl-5-(2-((2S,5S)-1-((methoxycarbonyl)-L-alloisoleucyl)-5-methylpyrrolidin-2-yl)-1,11-dihydroisochromeno[4',3':6,7]naphtho[1,2-d]imidazol-9-yl)-1H-imidazol-2-yl)-5-methylpyrrolidin-1-yl)-3-methyl-1-oxopentan-2-yl)carbamate |
| 41 | methyl ((S)-1-((2S,5S)-2-(4-cyclopropyl-5-(2-((2S,5S)-5-methyl-1-((S)-4,4,4-trifluoro-2-((methoxycarbonyl)amino)-3,3-dimethylbutanoyl)pyrrolidin-2-yl)-1,11-dihydroisochromeno[4',3':6,7]naphtho[1,2-d]imidazol-9-yl)-1H-imidazol-2-yl)-5-methylpyrrolidin-1-yl)-4,4,4-trifluoro-3,3-dimethyl-1-oxobutan-2-yl)carbamate |
| 42 | methyl ((S)-1-((2S,5S)-2-(4-cyclopropyl-5-(2-((2S,5S)-1-((S)-4-fluoro-2-((methoxycarbonyl)amino)-3,3-dimethylbutanoyl)-5-methylpyrrolidin-2-yl)-1,11-dihydroisochromeno[4',3':6,7]naphtho[1,2-d]imidazol-9-yl)-1H-imidazol-2-yl)-5-methylpyrrolidin-1-yl)-4-fluoro-3,3-dimethyl-1-oxobutan-2-yl)carbamate |
| 43 | methyl ((S)-1-((2S,5S)-2-(4-isopropyl-5-(2-((2S,5S)-1-((methoxycarbonyl)-L-valyl)-5-methylpyrrolidin-2-yl)-1,11-dihydroisochromeno[4',3':6,7]naphtho[1,2-d]imidazol-9-yl)-1H-imidazol-2-yl)-5-methylpyrrolidin-1-yl)-3-methyl-1-oxobutan-2-yl)carbamate |
| 44 | methyl ((2S,3S)-1-((2S,5S)-2-(4-isopropyl-5-(2-((2S,5S)-1-((methoxycarbonyl)-L-isoleucyl)-5-methylpyrrolidin-2-yl)-1,11-dihydroisochromeno[4',3':6,7]naphtho[1,2-d]imidazol-9-yl)-1H-imidazol-2-yl)-5-methylpyrrolidin-1-yl)-3-methyl-1-oxopentan-2-yl)carbamate |
| 45 | methyl ((S)-4,4,4-trifluoro-1-((2S,5S)-2-(4-isopropyl-5-(2-((2S,5S)-5-methyl-1-((S)-4,4,4-trifluoro-2-((methoxycarbonyl)amino)-3,3-dimethylbutanoyl)pyrrolidin-2-yl)-1,11-dihydroisochromeno[4',3':6,7]naphtho[1,2-d]imidazol-9-yl)-1H-imidazol-2-yl)-5-methylpyrrolidin-1-yl)-3,3-dimethyl-1-oxobutan-2-yl)carbamate |
| 46 | methyl ((2S,3R)-1-((2S,5S)-2-(4-isopropyl-5-(2-((2S,5S)-1-((methoxycarbonyl)-L-alloisoleucyl)-5-methylpyrrolidin-2-yl)-1,11-dihydroisochromeno[4',3':6,7]naphtho[1,2-d]imidazol-9-yl)-1H-imidazol-2-yl)-5-methylpyrrolidin-1-yl)-3-methyl-1-oxopentan-2-yl)carbamate |
| 47 | methyl ((S)-4-fluoro-1-((2S,5S)-2-(5-(2-((2S,5S)-1-((S)-4-fluoro-2-((methoxycarbonyl)amino)-3,3-dimethylbutanoyl)-5-methylpyrrolidin-2-yl)-1,11-dihydroisochromeno[4',3':6,7]naphtho[1,2-d]imidazol-9-yl)-4-isopropyl-1H-imidazol-2-yl)-5-methylpyrrolidin-1-yl)-3,3-dimethyl-1-oxobutan-2-yl)carbamate |

Biological Assays

Protocol for ZIKV reporter virus-based antiviral screening on Huh7 cells

1. Cells

Human hepatocyte-derived carcinoma cell line (Huh7)

2. Reagents

ViviRen™ Live Cell Substrate (Promega, Cat #E6492) or Nano Glo assay system (Promega: N1130)

White opaque 96-well TC-treated microplates (Corning, Cat #3916)

96-well Clear V-Bottom TC-treated Microplate (Corning, Cat #3894)

Complete cell culture media: DMEM (Gibco, Cat #10569) supplemented with 10% FBS (HyClone, Cat #SH30071.03IH25-40)+1% MEM Non-Essential Amino Acids Solution 100× (Gibco, Cat #11140050)+1% Penicillin-Streptomycin (10,000 U/mL) (Gibco, Cat #15140122).

Assay media: DMEM media (Gibco, Cat #31053028) supplemented with 2% FBS, 2% GlutaMAX™ Supplement (Gibco Cat #35050061), 1% Sodium Pyruvate solution (Gibco, Cat #11360070), 1% MEM Non-Essential Amino Acids Solution 100× and 1% Penicillin-Streptomycin (10,000 U/mL).

Trypsin-EDTA solution (Gibco, Cat #25200056)

3. Virus

Recombinant ZIKV strain with *Renilla* luciferase gene (strain FSS-Rlu) or *Nano* luciferase gene (Strain PRV-Nano, Dakar-Nano)

4. Instruments

BioTek Cytation 5 or other plate-readers for chemiluminescence detection model.

Eppendorf plate centrifuge

Plate shaker

Eppendorf multichannel pipettes

Procedures

Day 1 Preparation of Cells

Human hepatocyte-derived carcinoma cell line (Huh7) cells were detached from a T-175 flask by using a Trypsin-EDTA solution. The detached cells were suspended in complete culture media in a sterile 50-ml conical tube.

The 50-ml conical tube was centrifuged at 1200×rpm for 3 min at room temperature.

The cells were resuspended in assay media. The cell numbers were counted, and the cells diluted to a density of $3\times10^5$ cells/ml.

The cells were plated at 50 µl cells per well in White opaque 96-well plates (assay plates). Gently shake the plates to ensure cells to attach to the plate evenly.

The plated cells were incubated in a humidified incubator (37° C. with 5% $CO_2$).

Day 2 Infection

1) Nine serial (2-fold or 3-fold) concentrated compounds were prepared using 90% DMSO solution and DMSO controls in a clear V-bottom 96-well plate (compound plate).

For example:

| Final concentration | 10 µM | 5 µM | 2.5 µM | 1.25 µM | 0.625 µM | 0.313 µM | 0.156 µM | 0.078 µM | 0.0391 µM | 0.225% DMSO |
|---|---|---|---|---|---|---|---|---|---|---|
| 400× concentrated | 4 mM | 2 mM | 1 mM | 0.5 mM | 0.25 mM | 0.125 mM | 0.0625 mM | 0.0313 mM | 0.0156 mM | 90% DMSO |

2) The reporter virus stock was diluted to a concentration of 3×10$^4$ FFU (FFU: focus-forming unit)/ml using the assay media. 200 µl diluted virus per well was aliquoted into a clear V-bottom 96-well plate (mixing plate).

3) 1 µl above 400×concentrated compound dilutions was added from the compound plate to each well of the mixing plate. The plates were shaken on a plate shaker for 5 min.

4) 50 µl compound-virus mixture was added into each well of the assay plates (the MOI is about 0.1). The plates were shaken gently by mixing the virus evenly.

An example of the format for assay plate

| Dose 1 | Dose 2 | Dose 3 | Dose 4 | Dose 5 | Dose 6 | Dose 7 | Dose 8 | Dose 9 | DMSO control |
|---|---|---|---|---|---|---|---|---|---|
| Cpd 1, Replicate 1 | | | | | | | | | CC |
| Cpd 1, Replicate 2 | | | | | | | | | CC |
| Cpd 2, Replicate 1 | | | | | | | | | CC |
| Cpd 2, Replicate 2 | | | | | | | | | CC |
| Cpd 3, Replicate 1 | | | | | | | | | CC |
| Cpd 3, Replicate 2 | | | | | | | | | CC |

Note:
CC for cell control.

5) The plates were centrifuged at 1000 rpm for 15s.

6) The plates were incubated at 37° C. with 5% CO$_2$ in a humidified incubator for 48 hrs.

Day 4: Read Luciferase Signals

7) The ViviRen™ Live Cell Substrate was diluted in assay media for 3000× folds. 25 µl of diluted substrates was added into each well of the assay plates.

For Nano-Glo assay system, 50 µl diluted substrates (50×fold diluted from the stock in assay buffer) were added.

8) The plates were incubated at room temperature for 5 min.

9) Optimally, cell viability is measured using the Promega Cell-titer Glo kit (only used when ZIKV-Rlu was used for infection).

10) Luciferase signals were read using the Cytation 5 with gain value of 120-150.

Data Analysis a. The luciferase signals from DMSO-treated groups (un-treated controls) were set as 100%. The relative luciferase signals were obtained by normalizing the luciferase signals from each dilution-treated group to that of the controls.

b. The relative luciferase signals (Y axis) was plotted to the log 10 values of compound concentration (X axis) in the software GraphPad Prism 8 and the curves were fit using the nonlinear regression model (log(inhibitor) vs. response—Variable slope (four parameters), with constrains of bottom to 0 and top to 100).

c. The EC$_{50}$s values are reported below.

Biological assays were conducted to measure activity against ZIKV. As summarized in Table 3, the test compounds are inhibitors of ZIKV.

Biological assays were conducted to measure activity against ZIKV. As summarized in Table 4, the test compounds are inhibitors of ZIKV.

TABLE 4

| Compound # | EC50 ZIKV (nM) |
|---|---|
| 1 | 24.9 |
| 2 | 50.5 |
| 3 | 18.6 |
| 4 | 8.7 |
| 5 | 124.0 |
| 6 | 133.3 |
| 7 | 39.0 |
| 8 | 24.1 |
| 9 | 48.1 |
| 10 | 18.8 |
| 11 | 21.9 |
| 12 | 12.1 |
| 13 | 51.6 |
| 14 | 9.7 |
| 15 | 7.7 |
| 16 | 43.4 |
| 17 | 15.6 |
| 18 | 7.7 |
| 19 | 16.4 |
| 20 | 5.4 |
| 21 | 18.9 |
| 22 | 10.8 |
| 23 | 9.4 |
| 24 | 4.2 |
| 25 | 8.3 |
| 26 | 85.4 |
| 27 | 15.3 |
| 28 | 31.5 |
| 29 | 11.4 |
| 30 | 44.7 |
| 31 | 8.5 |
| 32 | 5.9 |
| 33 | 77.3 |
| 34 | 30.6 |
| 35 | 20.9 |
| 36 | 46.9 |
| 37 | 13.3 |
| 38 | 25.9 |
| 39 | 17.2 |
| 40 | 25.1 |
| 41 | 4.8 |

TABLE 4-continued

| Compound # | EC50 ZIKV (nM) |
|---|---|
| 42 | 21.4 |
| 43 | 57.7 |
| 44 | 11.5 |
| 45 | 4.9 |
| 46 | 26.7 |
| 47 | 21.7 |

The foregoing description of the specific embodiments will so fully reveal the general nature of the invention that others can, by applying knowledge within the skill of the art, readily modify and/or adapt for various applications such specific embodiments, without undue experimentation, without departing from the general concept of this disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

What is claimed is:

1. A compound of formula (I):

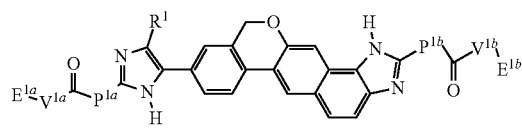

(I)

wherein:

R$^1$ is chloro or fluoro;

P$^{1a}$ and P$^{1b}$ are each independently selected from the group consisting of:

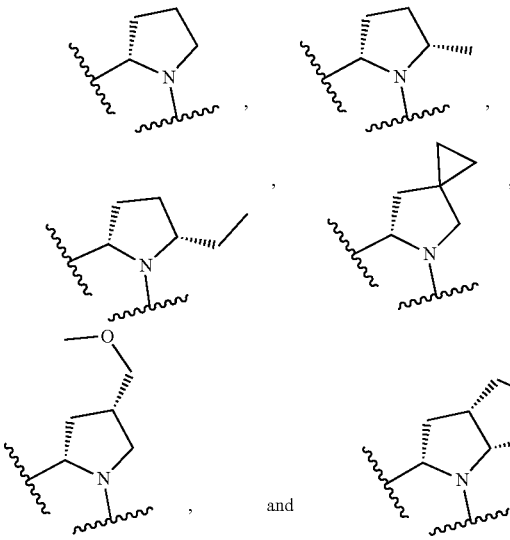

V$^{1a}$ and V$^{1b}$ are each independently selected from the group consisting of:

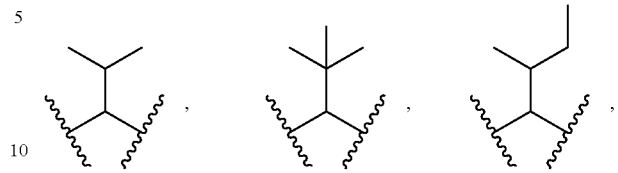

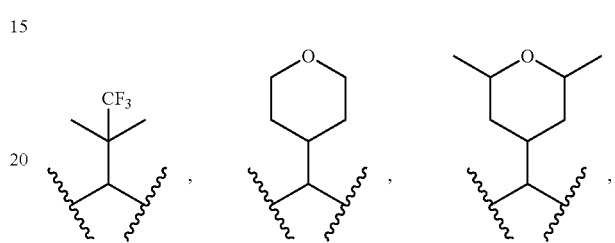

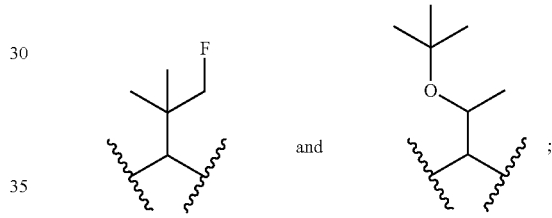

E$^{1a}$ and E$^{1b}$ are each independently —N(H)(C$_{1-6}$ alkoxycarbonyl), N(H)(C$_{3-12}$ cycloalkylcarbonyl), N(H)(C$_{1-6}$ alkylcarbonyl), or —N(H)(C$_{3-12}$ cycloalkoxycarbonyl);

or a pharmaceutically acceptable salt, stereoisomer or mixture of stereoisomers thereof.

2. The compound of claim 1, wherein R$^1$ is chloro.

3. The compound of claim 1 or claim 2, wherein V$^{1a}$ is

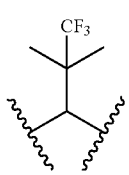

4. The compound of claim 1 or claim 2, wherein both V$^{1a}$ and V$^{1b}$ are

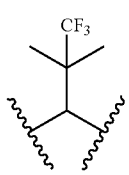

5. A compound of formula:
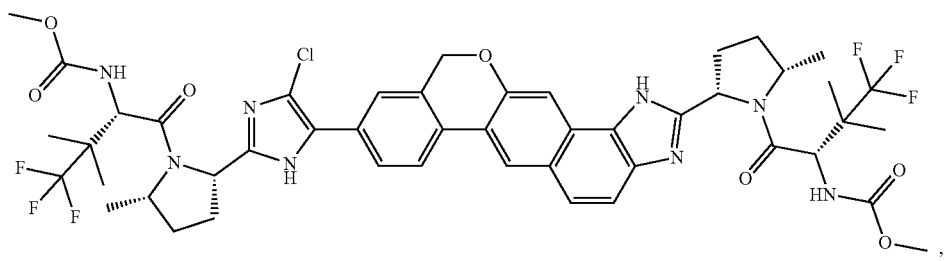
or a pharmaceutically acceptable salt, stereoisomer or mixture of stereoisomers thereof.
6. A pharmaceutical composition comprising a compound of claim 1, 2 or 5, or a pharmaceutically acceptable salt, stereoisomer or mixture of stereoisomers, together with at least one pharmaceutically acceptable excipient.
* * * * *